United States Patent [19]
Chaco et al.

[11] Patent Number: 5,594,786
[45] Date of Patent: Jan. 14, 1997

[54] PATIENT CARE AND COMMUNICATION SYSTEM

[75] Inventors: John Chaco, Seymour; Israel Hersh, Fairfield; Dmitry Orlovsky, Danbury; Joe Vincens, Prospect; Yaron Ram, Stamford, all of Conn.

[73] Assignee: Executone Information Systems, Inc., Darien, Conn.

[21] Appl. No.: 203,909

[22] Filed: Feb. 28, 1994

Related U.S. Application Data

[63] Continuation-in-part of Ser. No. 87,394, Jul. 2, 1993, and a continuation-in-part of Ser. No. 33,287, Mar. 16, 1993, which is a continuation-in-part of Ser. No. 924,101, Aug. 3, 1992, which is a continuation-in-part of Ser. No. 559,196, Jul. 27, 1990, Pat. No. 5,291,399.

[51] Int. Cl.$^6$ .................... H04M 11/00; H04M 11/04; G06F 15/00
[52] U.S. Cl. .................... 379/93; 379/38; 379/52; 128/904; 364/413.02
[58] Field of Search .................... 379/38, 52, 93, 379/96–97, 58, 102; 128/670, 904; 364/413.02, 413.03, 413.04; 348/734; 165/22

[56] References Cited

U.S. PATENT DOCUMENTS

| | | | |
|---|---|---|---|
| 3,364,427 | 1/1968 | Bennett | 455/89 |
| 3,617,637 | 11/1971 | Gorman, II | 348/14 |

(List continued on next page.)

FOREIGN PATENT DOCUMENTS

| | | |
|---|---|---|
| 0505627 | 9/1992 | European Pat. Off. |
| 2230365 | 10/1990 | United Kingdom. |
| 9105311 | 4/1991 | WIPO. |

OTHER PUBLICATIONS

"Great New Product Infrared Locator", Teleconnect, Feb., 1986, 4 pages.
Ooi, Lim & Lau, "Low Cost RF Identification and Locating System", IEEE Transactions on Consumer Electronics, vol. 35, No. 4, Nov., 1989, pp. 831–839.

(List continued on next page.)

*Primary Examiner*—Jason Chan
*Attorney, Agent, or Firm*—Dilworth & Barrese

[57] ABSTRACT

The present invention relates to a patient care and communication system which utilizes a central processing system and a plurality of remote stations electrically connected to the central processing system to facilitate visual and data communications. Each remote station includes telephone circuitry which is connected to a private branch exchange for telephone communications between stations. In addition, the private branch exchange is connected to a telephone exchange and a plurality of telephones for facilitating telephone communication therebetween. The central processing system facilitates the visual and data communications between the plurality of remote stations, and includes a system for determining which of the plurality of remote stations are transmitting the visual and data communications and which of the plurality of remote stations are to receive the visual and data communications. The central processing system also includes a system which establishes a communication link between the transmitting stations and the receiving stations. The remote stations include a processing system which also facilitates the visual, data and telephone communications and a display for displaying the visual communications. The present invention also includes a staff and/or patient locator system, in which each remote station includes an infrared receiver that receives infrared transmissions from a portable transmitter worn by a staff member or patient. The infrared transmissions include identity information associated with the person wearing the transmitter. The identity information is then transferred to the central processing system which determines the identity and location of each person wearing a portable transmitter.

28 Claims, 40 Drawing Sheets

U.S. PATENT DOCUMENTS

| | | | |
|---|---|---|---|
| 3,665,461 | 5/1972 | Gnägi et al. | 340/409 |
| 3,678,491 | 7/1972 | Day | 340/253 |
| 3,696,384 | 10/1972 | Lester | 340/312 |
| 3,767,859 | 10/1973 | Doering et al. | 340/312 |
| 3,805,227 | 4/1974 | Lester | 379/100 |
| 3,805,265 | 4/1974 | Lester | 340/6.5 R |
| 3,816,662 | 6/1974 | Shaver et al. | 379/103 |
| 3,872,440 | 3/1975 | Benz et al. | 340/171 R |
| 3,925,762 | 12/1975 | Heitlinger et al. | 340/150 |
| 3,946,159 | 3/1976 | Fay | 379/106 |
| 4,153,898 | 5/1979 | Larime | 340/396 |
| 4,216,462 | 8/1980 | McGrath et al. | 340/150 |
| 4,225,953 | 9/1980 | Simon et al. | 367/117 |
| 4,237,344 | 12/1980 | Moore . | |
| 4,275,385 | 6/1981 | White | 340/312 |
| 4,491,947 | 1/1985 | Frank | 370/94 |
| 4,536,646 | 8/1985 | Adams et al. | 235/377 |
| 4,553,267 | 11/1985 | Crimmins | 455/606 |
| 4,648,123 | 3/1987 | Schrock | 455/67 |
| 4,649,385 | 3/1987 | Aires et al. | 379/57 |
| 4,652,860 | 3/1987 | Weishaupt et al. | 340/539 |
| 4,757,553 | 7/1988 | Crimmins | 455/607 |
| 4,835,372 | 5/1989 | Gombrich et al. | 235/375 |
| 4,838,275 | 6/1989 | Lee | 128/670 |
| 4,885,571 | 12/1989 | Pauley et al. | 340/573 |
| 4,899,334 | 2/1990 | Shimizu | 370/60 |
| 4,905,231 | 2/1990 | Leung et al. | 370/94.1 |
| 4,916,441 | 4/1990 | Gombrich et al. | 340/712 |
| 4,955,000 | 9/1990 | Nastrom | 367/117 |
| 4,955,019 | 9/1990 | Mizuhara et al. | 370/85.7 |
| 4,967,195 | 10/1990 | Shipley | 340/825.52 |
| 4,969,508 | 11/1990 | Tate et al. | 165/22 |
| 4,977,619 | 12/1990 | Crimmins | 455/607 |
| 4,980,679 | 12/1990 | Klaubert | 340/765 |
| 5,038,800 | 8/1991 | Oba | 128/904 |
| 5,054,052 | 10/1991 | Nonami | 379/57 |
| 5,077,666 | 12/1991 | Brimm et al. | 364/413.02 |
| 5,119,104 | 6/1992 | Heller | 342/450 |
| 5,121,384 | 6/1992 | Ozeki et al. | 370/60 |
| 5,127,003 | 6/1992 | Doll, Jr. et al. | 370/110.1 |
| 5,130,793 | 7/1992 | Bordry et al. | 348/6 |
| 5,140,626 | 8/1992 | Ory et al. | 379/57 |
| 5,148,148 | 9/1992 | Shima et al. | 340/539 |
| 5,323,384 | 6/1994 | Norwood et al. | 379/58 |
| 5,390,238 | 2/1995 | Kirk et al. | 379/96 |

OTHER PUBLICATIONS

Mark Weiser "The Computer for the 21st Century", Scientific American, Sep. 1991, pp. 94–95, 98–100.

"Infra-Com®", A Staff and Equipment Locating and Signaling System from United Identification Systems Corp., 8 pages.

"Keeping Track of Alzheimer and Dementia Prone Patients Just Got Easier", Sycon, 6 pages.

Sekurmed Sales Brochure, 5 pages.

Franchi et al, Multimedia Perspectives for Next Generation PAC Systems, Session 2B: Pictural Archival and Communications Systems, pp. 156, 157, 159, 161, 163, 165, 167, and 169, 1992.

Fig. 10 NCS SYSTEM

*Call Indications at Nurse Control Stations*

| Call Priority Level | Arrow Flash Rate in Pulses Per Minute (PPM) | Incoming Call Display | | Tone Signaling in Pulses Per Minute (PPM) |
|---|---|---|---|---|
| | | Room-Bed Displayed on NCS Display 3272 | Call Level Displayed on NCS Display 3272 | |
| 1 Smoke Detector Call | 120 | yes-no | SMOKE DETECTOR | 120 |
| 2 Code Blue Call | 120 | yes-yes | CODE BLUE | 120 |
| 3 Staff Assist Call | 60 | yes-no | STAFF ASSIST | 60 |
| 4 Emergency Call | 60 | yes-no | EMERGENCY | 60 |
| 5 Patient Priority | 60 | yes-yes | PAT PRIORITY | 60 |
| 6 Personal Attention | steady | yes-yes | PERSONAL ATTEN | 1 @ 4PPM |
| 7 Overtime Call | 30 | yes-yes | OVERTIME | 2 @ 4PPM |
| 8 Cord Removal Call | 30 | yes-no | CORD REMOVAL | 2 @ 4PPM |
| 9 Patient Call | steady | yes-yes | PATIENT CALL | 1 @ 4PPM |
| 10 Staff Call | steady | yes-n/a | STAFF CALL | 1 @ 4PPM |
| 11 Auxiliary Device Call | 30 | yes-no | AUX DEV 1 CALL | 2 @ 4PPM |
| 12 Auxiliary Device Call | 30 | yes-no | AUX DEV 2 CALL | 2 @ 4PPM |

*Fig. 18*

*Call Indications at Patient Stations*

| Call Priority Level | Visual Indications | | | Tone Signaling in Pulses Per Minute (PPM) | Zone Indicator Assembly Group Indicator Color/Rate (PPM) |
|---|---|---|---|---|---|
| | Station Call Placement LED Indicator on Patient Stations (not shown) in PPM | Bed Call Placement LED Indicator on Patient Stations (not shown) in PPM | | | |
| 1 Smoke Detector Call | 120 | no | | 120 | Red/120 |
| 2 Code Blue Call | 120 | 120 | | no | Blue/120 |
| 3 Staff Assist Call | 60 | no | | no | White/60 |
| 4 Emergency Call | no | no | | no | White/60 |
| 5 Patient Priority | 60 | 60 | | single tone burst | White/60 |
| 6 Personal Attention | steady | steady | | single tone burst | White/steady |
| 7 Overtime Call | 30 | 30 | | no | Grn.-Amb./60-30 |
| 8 Cord Removal Call | 30 | no | | no | White/30 |
| 9 Patient Call | steady | steady | | single tone burst | White/steady |
| 10 Staff Call | n/a | n/a | | n/a | White/steady |
| 11 Auxiliary Device Call | 30 | no | | no | White/30 |
| 12 Auxiliary Device Call | 30 | no | | no | White/30 |

*Fig. 19*

Call Indications at Staff Stations

| Call Priority Level | Visual Indications | | | Tone Signaling Pulses Per Minute (PPM) | Zone Indicator Assembly (3022) Group Indicator Color/Rate (PPM) |
|---|---|---|---|---|---|
| | Incoming Call LED Indicator on Staff Station (not shown) (PPM) | Room-Bed Displayed on Staff Station Display 2422 | Call Level Displayed on Staff Station Display 2422 | | |
| 1 Smoke Detector Call | 120 | yes-no | SMOKE DETECTOR | 120 | Red/120 |
| 2 Code Blue Call | 120 | yes-yes | CODE BLUE | 120 | Blue/120 |
| 3 Staff Assist Call | 60 | yes-no | STAFF ASSIST | 60 | White/60 |
| 4 Emergency Call | 60 | yes-yes | EMERGENCY | 60 | White/60 |
| 5 Patient Priority | 60 | yes-yes | PAT PRIORITY | 60 | White/60 |
| 6 Personal Attention | steady | yes-yes | PERSONAL ATTEN | 1 @ 4PPM | White/steady |
| 7 Overtime Call | 30 | yes-yes | OVERTIME | 2 @ 4PPM | Grn.-Amb./60-30 |
| 8 Cord Removal Call | 30 | yes-no | CORD REMOVAL | 2 @ 4PPM | White/30 |
| 9 Patient Call | steady | yes-yes | PATIENT CALL | 1 @ 4PPM | White/steady |
| 10 Staff Call | steady | yes-n/a | STAFF CALL | 1 @ 4PPM | White/steady |
| 11 Auxiliary Device Call | 30 | yes-no | AUX DEV 1 CALL | 2 @ 4PPM | White/30 |
| 12 Auxiliary Device Call | 30 | yes-no | AUX DEV 2 CALL | 2 @ 4PPM | White/30 |

Fig. 20

FIG. 27   DATA FRAME FORMAT AND TIMING TO PBX

FIG. 28　DATA FRAME FORMAT AND TIMING TO TELEPHONE

PATIENT CARE AND COMMUNICATION SYSTEM

CROSS REFERENCE TO RELATED APPLICATION

This application is a continuation-in-part of application Ser. No. 08/087,394, filed Jul. 2, 1993, and is a continuation-in-part of application Ser. No. 08/033,287, filed Mar. 16, 1993, which is a continuation-in-part of copending application Ser. No. 07/924,101, filed Aug. 3, 1992, which is a continuation-in-part of application Ser. No. 07/559,196 filed on Jul. 27, 1990, now U.S. Pat. No. 5,291,399

BACKGROUND OF THE INVENTION

1. Field of the Invention.

The present invention relates to a patient care and communication system which incorporates telephone communication therein. The system utilizes a PBX to provide staff-to-staff, staff-to-patient and/or external telephone communications. The system is also capable of performing tasks such as monitoring medical equipment in patient rooms and maintaining patient medical data; facilitating staff-to-staff or staff-to-patient visual and data communications; and tracking the location of staff members or patients to provide maximum patient care. More detailed descriptions of the staff-patient communications and the monitoring of the medical equipment is provided in application Ser. No. 08/033,287, filed Mar. 16, 1993 which is incorporated herein by reference. A more detailed description of the system for tracking the location of personnel is provided in application Ser. No. 08/087,394, filed Jul. 2, 1993 and application Ser. No. 07/924,101, filed Aug. 3, 1992 both of which are incorporated herein by reference.

2. Description of the Related Art

In hospital or other health care environments, the nursing staff as well as other staff members are required to maintain and update patient information, provide patient care, and assist physicians in the treatment of patients. Often, these tasks have to be performed even though there are personnel shortages. Further, as medical technology continues to develop to provide treatment for a greater number of medical conditions, the volume of information that is maintained for each patient continues to grow rapidly. As a result, stress on the nursing staff has increased and information overload is fast approaching.

To more fully understand the above problem relating to health care, consider the types of data which are maintained for an individual patient. Typically, the staff members need to know the patient's name and address as well as any special dietary, environmental or physical space requirements of the patient. The attending physician or nursing staff may want to know the patient's condition, medical history and recent vital sign data. If the patient has had any diagnostic tests such as x-rays or ultrasound images made at the hospital, or at any other hospital, the attending physician may want to compare these test results with the results of newer tests to see how the patient's condition has progressed. In addition, if any medication has been prescribed, the physician or nursing staff may want to know the identity of the medication, when the last dose was taken and how the patient has complied with the dosage schedule.

Current systems utilized to manage such information includes the manual writing and processing of the information. Electronic systems utilized to process and store the information involve multiple computers, each configured to process portions of the vast amount of information. To obtain all the information in one place the information stored in each computer system must be manually combined. Furthermore, such electronic systems do not provide visual displays of text at stations provided in the patient's room, at the nurse control station or at stations provided in areas of the health care facility frequently occupied by the health care personnel.

In addition to processing the above information, the nursing staff attending to a number of patient's rooms may want to have some indication of each patient's condition at nursing stations which are far removed from the patient's bed. For example, if the patient has been admitted for a heart condition, it would be helpful if any recent vital signs that may indicate the onset of a heart attack could be displayed at the nurses station when the patient presses a call button.

One such system described in U.S. Pat. No. 4,835,372 to Gombrich et al. relates to a patient identification system for relating items with patients and for ensuring that an identified item corresponds to an identified patient. The system includes a computer system interconnected to a plurality of remote terminals by conventional telephone wiring. A RF modem provides for transmission and reception of RF signals to and from a bar code reading device, and the RF modem provides for transmission and reception of signals via existing telephone wire to and from the computer system using data over voice technology.

Another problem faced by care givers and by hospital administrators is determining the location of key personnel and equipment. In an emergency or during periods of personnel shortages, the ability to quickly locate an attending physician or other staff member to provide maximum patient care is desirable. Moreover, when special equipment is required to treat an emergency condition or when a ward of a hospital is experiencing personnel shortages, it is desirable that the equipment be quickly located to reduce the time spent to locate the equipment.

One type of system utilized to locate personnel within a hospital or other health care facility relies on audio paging systems, sign-in and sign-out sheets and broadcast paging systems. In a given situation, the audio paging system would be tried first. This system may not be effective if the person to be located is in an area where the paging system is not functioning properly or has been turned down, or if the person has left the hospital. After an unsuccessful audio page, the sign-in and sign-out sheets may be checked. If, however, the person to be located forgot to use the sign-in sheet or sign-out sheet, critical time may be lost in a second attempt to use the audio paging system. In addition, a search of the sign-in and sign-out sheets may require more time than is available in an emergency situation.

When the person to be located is outside of the hospital, broadcast paging systems are often the best way to convey an important message. These systems require the individual trying to locate the person to call the paging service, leave a message, wait for the paging service to send the message to the individual's pocket pager and then wait for the person being paged to call the paging service, receive the message and respond.

Another type of currently used locator system utilizes either radio frequency signals or infra-red signals to communicate the position of a mobile individual or object to a network of stationary transceivers. One such system, the InfraCom locating and signaling system available from United Identification Systems Corp. is designed for use in a hospital environment. Using this system, a network of infra-red transceivers located throughout a hospital can both transmit data to and receive data from a portable badge worn by hospital personnel or attached to the equipment to be located. This badge transmits a programmed identification signal to the network allowing the position of the badge to be indicated on a display of the floor plan of the hospital.

Another exemplary system, the TELOC PLUS personnel locator system available from Teloc, Inc., also uses two-way infra-red signaling to communicate the position of a portable badge in a stationary transceiver. In addition, the Teloc system may be coupled to a private branch exchange (PBX) to allow telephone calls from an individual to be routed to the telephone that is closest to the badge or to direct an intercom message to that telephone, thus providing an alternative to an audio paging system. Each of these systems is limited in the type of information that may be conveyed between the stationary transceiver network and the transceiver on the badge. In the described systems, only identification information providing an indication that switches, which are located on the badge have been activated, may be transmitted from the badge. Furthermore, if the transceiver on the badge fails or is damaged, a blank badge must be programmed to take its place. This program operation may be time consuming, leaving the individual or the piece of equipment invisible to the locating system for that period of time.

Therefore, a need exists for a patient care and communication system which integrates a staff locating system with a system which facilitates visual and data communications between staff members and patients and which maintains patient data. A need also exists for a patient care and communication system which utilizes a private-branch exchange to provide staff-to-staff, staff-to-patient and/or external communications. The present invention provides a patient care and communication system which provides communications through a PBX and which is capable of performing tasks such as monitoring medical equipment in patient rooms and maintaining patient medical data, facilitating voice, visual and data communications between staff members and the patients, as well as a system for tracking staff members to provide maximum patient care.

SUMMARY OF THE INVENTION

The present invention relates to a patient care and communication system which includes a central station having means for facilitating visual and data communications relating to health care and a plurality of remote stations connected to the central station. The remote stations include processing means for facilitating the visual and data communications and display means for displaying the visual communications.

The central station includes means for determining which of the plurality of remote stations are transmitting the visual and data communications and which of the plurality of remote stations are to receive the visual and data communications. In addition, the central station includes means for establishing a communication link between the transmitting stations and the receiving stations, and each of the plurality of remote stations includes telephone circuitry for connection to a private-branch exchange for telephone communications therebetween.

Preferably, the plurality of remote stations includes control stations, patient stations and staff stations and the central station includes means for directing the visual and data signals transmitted to the control stations to a predetermined number of patient stations and a predetermined number of staff stations.

The present invention also provides a patient care and communication system where the plurality of remote stations are configured and adapted for association in a group network such that predefined visual and data signal communications are transmitted to each station in the group. Zone controller means are provided to interface the central processing means to the transmitting and receiving stations.

In the preferred embodiment, the central station also includes means for controlling the private-branch exchange to establish audio communication between a predetermined number of control stations, a predetermined number of the patient stations and a predetermined number of the staff stations.

The patient stations of the present invention include patient control means which is connected thereto and provide a remote communication link between the patient and staff members or the patient and outside callers. The patient control means has a keypad, a speaker and a microphone for telephone communications to other stations or for external telephone communications. It should be noted that external communications includes telephone communications from within the hospital environment to locations outside the hospital environment, generally via public telephone lines.

The system of the present invention also relates to a method of providing patient care and communication between patient rooms and nurse stations in a health care facility. The method includes the steps of connecting a plurality of remote stations to a central station so as to facilitate visual and data communications therebetween, and connecting each remote station and the central station to a private-branch exchange for audio communications between the remote stations. At least one of said plurality of remote stations is positioned in each patient room located within the health care facility, positioning at least one of said plurality of remote stations in each nurse station of said health care facility, attending the remote station in each nurse station to receive the visual and data signals from said central station and the audio signals from the PBX and responding to the audio, visual and data signals.

BRIEF DESCRIPTION OF THE DRAWINGS

The preferred embodiments of the invention are described hereinbelow with reference to the drawings wherein:

FIGS. 18, 19 and 20 are tables which illustrate various call indications and associated tones generated by the stations in response to a particular call condition;

DETAILED DESCRIPTION OF THE PREFERRED EMBODIMENTS

Generally, the patient care and communication system of the present invention includes a communication network that provides routine and emergency signaling to health care facility staff members and provides high fidelity voice communication and data transmission between staff members in the health care facility and/or between patients and the staff members.

The exemplary embodiments of the automatic staff locator system of the patient care and communication system of the present invention described below, use a memory card as a personal database. As used herein, a memory card is a device approximately the same size and shape as an ordinary credit card which includes a non-volatile programmable memory. In the card used in the embodiments described below, two types of memory are used: an electronically erasable read only memory (EEROM) located internal to the card and a magnetic stripe located on the surface of the card. It is contemplated, however, that other forms of internal memory, such as a ferro-electric RAM or a CMOS memory with an integral battery, may be used. It is also contemplated that the functions described below may be implemented with other types of external memory, such as laser card technologies which either augment or replace the card memory. A more detailed description of the staff locator system and its operation is described in commonly assigned U.S. application Ser. No. 08/033,287, filed on Mar. 16, 1993 and which is incorporated herein by reference.

SYSTEM CONFIGURATIONS AND COMMUNICATIONS

Figure 1:
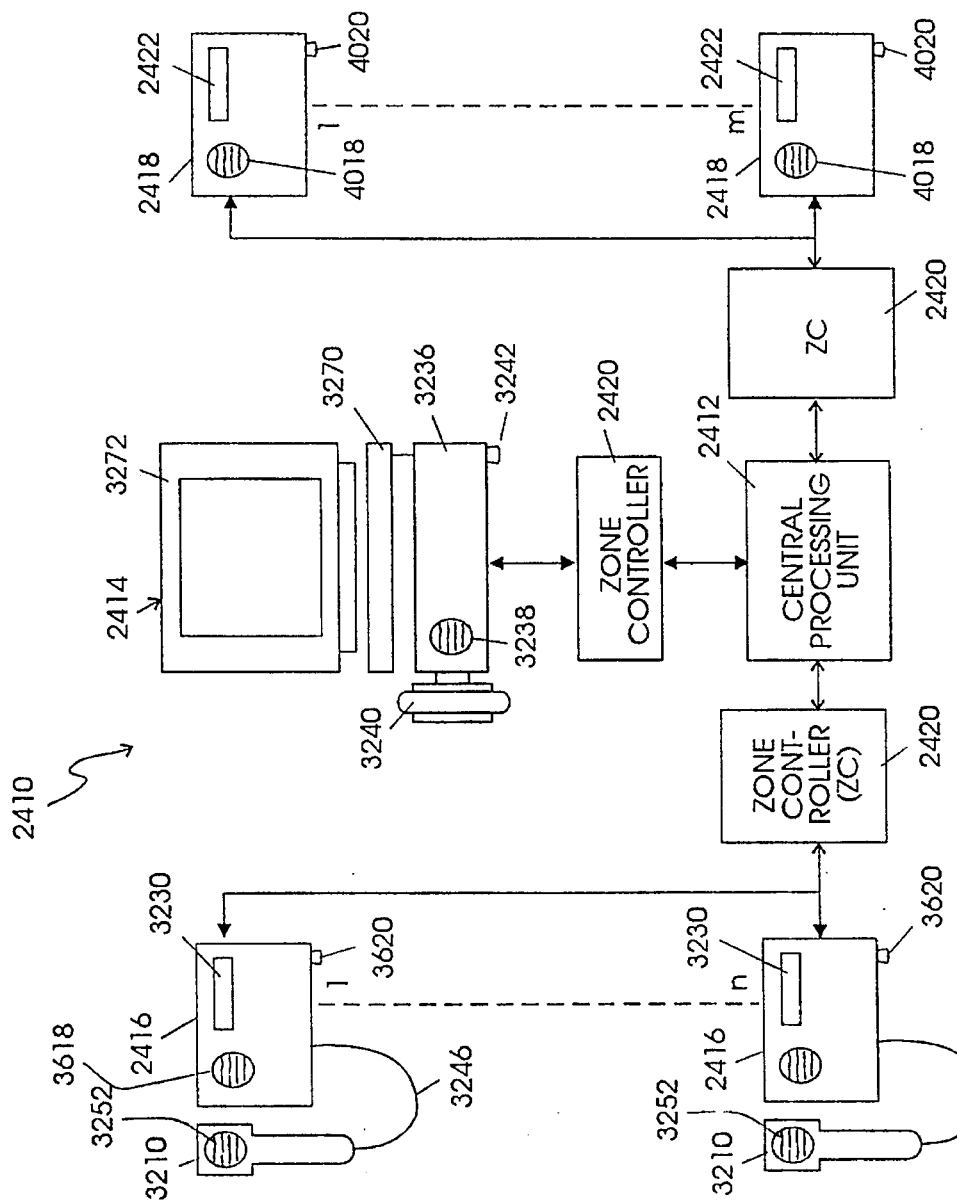
FIG. 1 is an illustration of the components of one embodiment of the patient care and communication system configuration of the present invention.

FIG. 1 is an illustration of the major components of the patient care and communication system according to the present invention, which includes central processor unit (CPU) 2412, nurse control stations 2414, patient stations 2416, staff stations 2418 and zone controllers 2420. Generally, the nurse control stations 2414 are installed at nurse stations located in various areas of the hospital or health care facility and provide a communication link to patients in their rooms. The patient stations 2416 are installed in patient rooms and can be configured to correspond to one patient or to multiple patients. The patient stations 2416 include patient station display 3230, speaker 3618, microphone 3620 and patient control unit 3210, all of which will be described in more detail below.

The staff stations 2418 are preferably installed in locations frequently occupied by other staff members in the hospital, such as staff locker rooms. Staff stations 2418 include staff station display 2422, speaker 4018 and microphone 4020, all of which will also be described in more detail below. The zone controllers 2420 include shared-RAM (S-RAM) memory 2512 (shown in FIG. 2) which is utilized as a buffer memory for data received from either CPU 2412 or from any of the above noted stations, hence the term shared-RAM.

As will be described in more detail below, the various types of stations which are positioned at different locations within the hospital interact with the aid of the CPU 2412 to perform numerous operations to reduce the information overload currently plaguing hospital staff members. Examples of the operations involving CPU 2412 include a call priority operation which prioritizes incoming calls (or messages) to nurse control station 2414 based upon the type of message received, so that staff members respond to the highest priority calls first. For example, if the incoming message relates to a fault in a smoke alarm secured in the patient's room, that message will be given the highest priority. Another operational example is a nurse follow operation which allows staff members to selectively route incoming calls directed to a nurse control station, to selected patient stations and/or staff stations so that when the staff members attending the nurse control station are required to leave the area, incoming calls to that station can be routed to locations where appropriate staff members can respond to the call. Another operational example is a voice paging operation which allows staff members to communicate with selected patient stations 2416 and/or staff stations 2418 from the nurse control station 2414. The interaction between the stations when performing these exemplary operations or tasks, as well as other operations, is conducted via a communication link which will be described in more detail below.

Figure 3:
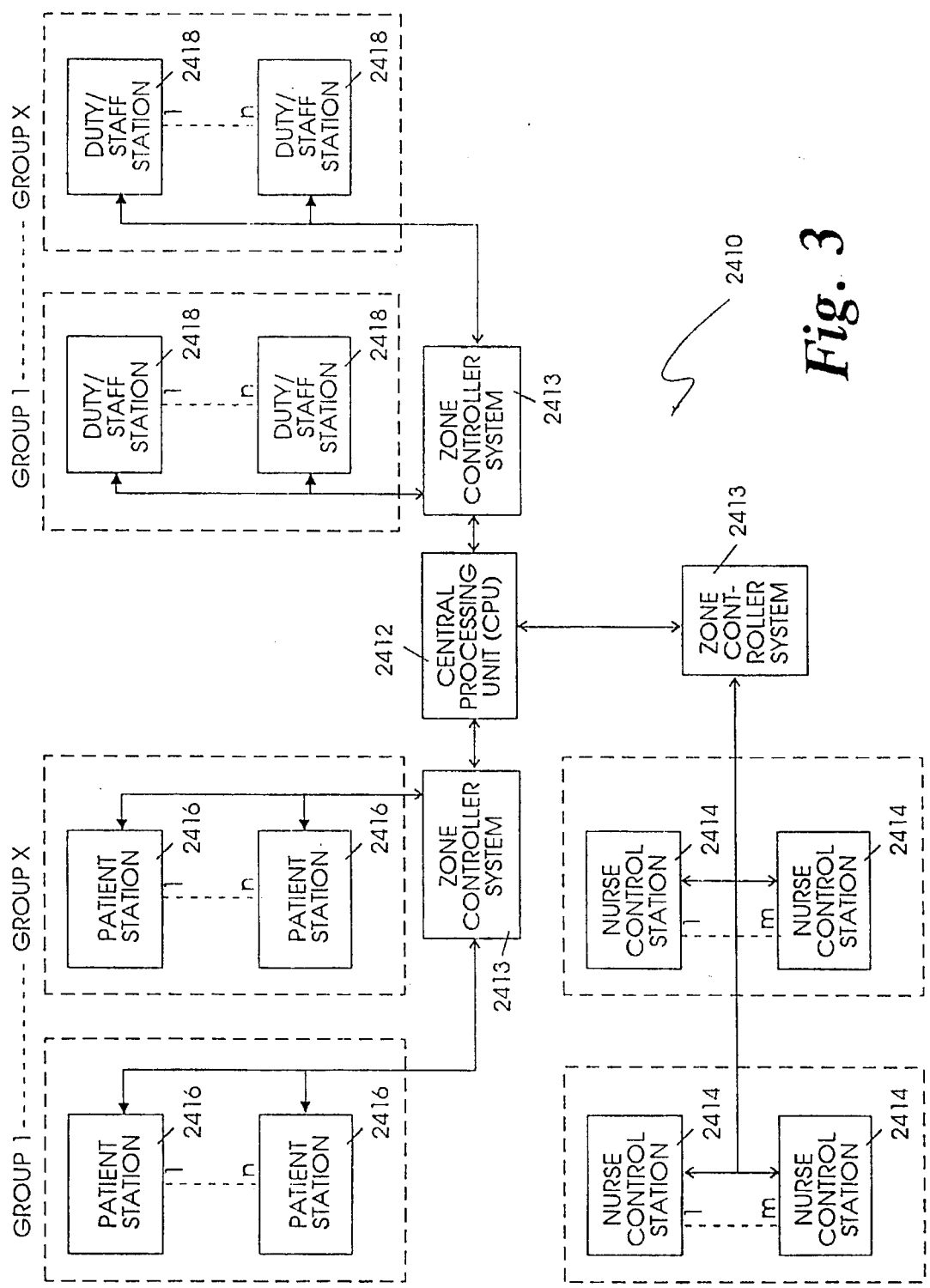
FIG. 3 is a functional block diagram of an another alternative embodiment of a system configuration of the present invention, illustrating grouping arrangements for the stations.

FIG. 3 illustrates the major components of system 2410 arranged in groups. As shown, CPU 2412 of the system of the present invention is configured, dimensioned and adapted to interface through zone controller systems 2413 with a predetermined number of station groups of patient stations 2416, staff stations 2418, and/or any combination thereof (e.g., the number of groups ranging between 1 and x, where "x" is preferably 8). Each station group includes between 1 and "n" stations, where "n" is preferably 35, and a predetermined number of station groups can be assigned to between 1 and "m" nurse control stations 2414, where "m" is preferably 8. For example, if a ward in a hospital has one hundred patient rooms (numbered from 100 to 200) which are single occupancy rooms, a staff locker room (Room 201) and a staff kitchen (Room 202), one patient station 2416 would be installed in each patient room and one staff station 2418 would be installed in the staff locker room and the staff kitchen. An exemplary array of station groupings (or the call assignment configuration) is shown in Table I below:

TABLE I

|         | RM1 | RM2 | RM3 | ... | RM32 | RM33 | RM34 | RM35 |
|---------|-----|-----|-----|-----|------|------|------|------|
| GROUP 1 | 100 | 101 | 102 | ... | 132  | 133  | 201  | 202  |
| GROUP 2 | 120 | 121 | 122 | ... | 152  | 153  | 201  | 202  |
| .       |     |     |     |     |      |      |      |      |
| .       |     |     |     |     |      |      |      |      |
| GROUP 8 | 154 | 155 | 156 | ... | 186  | 187  | 201  | 202  |

As shown in this exemplary call assignment configuration, rooms 100 through 133, 201 and 202 are assigned to station group 1. Rooms 120 through 153, 201 and 202 are assigned to station group 2 and rooms 154 through 187, 201 and 202 are assigned to station group 8. The station groupings can overlap in room coverage, thus, as illustrated in table I above, station groups 1 and 2 both include rooms 120 through 133.

In addition to the station groupings, the system of the present invention is configured so that each station group is assigned to a predetermined number of nurse control stations 2414. Table II below, illustrates an exemplary call assignment configuration for station groupings and their assignment to the nurse control stations 2414:

TABLE II

|      | Group 1 | Group 2 | ... | Group 8 |
|------|---------|---------|-----|---------|
| NCS1 | YES     | YES     | ... | YES     |
| NCS2 | YES     | NO      | ... | NO      |
| .    |         |         |     |         |
| .    |         |         |     |         |
| NCS8 | NO      | YES     | ... | NO      |

In this exemplary configuration, communication transmitted by any of the stations assigned to station group one (rooms 100–133, 201 and 202) will be directed to nurse control station one (NCS1) and to NCS2 so that staff members attending either nurse control station 2414 can respond to the call. Communications transmitted by any of the stations assigned to station group two (rooms 120–153, 201 and 202) will be directed to NCS1 and NCS8 so that staff members attending either nurse control station 2414 can respond to the call. Communications transmitted by any of the stations assigned to station group eight (rooms 154–187, 201 and 202) will be directed to NCS1 so that staff members attending NCS1 can respond to the call.

In the preferred embodiment, the patient care and communication system of the present invention can include four call assignment configurations. To illustrate, the call assignment configurations can be utilized to automatically (or manually) assign stations (2416 or 2418) to station groups and station groups to nurse control stations 2414 for day operation, for evening operation, for weekend operation and/or for holiday operation.

Figure 4:
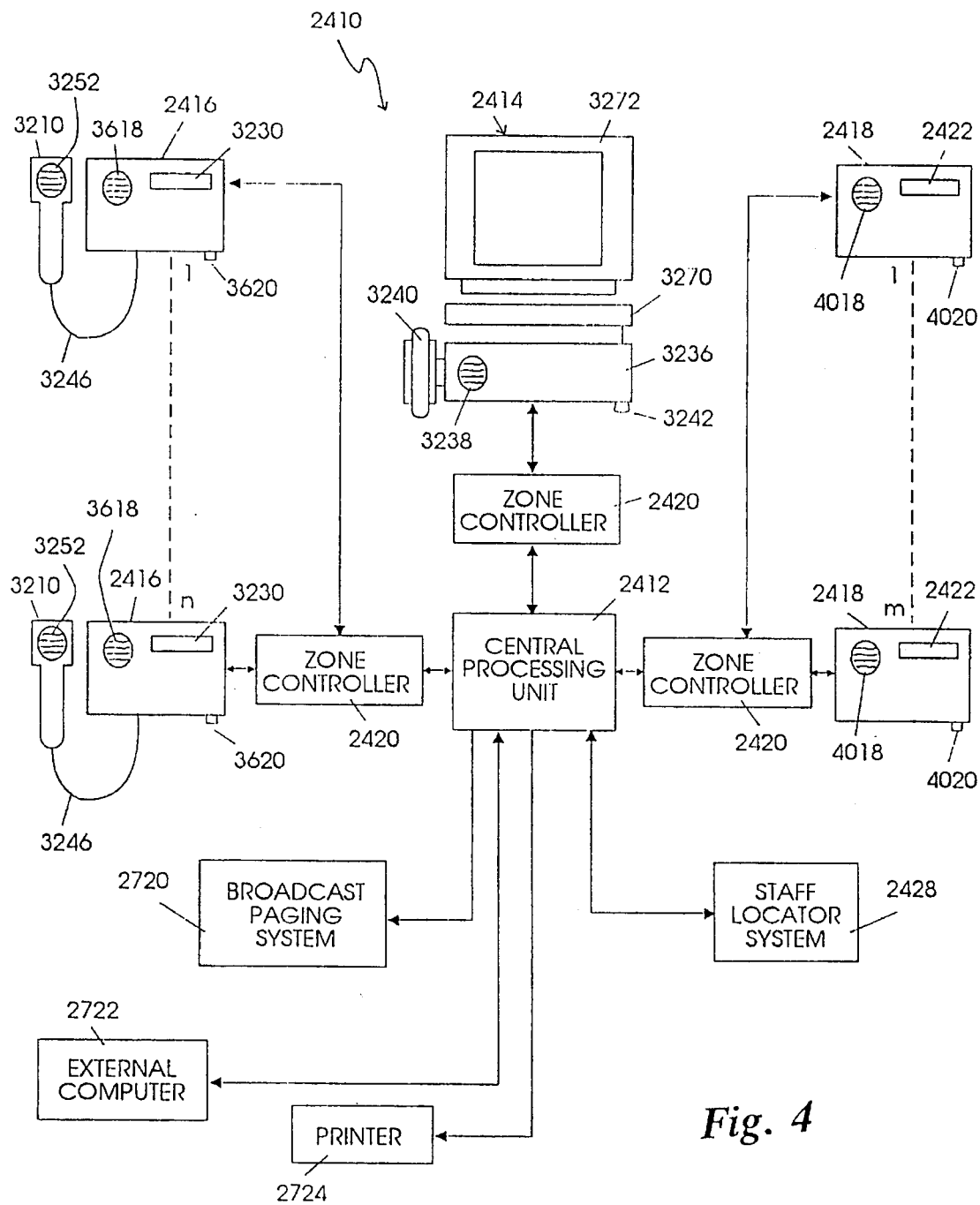
FIG. 4 is a functional block diagram of an another alternative embodiment of a system configuration of the present invention.

Referring now to FIG. 4 which illustrates an alternative system configuration in which, central processing unit 2412 is connected to external communication equipment such as broadcast paging system 2720, external computer 2722, printer 2724, and/or staff locator system 2428. Broadcast paging system 2720 may be utilized by the system of the present invention to locate staff members or other personnel who are not within the hospital or other health care facility. The broadcast paging system may be any known type capable of interfacing with a computer. Preferably, broadcast paging system 2720 and CPU 2412 communicate via serial communication ports connected to each device. Staff locator system 2428 may be provided to locate staff members anywhere in the hospital or other health care facility as described in U.S. application Ser. No. 07/924,101, filed Aug. 3, 1992, which is incorporated herein by reference. In addition to locating staff members, staff locator system 2428 may be utilized to track or locate patients in the hospital. To utilize the staff locator system to locate patients, each patient is provided with an identification badge or bracelet which includes the components as disclosed for identification badge worn by staff members and described above. The identification badge or bracelet continually transmits the identification signal of the patient and the central computer system continually monitors the identification signal to update the location of the bracelet and the patient. The location information of the staff member or patient is transferred to CPU 2412 via data link 2726 (shown in FIG. 4) which may be any known type of communication link utilized to facilitate communication between computer systems. External computer 2722 interfaces to CPU 2412 and performs computing functions including extracting or inputting data stored or otherwise processed within CPU 2412. Printer 2724 may be utilized to extract hard copies of data stored or otherwise processed within CPU 2412 including problem reports generated by the system, as will be described in more detail below.

Figure 2:
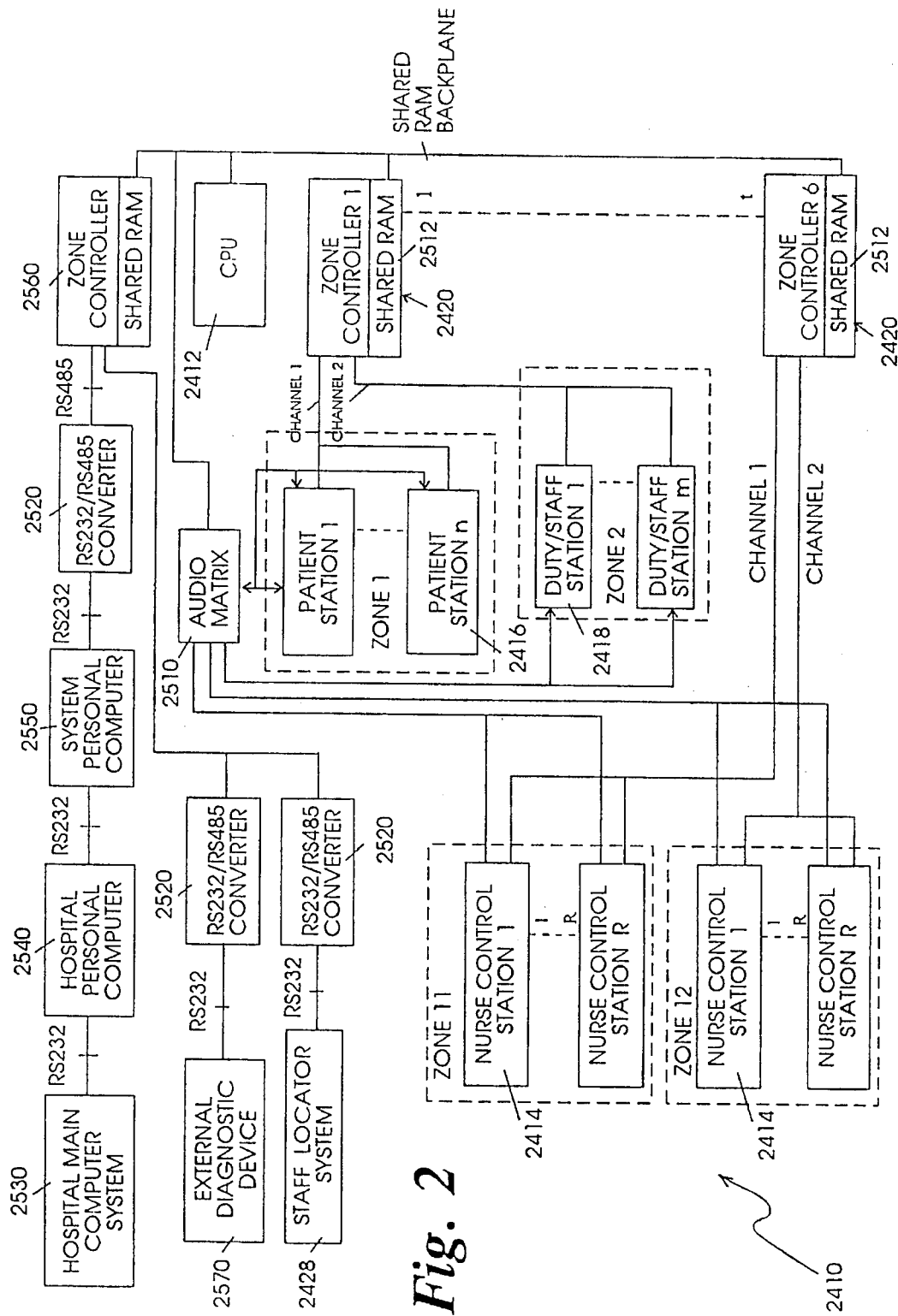
FIG. 2 is a functional block diagram of an alternative embodiment of a system configuration of the present invention.

FIG. 2 illustrates a functional block diagram of an alternative system configuration, which includes main hospital computer 2530 configured to interface with CPU 2412 to provide staff members with additional patient information, or to transfer from CPU 2412 to the main hospital computer patient information which may be utilized for billing purposes. For example, information pertaining to the types and quantities of prescription or intravenous drugs taken by the patient and the types of treatments received by the patient (e.g., X-rays or CT-scans), as well as the physician time spent with the patient, may be transferred to the main hospital computer to provide the hospital with more accurate billing information. Preferably, main hospital computer 2530 is interfaced with CPU 2412 via hospital personal computer 2540, system personal computer 2550, RS-232/RS-484 converter 2520 and zone controller 2560. In this configuration, the integrity of the main hospital computer is maintained and the serial conversion from RS-232 protocol to RS-484 protocol is accomplished.

Figure 5:
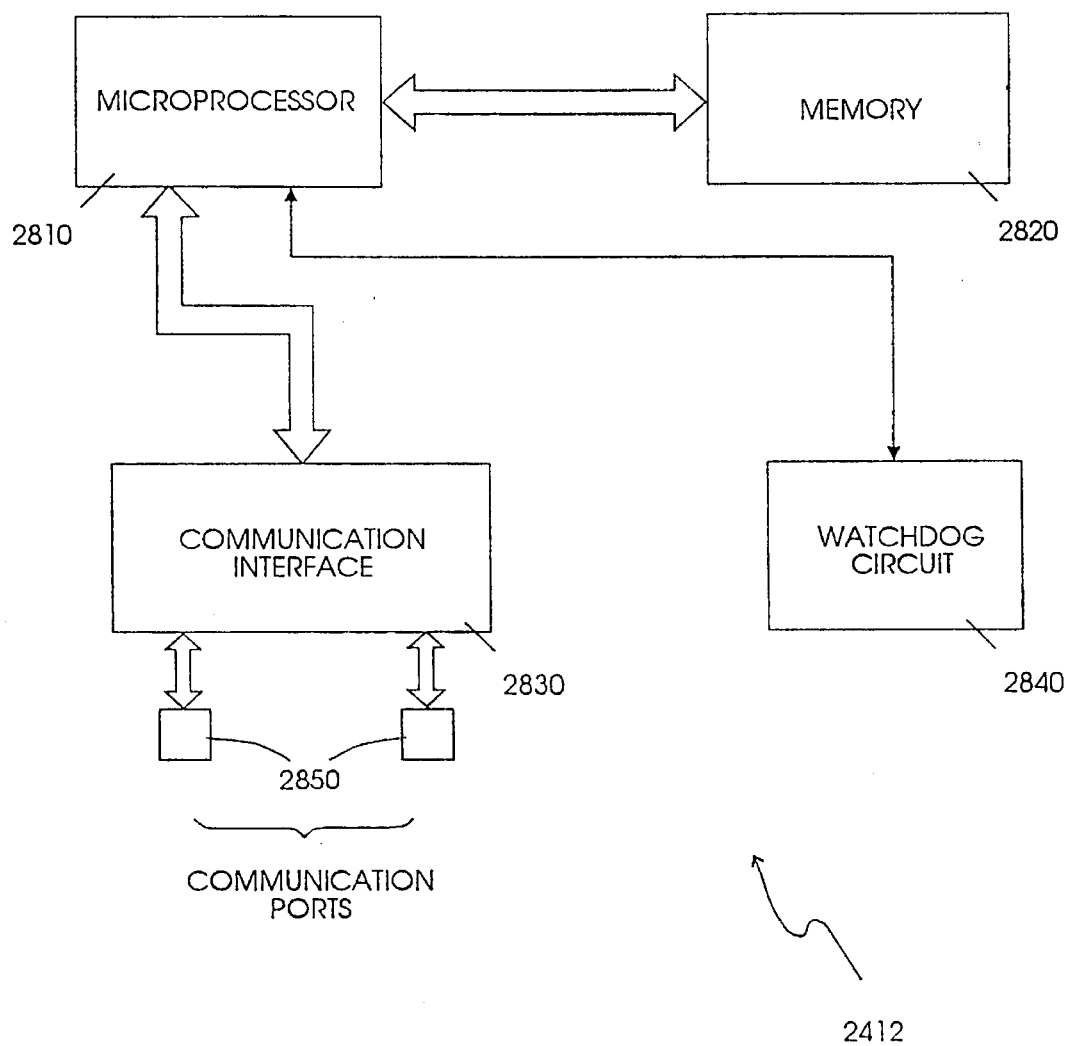
FIG. 5 is a circuit block diagram for the central processing unit illustrated in FIG. 1.

FIG. 5 illustrates the hardware components of central processing unit (CPU) 2412. The CPU 2412 includes microprocessor 2810, three Mbytes of memory 2820 (2 Mbytes of flash ROM and 1 Mbyte of RAM) having stored programs (e.g., operating system and application programs), and communication interface 2830. Preferably, microprocessor 2810 is an MC68000 16-bit microprocessor manufactured by Motorola Inc. In addition to the above circuits, CPU 2412 includes watchdog circuit 2840 which receives a one shot trigger from microprocessor 2810, at a predetermined time interval, preferably 300 msec., to ensure that the microprocessor is functioning. If, however, microprocessor 2810 fails to timely trigger watchdog circuit 2840, then the watchdog circuit will initiate an automatic reset of the microprocessor, thus preventing the microprocessor from locking-up for extended periods of time.

Communication interface 2830 and communication ports 2850 are provided to facilitate communication between CPU 2412 and zone controllers 2420 and between CPU 2412 and the external communication equipment. As noted above, the preferred communication protocol includes the RS-485 serial communication protocol. Accordingly, communication interface 2830 is configured to accommodate RS-485 communication utilizing RS-485 drivers/receivers which are known in the art.

Figure 6:
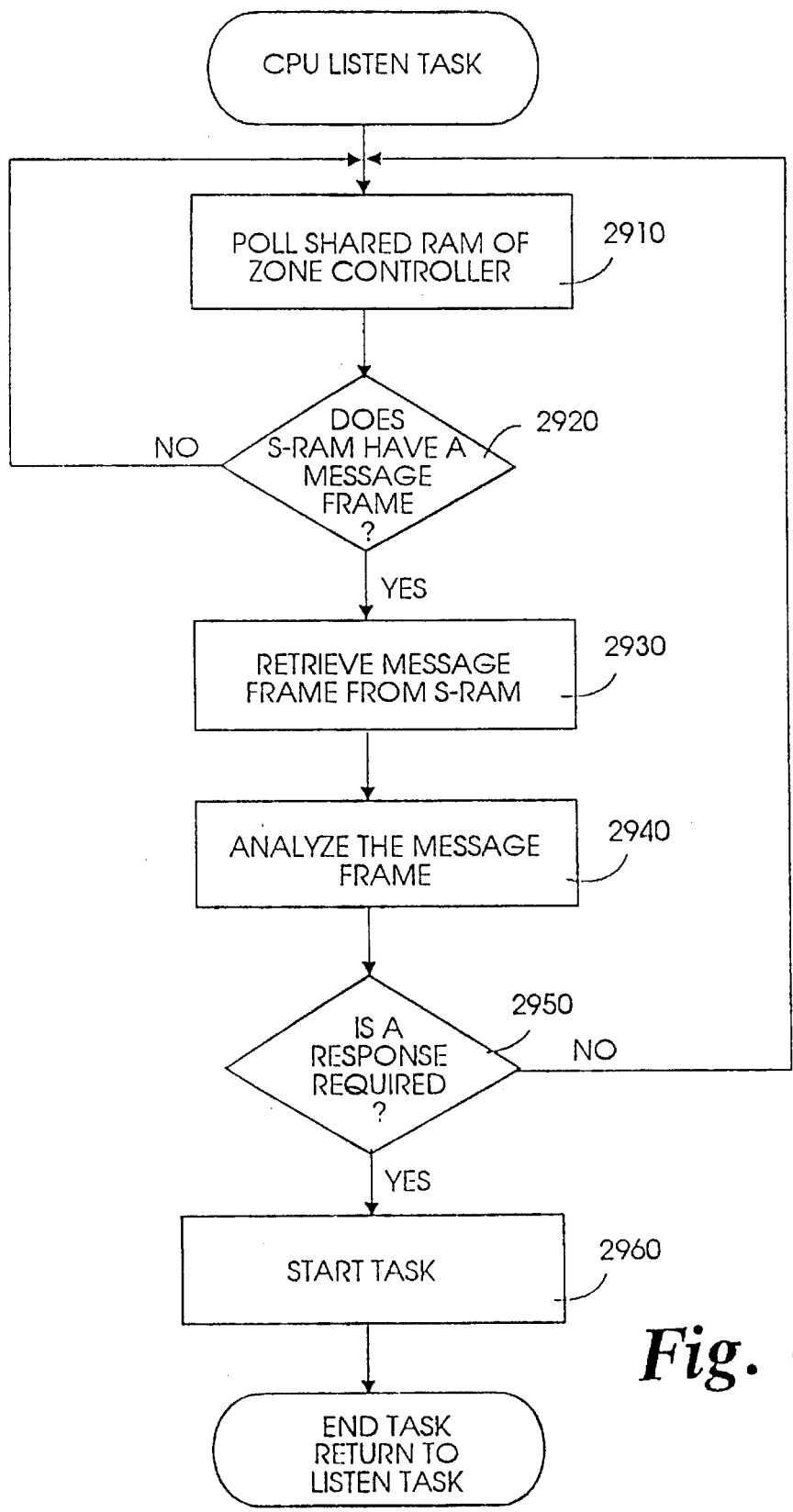
FIG. 6 is flow-chart diagram for the central processing unit illustrated in FIG. 1.

An exemplary operational flow of CPU 2412 is shown in FIG. 6. Initially, the CPU is in a listen mode. In the listen mode the CPU continuously polls or otherwise interrogates the different components attached thereto. For example, as shown in FIG. 6, the CPU will periodically poll each shared-RAM (S-RAM) 2512 (shown in FIG. 2) of each zone controller (step 2910) in a manner described hereinbelow. If the S-RAM does not have a message frame received from a station within the zone controller grouping, CPU 2412 returns and polls the next zone controller (step 2920). Preferably, as will be described in more detail below data transmitted between the CPU 2412 and the zone controller 2420 or between the zone controller 2420 and the stations (either 2414, 2416 or 2418) are in the form of message frames which include station identity information as well as the message data relating to a particular function.

If, however, the S-RAM does have a message frame stored therein, CPU 2412 will retrieve the message frame (step 2930) and analyze the received message frame by determining what patient station, staff station or nurse control station the message frame was received from and if the frame was received from a patient station, by organizing or obtaining any patient information associated with that particular patient station (step 2940). The DATA field within the INFORMATION field of the received message frame is then interpreted by the CPU, which determines whether a response to the associated patient station, staff station or nurse control station message frame is necessary (step 2950). If a response is not required, CPU 2412 returns to poll the next zone controller.

However, if a response is due, the CPU then starts the task associated with the information included in the message frame (step 2960). Upon completion of the task, CPU 2412 returns to the listen mode and begins polling the next zone controller connected thereto as described above.

The components of zone controller 2420 include a microcontroller, memory having stored programs (e.g., system or application programs) and a communication interface connected to communication ports. The connection of the zone controller 2420 components is the same as equivalent components of CPU 2412, as shown in FIG. 5. The zone controller 2420 also includes the shared-RAM (S-RAM) 2512, shown in FIG. 2, which is connected to the microcontroller. Preferably, the microcontroller is the 64180 microcontroller, manufactured by Motorola and the S-RAM includes 2 kilobytes of memory.

A communication interface and communication ports are provided to facilitate communication between zone controller 2420, CPU 2412 and slave devices, such as patient station 2416, staff station 2418 and/or nurse control station 2414. The communication protocol may be any known serial communication protocol, such as RS-232 or RS-485. The RS-485 protocol is preferred in the embodiment according to the present invention. Accordingly, the communication interface is configured to accommodate RS-485 communication utilizing RS-485 drivers/receivers which are known in the art. Each zone controller 2420 also includes a watchdog circuit which operates similarly to the watchdog circuit in CPU 2412. Thus, the watchdog circuit prevents the microcontroller from locking-up if the watchdog circuit is not polled at the predetermined time interval, preferably 300 msec., by the microcontroller.

The communication link between the zone controllers and stations or between the stations and peripheral equipment connected to the station is in a master-slave relationship. In the communication link between the zone controllers 2420 and the stations, the zone controllers are the master stations and the nurse control stations, patient stations or staff stations are the slave stations. Whereas, in the communication link between the stations and the peripheral equipment, the stations (e.g., the patient stations) are the master stations and the peripheral equipment is the slave. The master station is in control of the data link and transmits command frames to the slave stations. The master station maintains separate sessions (i.e., communication links) with each slave station attached to the link. To illustrate and again referring to FIG. 2, if zone controller 2420 is connected to a group of patient stations (1 to n) and/or connected to a group of staff stations (1 to m), the zone controller (master) will periodically poll each patient station (slave) to retrieve message frames. The slave station responds to the commands from the master station and can send one message to the master station per poll from the master station.

The master station may communicate with the slave stations in one of two logical states. One state is the INITIALIZATION state which is used to initialize the master/slave station (e.g., identify for each communication link which device connected thereto is the master and which is the slave). A second state is the INFORMATION TRANSFER state which permits the master and slave stations to transmit and receive control or application information transmitted across the data link between the master station and the slave stations in the form of message frames or blocks of data.

In the preferred embodiment, the message frames may be one of three types. The first type of message frame is the INFORMATION FORMAT frame (I-frame) which is used to transmit application information (e.g., message information associated with a particular function or station status data) between the master and slave stations. The I-frame may also acknowledge receipt of a frame from a transmitting station. The second type of message frame is the SUPERVISORY FORMAT frame (S-frame) which performs control functions, such as acknowledging the receipt of a poll from the master station or requesting the temporary suspension of the transmission of I-frames. The third type of message frame is the UNNUMBERED FORMAT frame (U-frame) which is also used for control purposes, such as performing data link initialization or tests.

As noted, the data (or information) transmitted between master and slave stations is preferably configured in the form of a message frame. The preferred message frame includes five fields, similar to the frame shown below:

ADDRESS/LENGTH/CONTROL/INFORMATION/FCS

Where, the ADDRESS field is one byte in length and identifies the patient station involved in the particular frame transaction (each station has a unique address which allows the CPU and zone controller to identify which station sent the frame); the LENGTH field is one byte in length and contains the size of the frame, in bytes, excluding the address and length fields; the CONTROL field includes the command and response information used to maintain data-flow accountability of the communication link between the zone controller (master) and the patient station (slave); and the INFORMATION field retains a predetermined number of bytes of data, preferably between 1 and 145 bytes, relating to the application data, such as, the data associated with the activation of the nurse call button (hereinafter "the nurse call data"). The frame-check-sequence (FCS) field, typically one byte in length, is used to check for transmission errors between the master and slave stations or devices.

The system of the present invention may transmit a predetermined number of message frames, preferably between 1 and 8 frames, before an acknowledgement or response to a transmitted frame is received. As a result, the CONTROL field is utilized to maintain data-flow accountability of the communication link, as noted above.

Shown in table III below is the CONTROL field bit encoding for the master and slave stations.

TABLE III

CONTROL field bit encoding (master station):

I-frame format:
:7:6:5:4:3:2:1:0:
 : x x : x x : 0
 : : : : : : : :-> Normally set to binary 0
 : : : : : : : :
 : : : : :-:-:---> N(S)
 : : : :
 : :-:-:---------> N(R)
 :
 :----------------> P CONTROL field bit encoding (slave station):

I-frame format:
:7:6:5:4:3:2:1:0:
 : x x : x x : 0
 : : : : : : : :-> Normally set to binary 0
 : : : : : : : :
 : : : : :-:-:---> N(S)
 : : : :
 : :-:-:---------> N(R)
 :
 :----------------> F The send sequence number N(S) (bits 1, 2 and 3) indicates the sequence number associated with a transmitted frame. Basically, the sequence number is a message counter which counts the number of message frames sent to a receiving station. The receive sequence number N(R) (bits 1, 2 and 3) indicates the next sequence number that is expected at the receiving station. The receive sequence number may also serve as an acknowledgement of the previous frame. In addition, the transmitting station maintains a send state variable V(S) which is the sequence number of the next message frame to be transmitted, and the receiving station maintains a receive state variable V(R), which contains the number that is expected to be in the sequence number of the next frame. The send state variable is incremented with each message frame transmitted and placed in the send sequence number N(s) field in the frame.

Upon receiving a frame, a receiving station checks for a transmission error by comparing the send sequence number with the receive state variable. If the frame is acceptable (i.e., the send sequence number and the receive state variable are equal), the receiving station increments the receive state variable V(R) and interpolates the variable into the receive sequence number field N(R) in the next outbound message frame. If, on the other hand, the send state variable V(S) does not match the receive sequence number N(R) in the message frame, the receiving station decrements the send state variable V(S) and retransmits the last message frame when the next frame has to be transmitted.

To establish an interactive communication link between stations, the master station uses the poll bit (P) to solicit a status response (e.g., an S-frame) or an I-frame from a slave station. Generally, the slave station does not transmit a frame to a master station until a message frame with an active poll bit (i.e., P is set to logic 1) is received from the master frame. In the preferred embodiment, the polling rate of the master station is aperiodic or not fixed. The polling rate is dependent upon a number of factors such as the baud rate and the type of message frame being sent by the slave station. For example, if the baud rate is 9600 and if all the slave stations respond to a poll by the master station with an S-frame, the polling rate is approximately 20 msec. However, if a slave station responds with an I-frame which includes 64 bytes of display data the rate (or time) before the master station will poll the next slave station is approximately 64 msec. Generally, at 9600 baud, one byte of data is transferred in one millisecond.

The slave station responds to an active poll bit with an I-frame or S-frame format message frame. In the preferred embodiment, the slave station has 15 msec. to start transmitting the responding message frame and 150 msec. to complete transmission of the frame which is identified by activating the Final bit (F) (i.e., F is set to a logic 1).

If the slave station fails to successfully respond to the polling frame of the master station with either an S-frame or I-frame, for a predetermined number of polls, preferably 10, that particular station will be marked as disconnected and will be polled at slower rate (preferably, about every 10 sec.) until the master station receives at least one message frame from that particular slave station. When a station or other equipment connected to the system of the present invention are determined to be disconnected, the identity of the station or other equipment and the room location of the equipment are stored in a problem report which can be printed on hard or soft copy via printer 2724 and/or external computer 2722, shown in FIG. 4. Alternatively, the problem report can be displayed on nurse control station display 3272 shown in FIG. 32 upon the proper keying of direct select keys 3374 of nurse control station display 3272 pursuant to menu prompts.

Referring now to Table IV below, the CONTROL field encoding for the commands and responses used by an S-frame are shown:

TABLE IV

CONTROL field bit encoding (master station):

S-frame format:
:7:6:5:4:3:2:1:0:
: x x : : : 0 1
: : : : : : : :->Normally set to binary 1
: : : : : : : :
: : : : :-:----->Commands:
: : : : :-:-----> Binary 0 - Receive Ready (RR)
: : : : :-:-----> Binary 1 - Receive Not Ready (RNR)
: : : :
: :-:-:--------->N(R)
:
:--------------->Poll bit (P)

CONTROL field bit encoding (slave station):

S-format:
:7:6:5:4:3:2:1:0:
: : : : : : 0 1
: : : : : : :-:->Normally set to binary 1
: : : : : : : :
: : : : :-:----->Commands:
: : : : :-:-----> Binary 0 - Receive Ready (RR)
: : : : :-:-----> Binary 1 - Receive Not Ready (RNR)
: : : :
: :-:-:--------->N(R)
:
:--------------->Final bit (F)

The receive ready (RR) command is used by either the master or the slave station to indicate that it is ready to receive an I-frame and/or acknowledge previously received frames by using the receive sequence number. If a station had previously indicated that it was busy by using the receive not ready (RNR) command, the station then uses the RR command to indicate that it is now free to receive data (e.g., an I-frame).

As noted, receive not ready (RNR) is used by a receiving station to indicate a busy condition in response to polling by a master station. This notifies the transmitting station that the receiving station is unable to accept I-frames. The RNR command may also be utilized to acknowledge a previously transmitted frame by using the receive sequence number.

The commands and responses used by a U-frame are shown below in Table V:

TABLE V

CONTROL field encoding (master station)

U-frame format:
:7:6:5:4:3:2:1:0:
: : : : : : 1 1
: : : : : : :-:->Normally set to binary 3
: : : : : : : :
: :-:-:-:-:----->Commands:
: :-:-:-:-:-----> 0 - Set Init. Mode (SIM)
: :-:-:-:-:-----> 1 - Reset Init. Mode (RIM)
: :-:-:-:-:-----> 2 - Test Message (TM)
: :-:-:-:-:-----> 3 - Loop Back (LB)
: :-:-:-:-:-----> 4 - Broadcast (BC)
:
:--------------->Poll bit (P)

CONTROL field encoding (slave station)

U-format:
:7:6:5:4:3:2:1:0:
1 : : : : : 1 1
: : : : : : :-:->Normally set to binary 3
: : : : : : : :
: :-:-:-:-:----->Commands:
: :-:-:-:-:-----> 0 - Set Init. Mode (SIM)
: :-:-:-:-:-----> 1 - Reset Init. Mode (RIM)
: :-:-:-:-:-----> 2 - Test Message (TM)
: :-:-:-:-:-----> 3 - Loop Back (LB)
:
:--------------->Final bit (F)

The set initialization mode (SIM) is used by a master or slave station to initialize the master/slave session (or communication link). The SIM command puts the master and slave stations in the initialization state. Upon receiving the SIM command, the receiving station clears the send state variable number V(S) and the receive state variable V(R), thus clearing a retransmit buffer (not shown). The SIM command is used by a station on power-up or to clear a lock-up condition of the station. The reset initialization mode (RIM) is used by a master or slave station to set an information transfer state. This command also serves as an acknowledgement of the SIM command.

The test message (TM) command is used to test data lines. The receiving station responds with a LB command which carries (or echoes back) the same data received from the message frame where the TM command was active. Failure of a slave station to echo back the same data received in the message frame causes the master station to identify the station as disconnected and the station identity and location are added to the problem report.

The broadcast (BC) command (bits 2–6) is used by a master station to transmit data to all slave stations. The master station sends this command while the P bit is set to a logic zero and the address field of the message frame, noted above, contains "FF" hex.

The bit encoding for the INFORMATION field of the message frame noted above will now be described. Preferably, the INFORMATION field consists of four fields which identify the priority level of the message frame, the station ID, the type of message and data to augment the message type:

PATH/RSP_ID:REQ_ID/DATA/O

The PATH field, shown below in Table VI, may be four bytes in length and contains routing information and frame transition priority data. The transition priority data identifies to the CPU the priority level associated with the received I-frame. As a result, the system of the present invention can prioritize incoming message frames so as to organize staff responses thereto in order of priority, as will be described in more detail below. The last byte of this field preferably includes an address expansion bit which when set to logic one identifies that the next byte of data is the station address field which identifies which slave station is sending the message frame.

TABLE VI

```
PATH field bit encoding:
:7:6:5:4:3:2:1:0:
: : : : : : : :
: : : :-:-:-:-:-> Station Address
: : :
: :-:-----------> Priority: binary 2 - alarm,
                            binary 1 - event/control,
: :-:----------->          binary 0 - data type
:
:---------------> Address expansion set to logic 1 = next byte
                  is station address
```

The RSP_ID:REQ_ID field, shown below in Table VII, contains response/request tag (ID) data. Upon receiving a request message (type bit is set to logic 1), the slave station sends a specific response message (e.g., an I-frame). If there is no specific response, the slave station sends generic acknowledgement typically in the form of an S-frame.

TABLE VII

```
RSP_ID:REQ_ID field bit encoding:
:7:6:5:4:3:2:1:0:
: : : : : : : :
: : : :-:-:-:-:-> response/request ID
: :
: :-------------> local master: binary 1 = local master
                                          request/response
:
:---------------> type: logic 1 = request, logic 0 = response
```

Generally, the DATA field may be 128 bytes in length and contain application specific data and preferably, consists of three fields:

LENGTH/DTYPE/TEXT

Where, the LENGTH field, typically 1 byte in length, contains the size in bytes of the DTYPE and TEXT fields; the DTYPE field, typically one byte in length, contains data codes such as the type of message being sent, e.g., code blue; and the TEXT field which may be 126 bytes in length, contains application specific data, e.g., message data associated with a particular function or station status data, which is utilized to augment the DTYPE field by identifying a textual message associated with the particular function identified in the DTYPE field. For example, if the DTYPE field identifies a "code blue" code, the TEXT field will include the text which should be displayed on other stations, such as the staff station.

Figure 7:
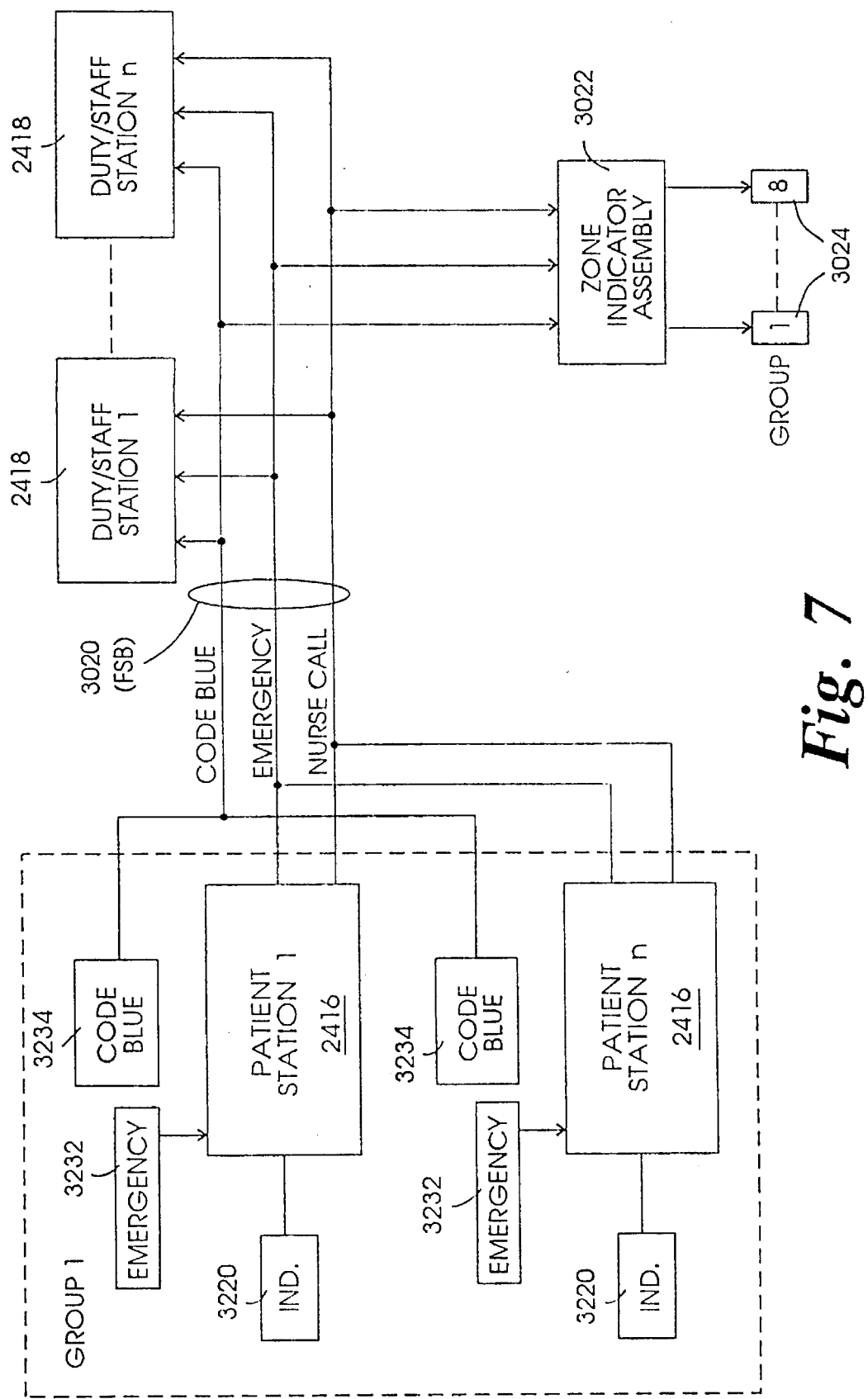
FIG. 7 is a block diagram for the fail safe feature associated with the system of the present invention.

In the event of a failure within the CPU 2412, the system of the present invention also provides a fail safe feature which is activated upon detection by the nurse control stations 2414, the patient stations 2416 and/or staff stations 2418. An exemplary embodiment of the configuration for fail safe operation is shown in FIG. 7. In this configuration, fail safe bus (FSB) 3020 is connected between each patient station 2416, each corresponding staff station 2418 and zone indicator assembly 3022. If a failure occurs in the CPU 2412, each patient station 2416 and corresponding staff station 2418 will fail to receive a polling signal from their corresponding zone controllers. As a result, each station will operate in a local mode utilizing the fail safe bus. When in the local mode, activation of any of the functions which have access to the fail safe bus will cause a response at a particular patient station, the staff stations and at the zone indicator assembly connected to the group, to allow staff members in the vicinity of the station utilizing the fail safe bus to respond.

Figure 8:
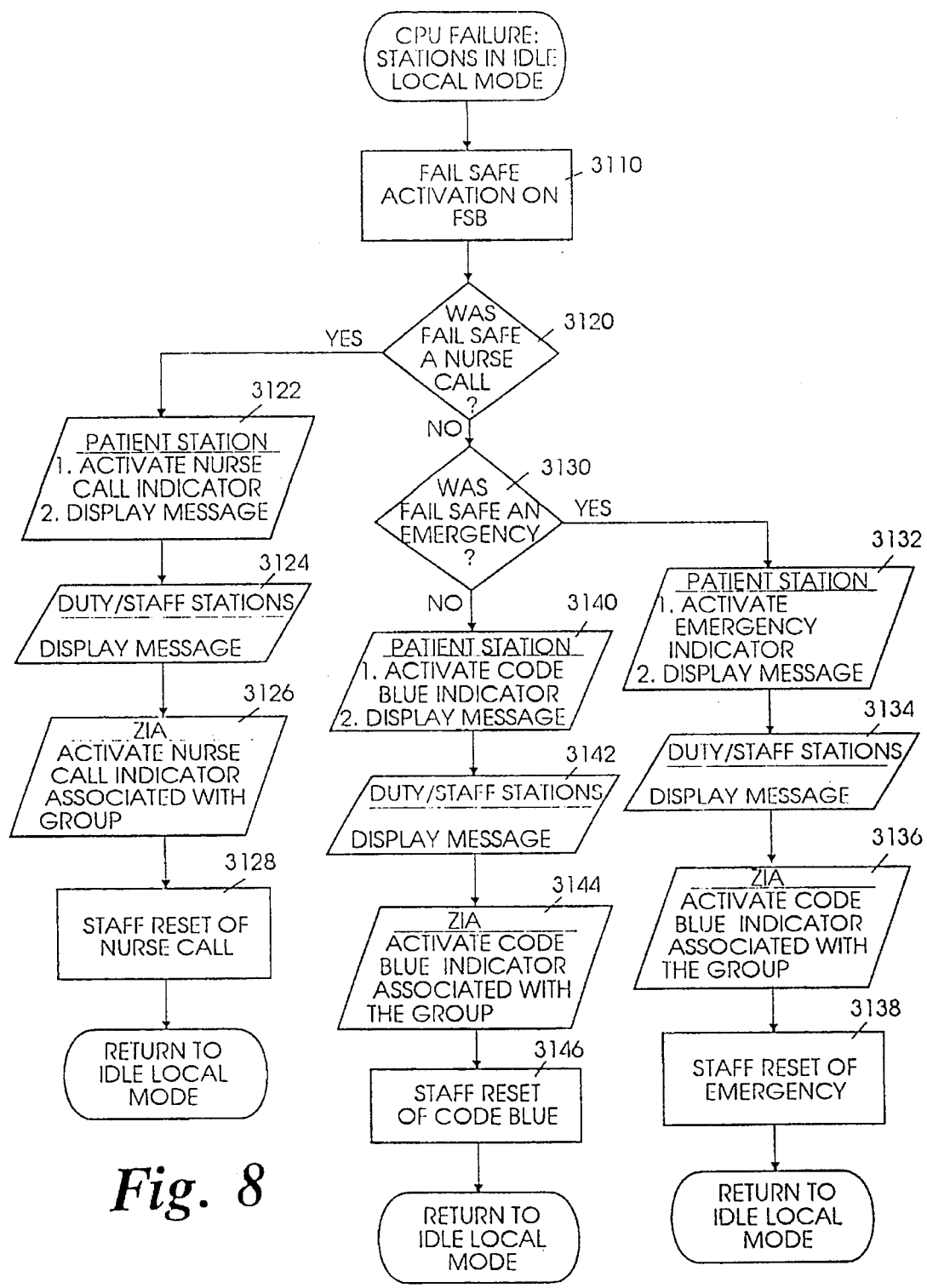
FIG. 8 is a flow-chart diagram of the fail safe feature illustrated in FIG. 7.

An operational flow associated with the above described exemplary fail safe feature will be described with reference to FIGS. 7–9. As noted, upon failure of the CPU 2412, the stations associated with the system of the present invention operate in the local mode. In response to activation of a fail safe device (e.g., the nurse call button 3250, the code blue switch 3234 or the emergency switch 3232) the system first determines whether the cause of the fail safe was from the activation of nurse call button 3250 of patient control unit 3210 (shown in FIG. 9) (steps 3110 and 3120). Nurse call button 3250, code blue switch 3234 and/or emergency switch 3232 are connected to patient station 2416 and provide either a general indication to staff members that the patient needs assistance or an emergency indication relating to the patients immediate health condition. Nurse call button 3250 allows the patient to indicate the need for general assistance, whereas, code blue switch 3234 and emergency switch 3232 allow staff members to activate the appropriate staff response to the patient's health condition. For example, if the patient is experiencing a heart attack a staff member would activate the code blue switch.

If the cause of the fail safe was due to the activation of nurse call button 3250, the patient station responds by activating nurse call indicator 3222 of indicator assembly 3220 associated with that particular patient station and by displaying a "nurse call" message on patient station display 3230 (step 3122). Next, the staff stations 2418 (shown in FIG. 1) associated with the group of patient stations 2416 respond by displaying a "nurse call" message on staff station display 2422 (step 3124). Zone indicator assembly (ZIA) 3022 activates the nurse call indicator of zone indicator 3024 (e.g., indicators 1 through 8, shown in FIG. 7) associated with the particular group of patient stations (step 3126). For example, if the nurse call button is activated by a patient station associated with group 1, the nurse call indicator of the group 1 zone indicator 3024 associated with zone indicator assembly 3022 will be activated. Manual reset of the patient station by a staff member responding to the call returns the FSB and the patient stations to the idle local mode (step 3128).

If the cause of the fail safe was not from the activation of the nurse call button, the fail safe system then determines if the fail safe was caused by the activation of emergency switch 3232 (step 3130). If fail safe operation was caused by the activation of emergency switch 3232, patient station 2416 responds by activating the emergency indicator associated with that patient station and by displaying an "emergency" message on patient station display 3230 (step 3132). Preferably, the emergency indicator is the same indicator as nurse call indicator 3222. However, activation of indicator 3222 in the emergency mode results in a blink light at a predetermined rate in pulses per minutes (PPM) as illustrated in the table of FIG. 19. Whereas, activation of indicator 3222 in the nurse call mode results in a steady lamp intensity. Second, staff station or stations 2418 associated with the subject patient station, displays an "emergency" message on staff station display 2422, shown in FIG. 1 (step 3134). Next, zone indicator assembly 3022 activates the emergency indicator of zone indicator 3024 associated with the group with which the particular patient station belongs (step 3136). Staff members responding to the emergency call, manually reset emergency switch 3232 (step 3138), thus returning the fail safe system to the idle local mode.

If, on the other hand, the cause of the fail safe was not from the activation of an emergency switch, then, according to this exemplary embodiment, the fail safe operation was activated by code blue switch 3234. The patient station responds to the code blue call by activating code blue indicator 3228 associated with patient station 2416 to which the code blue switch is operatively connected, and by displaying a "code blue" message on patient station display 3230 (step 3140). Secondly, staff station or stations 2418 associated with the group of patient stations 2416, displays a "code blue" message on station display 2422 (step 3142). Zone indicator assembly 3022 also activates the code blue indicator associated with the subject patient station group number (step 3144). Manual reset of code blue switch 3234 by the responding staff members returns the fail safe bus to the idle local mode (step 3146).

NURSE CONTROL STATION

The nurse control portion of the present invention will now be described with reference to FIGS. 9 and 10. FIG. 9 illustrates a system configuration in which peripheral equipment is connected to patient station 2416 and in which nurse control station 2414 includes main processor 3270, keyboard 3236 and nurse control station display 3272. Nurse control station display 3272 can be user programmed to perform functions, such as initiating a code blue operational sequence, either through keyboard 3236 or direct select keys 3274. The direct select keys 3274 allow staff members to select specific functions in response to menu driven prompts.

Figure 10:
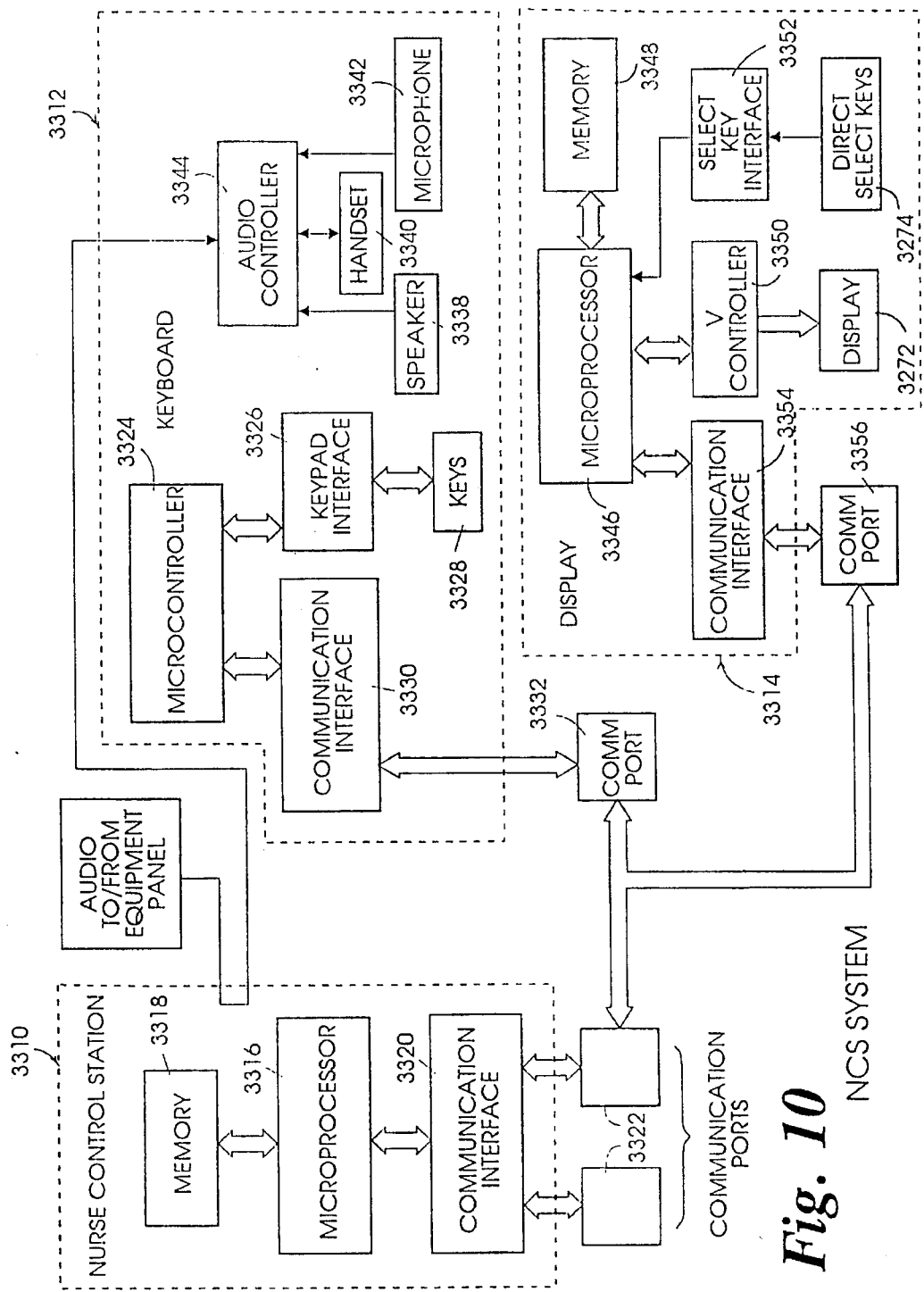
FIG. 10 is a block diagram for the nurse control station illustrated in FIG. 1.

FIG. 10 is a block diagram which illustrates hardware components for nurse control station 2414. Nurse control station 2414 includes main processor circuitry 3310, keyboard circuitry 3312 and display circuitry 3314. Main processor circuitry 3310 includes microprocessor 3316, such as the 16 bit model 286 microprocessor manufactured by Chips & Technology, Inc., 2 Mbytes of memory 3318 having stored programs (e.g., system and application programs) and communication interface 3320 connected to communication ports 3322.

Preferably, communication interface 3320 and communication ports 3322 are provided to facilitate data communication between zone controller 2420, CPU 2412 and the nurse control station 2414. As noted above, the preferred communication protocol includes the RS-485 serial communication protocol. Accordingly, communication interface 3320 is configured to accommodate RS-485 communication utilizing RS-485 drivers/receivers which are known in the art.

Keyboard circuitry 3312 includes microcontroller 3324, such as model 8052 manufactured by Intel, which includes internal memory having, preferably, 4 Kbytes of ROM and 256 bytes of RAM, keypad interface 3326 which is connected to keys 3328 and facilitates communication between a staff member and the nurse control station. Communication interface 3330 and communication port 3332 are provided as a data communication link to main processor circuitry 3310. AS noted, the preferred communication protocol includes the RS-485 serial communication protocol. Accordingly, communication interface 3330 is configured to accommodate RS-485 utilizing RS-485 drivers/receivers which are known in the art.

Figure 11:
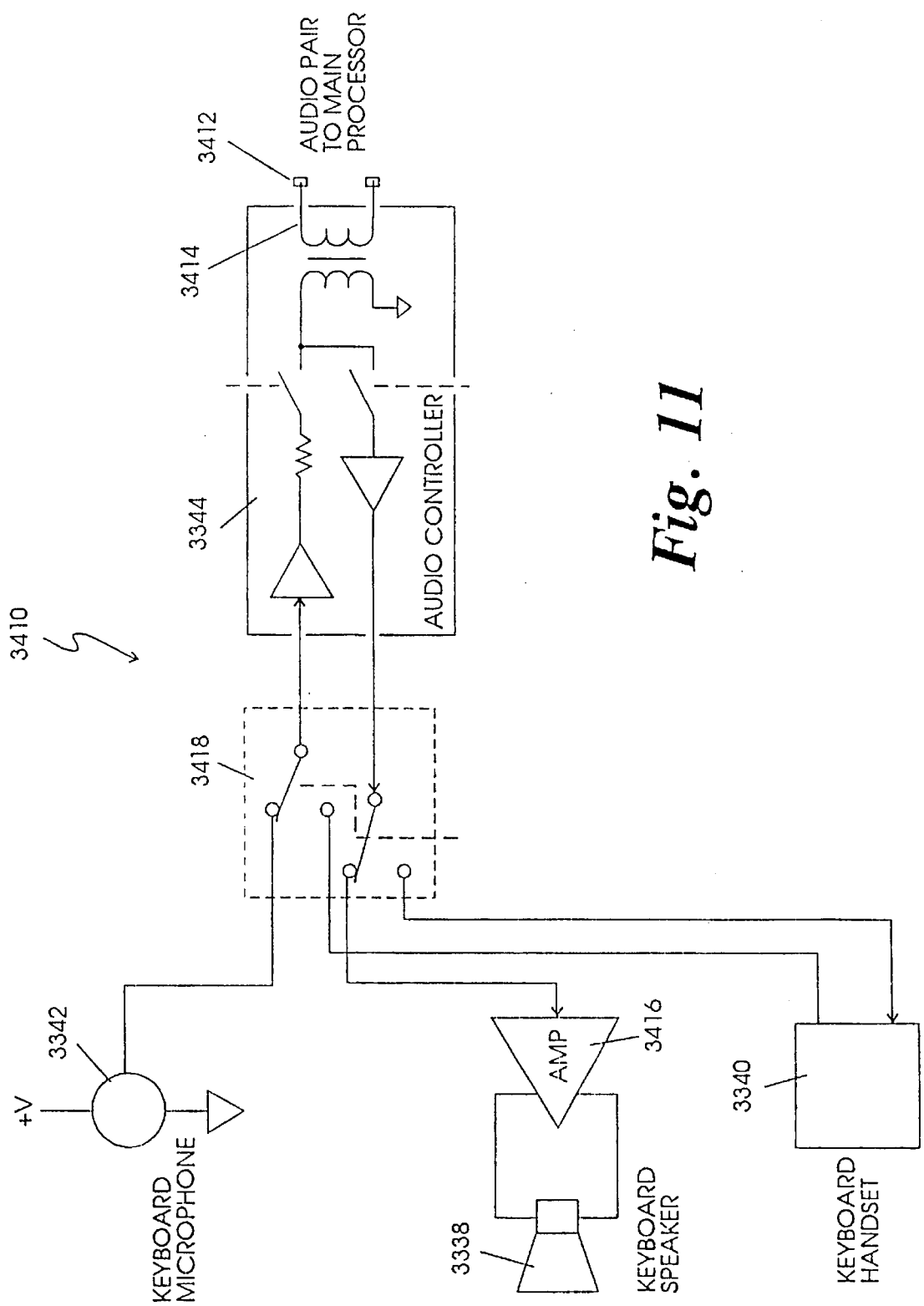
FIG. 11 is a circuit block diagram for the audio circuitry of the keyboard of the nurse control station illustrated in FIG. 1.

Keyboard 3236 (shown in FIG. 9) includes speaker 3338, handset 3340 and microphone 3342 which facilitate audio communication between nurse control station 2414, patient stations 2416 and/or staff stations 2418, via audio controller 3344. The audio circuit portion 3410 of nurse control station 2414 will now be described with reference to FIG. 11, which illustrates the hardware configuration for the audio portion of the keyboard. As shown, audio pair 412 from main processor 3270 of nurse control station 2414 (shown in FIG. 9) is connected to the front end of audio controller 3344. Preferably, the front end of audio controller 3344 includes a coupled 600 ohm balanced transformer 3414 which isolates the internal audio circuitry of nurse control station 2414 from the external audio circuits. Depending upon whether the audio signal is being received or transmitted, the back end of audio controller 3344 either directs the audio signal to keyboard speaker 3338 or to handset 3340, or directs the audio signal from microphone 3342 to transformer 3414.

Preferably, audio controller 3344 is a 34118 audio controller manufactured by Motorola. Audio input signals from main processor 3270 of nurse control station 2414, which pass through the audio controller are directed to keyboard speaker 3338 via amplifier 3416 or to handset 3340 via relay controller 3418 controlled by microcontroller 3324 (shown in FIG. 10). Audio generated by the nurse control station via microphone 3342 or handset 3340 is transferred through relay controller 3418 to audio controller 3344 and onto the audio pair as shown. The audio pair from keyboard circuitry 3312 is directed to the equipment panel via main processor circuitry 3310, as shown in FIG. 10.

Display circuitry 3314 includes microprocessor 3346, such as model 8051 manufactured by Intel, memory 3348 having stored programs (e.g., system and application programs), video controller 3350 which is connected to nurse control station display 3272 and facilitates the display of the visual communication signals. Select key interface 3352 is connected to direct select keys 3274 and is provided to identify to microprocessor 3346 which direct select key 3274 has been depressed. Communication interface 3354 and communication port 3356 are provided as a data communication link to main processor circuitry 3310. As noted, the preferred communication protocol includes the RS-485 serial communication protocol. Accordingly, communication interface 3354 is configured to accommodate RS-485 communication utilizing RS-485 drivers/receivers which are known in the art.

PATIENT STATION

The patient station portion of the present invention will now be described with reference to FIGS. 4, 9 and 12, 13, 14A and 14B. Turning initially to FIG. 9, patient station 2416 is a microprocessor controlled interface between CPU 2412, the patient bedside equipment and peripheral equipment. The communication link between CPU 2412 and the bedside or peripheral equipment is via the master/slave communication link described above. Examples of the patient bedside equipment include heart monitors, respirators, pulse oxymeters or I.V. pumps which include data communication ports to serially transmit data. Examples of peripheral equipment include patient control unit 3210, staff presence switch 3254, indicator assembly 3220, code blue switch 3234, emergency code switch 3232 and/or a smoke detector (not shown). Staff presence switch 3254 is preferably located by the door of the patient rooms and is provided to activate indicator 3220 and to cause patient station 2416 to send a message frame to CPU 2412 indicating the particular type of staff member who is present in the patient's room, as will be described in more detail below. In addition, patient station 2416 may be operatively connected to a side-rail communication system (not shown) installed in a side-rail of the patient's bed, as well as bed sensors which sense whether the patient is in the bed. Side-rail communication system may be connected to the audio output ports 3624, shown in FIG. 13, to facilitate audio communication at the side-rail.

Figure 12:
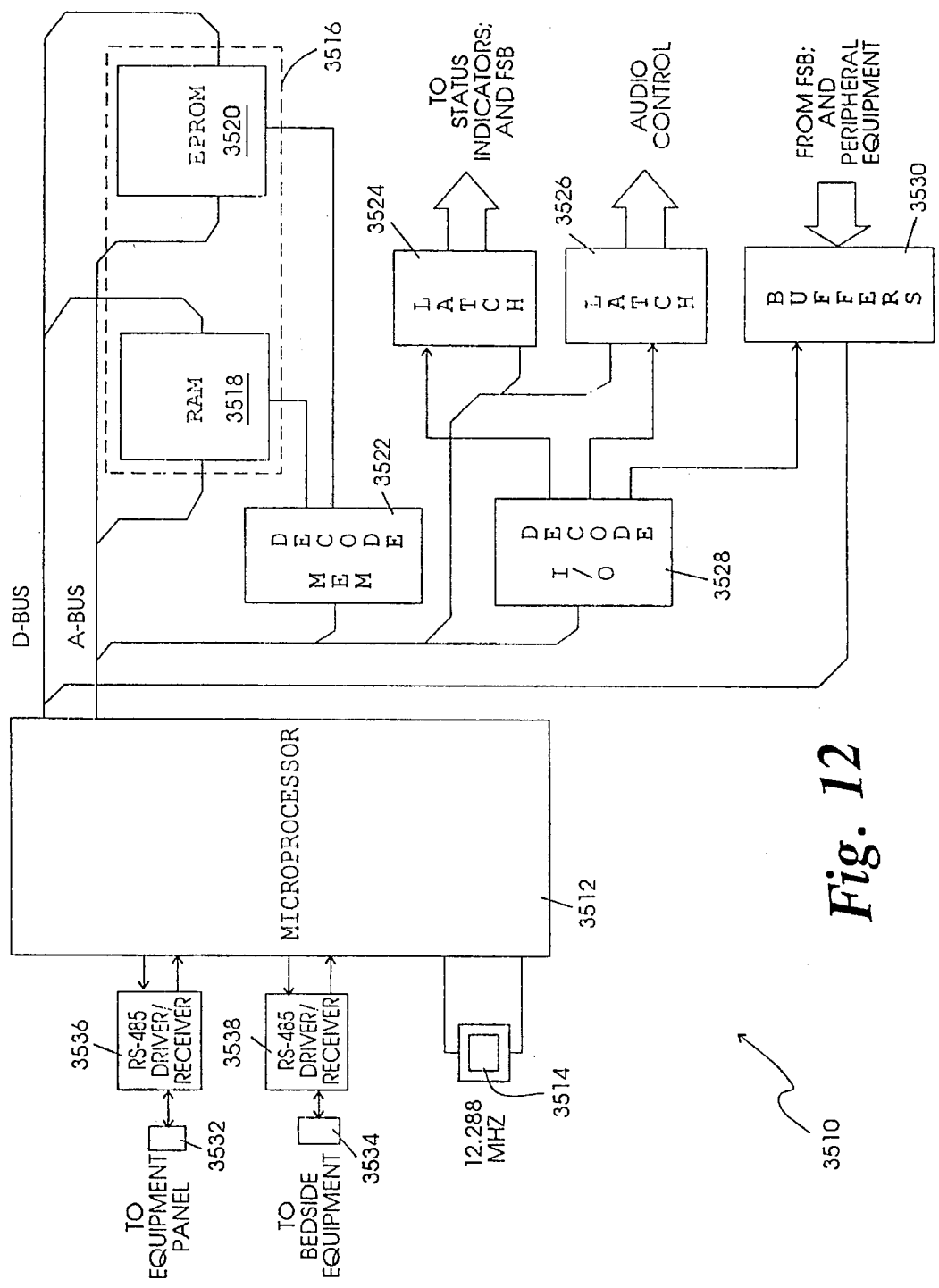
FIGS. 12 and 13 are circuit block diagrams for the internal circuitry for the patient stations illustrated in FIG. 1.

FIG. 12 is a circuit block diagram for the patient station circuitry 3510 installed within patient station 2416. The patient station circuitry 3510 includes microprocessor 3512, such as model 64180 manufactured by Motorola operating at a frequency of 12,888 MHz. via crystal 3514, 96 Kbytes of memory 3516 (e.g., 64 Kbytes of flash ROM and 32 Kbytes of RAM) having stored programs, e.g., system and application programs. In this exemplary configuration, the data and address buses of the microprocessor are connected to memory, e.g., RAM 3518 and an EPROM 3520. Memory decoder 3522 is utilized to select between RAM 3518 and EPROM 3520 in response to a particular address on the address bus. The address bus is also connected to a pair of latches 3524 and 3526 which interface the microprocessor to status indicators, the fail safe bus (FSB), the audio control circuitry, and to switches and other peripheral equipment connected to the patient station, as shown. In addition, I/O decoder 3528 is utilized to select between either latch in response to a particular address on the address bus. Incoming signals from the above noted peripheral equipment are received by buffer 3530 and then transferred to the data-bus upon being enabled by I/O decoder 3528.

Utilizing the preferred microprocessor 3512 (i.e., the Motorola 64180), serial communication between the zone controller 2420 and microprocessor 3512 or between the bedside equipment and microprocessor 3512, may be accomplished through either one of two asynchronous serial communication ports 3532 and 3534 which are, preferably, configured to RS-485 protocol utilizing RS-485 driver/receivers (RS-485 D/R) 3536 and 3538 as shown.

Figure 13:
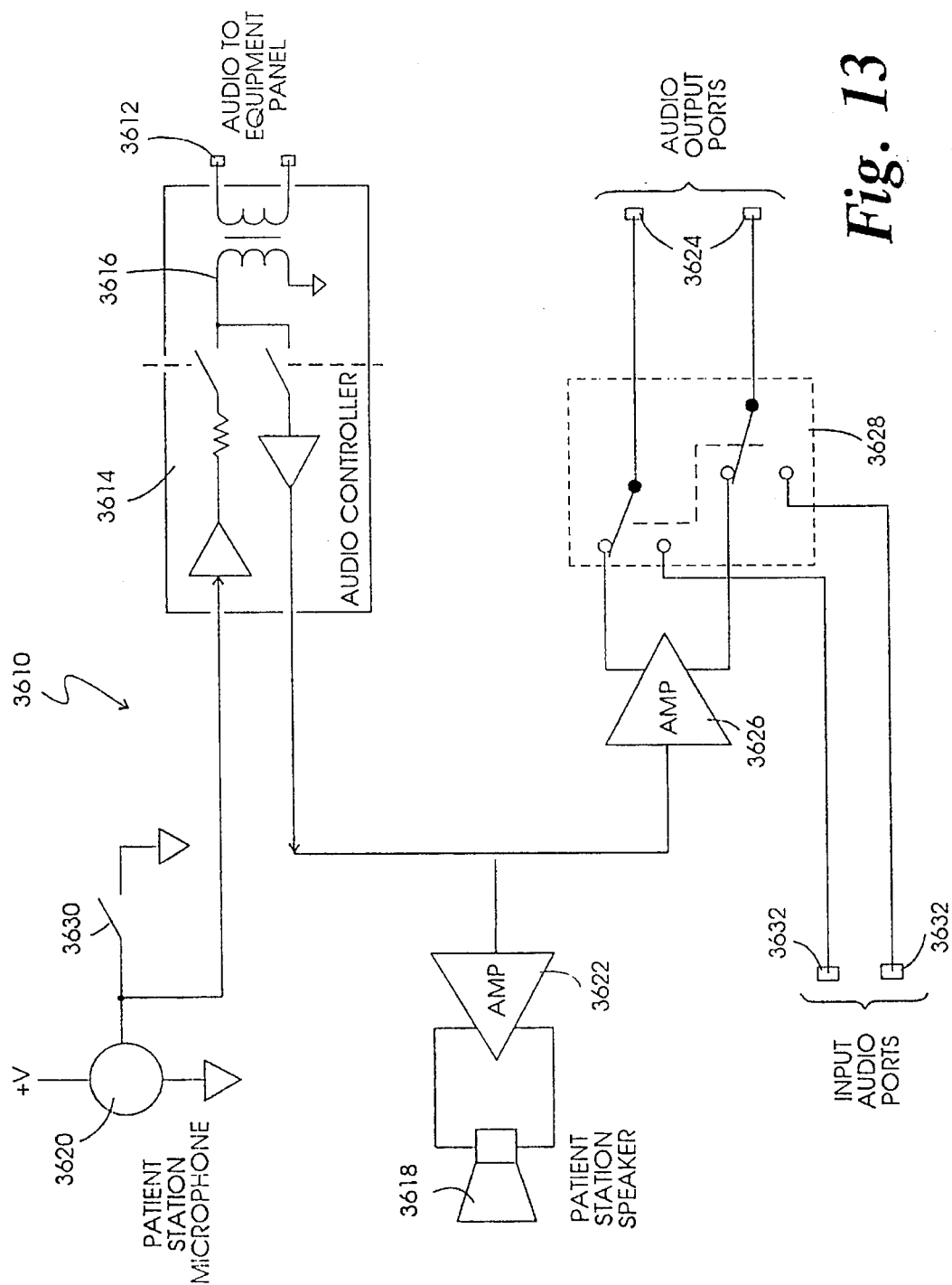

FIG. 13 is a circuit block diagram for the audio portion 3610 of patient station 2416. As shown, audio pair 3612 from an equipment panel (e.g., audio matrix 2510 shown in FIG. 2) is connected to the front end of audio controller 3614. Preferably, the front end of audio controller 3614 includes a coupled 600 ohm balanced transformer 3616 which isolates the internal audio circuitry of patient station 2416 from the external audio circuits. Depending upon whether the audio signal is being received or transmitted, the back end of audio controller 3614 either directs the audio signal to patient station speaker 3618 or to an external audio speaker, such as speaker 3252 of patient control unit 3210, shown in FIG. 9, or directs the audio signal from microphone 3620 to transformer 3616.

Preferably, audio controller 3614 is a 34118 audio controller manufactured by Motorola. Audio input signals from audio matrix 2510 which pass through the audio controller are directed to patient station speaker 3618 via amplifier 3622 and/or to audio output ports 3624 via amplifier 3626 and relay controller 3628. Audio signals generated by the patient station via microphone 3620 are selectively transferred through audio controller 3614 onto the audio pair as shown. Mute switch 3630 may be provided to allow a staff member to manually short out the microphone so as to prevent audio signals from being generated at the patient station. In addition, the audio circuitry for the patient station may include input audio ports 3632 which facilitate a connection between external entertainment equipment, such as a television or a radio, and audio output ports 3624 via relay switch 3628. To illustrate, audio signals from a television in the patient's room can be directed from patient station 2416 to speaker 3252 in patient control unit 3210 (shown in FIG. 9) to bring the audio from the television closer to the patient.

Figure 14A:
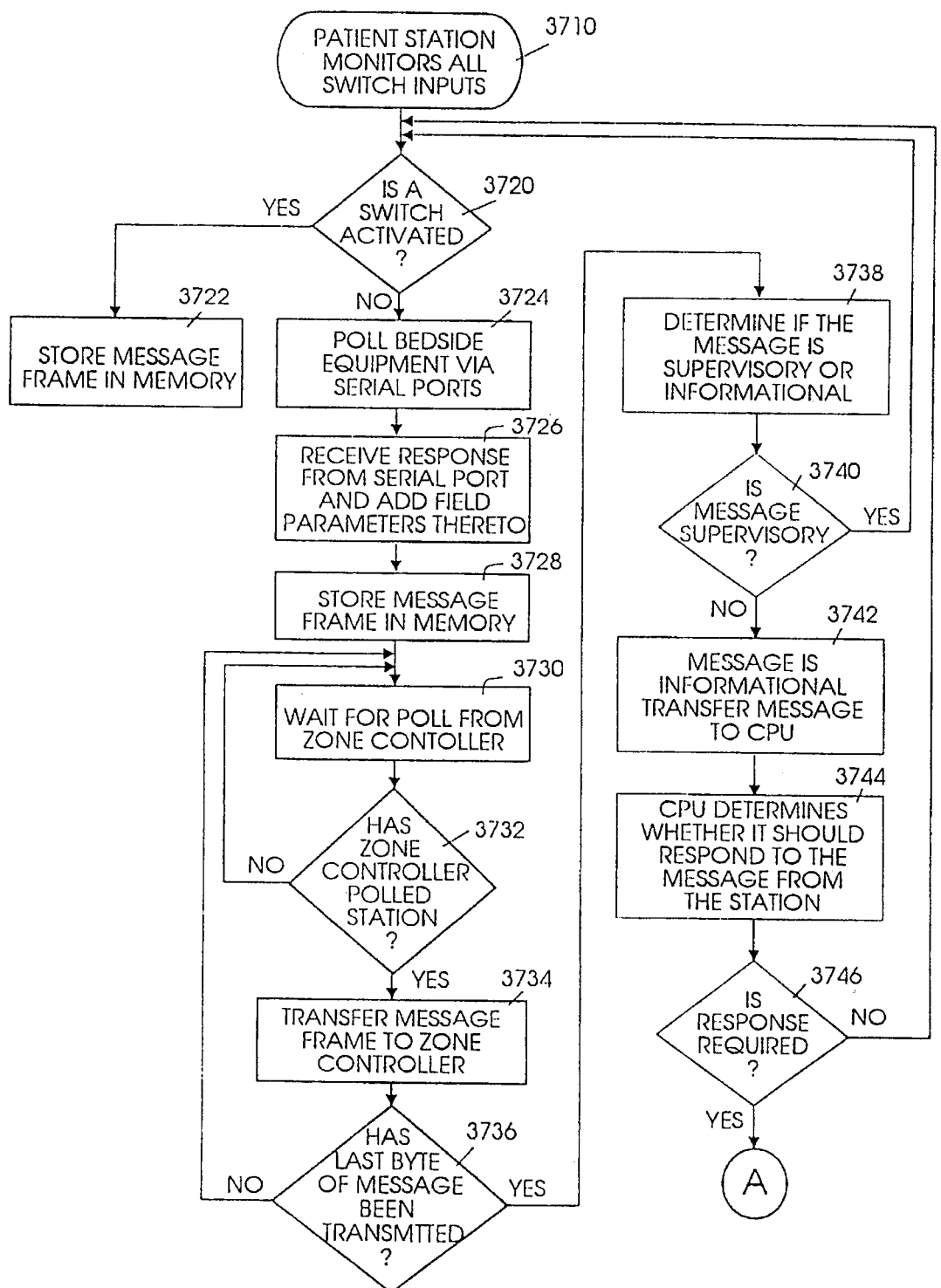
FIGS. 14a and 14b illustrate an exemplary flow-chart diagram of an operation of the patient station of FIG. 1.
Figure 14B:
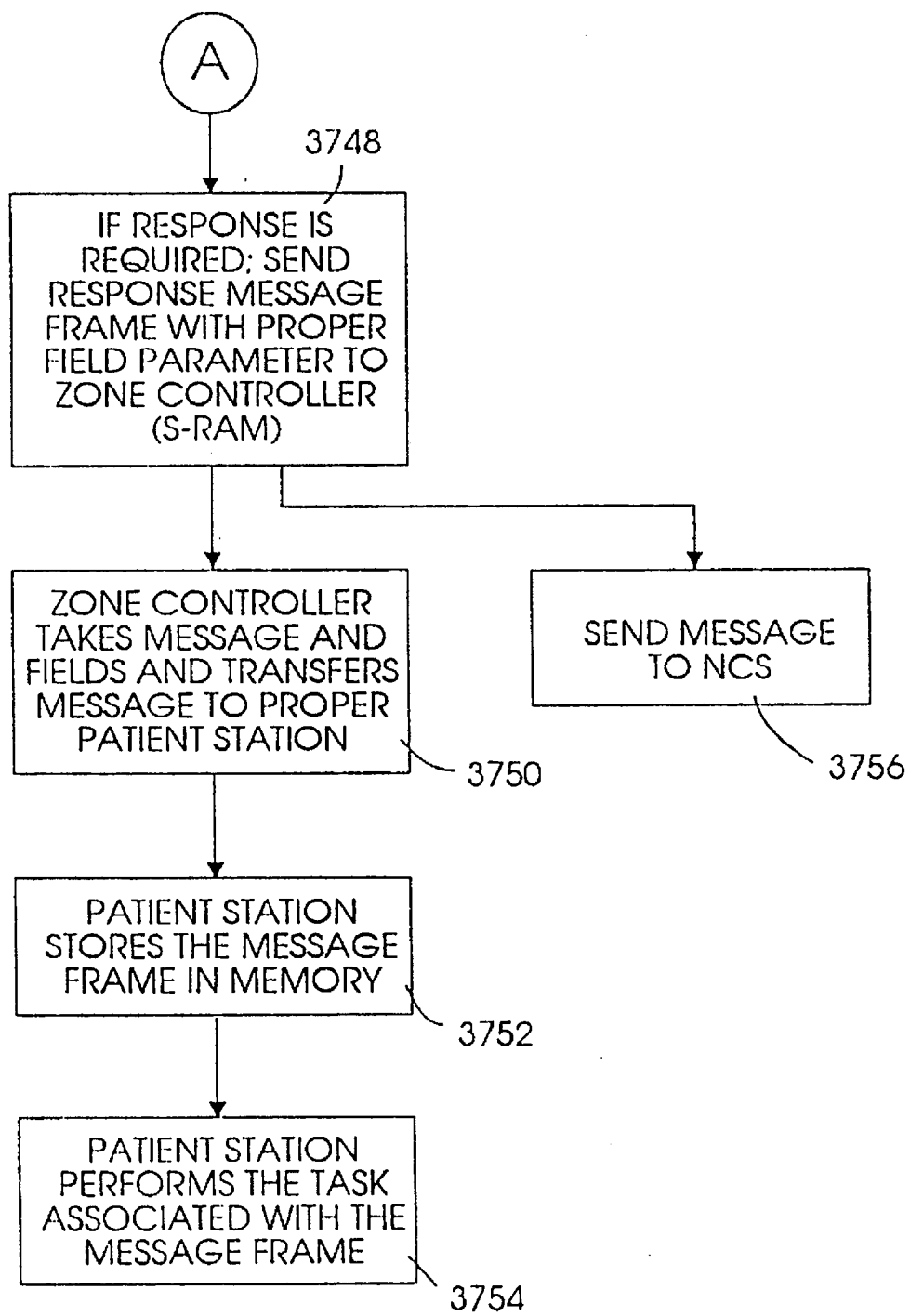

Referring again to FIG. 9, each patient station 2416 may be coupled to external peripheral equipment, such as controllers, indicators and/or switches, which provide medical instrument data and/or patient status data to staff members and which facilitate patient control of environmental facilities within the patient's room, as will be described below. FIGS. 14a and 14b represent an exemplary operational flow-chart of the interaction between the patient station and the bedside equipment and between the patient station and the CPU so as to facilitate communication between the bedside equipment and the CPU. Initially, the patient station monitors the inputs from the external peripheral equipment (e.g., switches) to determine if the equipment has been activated (steps 3710 and 3720). If a switch or other peripheral equipment is activated, a message frame associated with the activated switch will be stored in the memory of patient station circuitry 3510, shown in FIG. 12 (step 3722) and transferred to zone controller 2420. If, on the other hand, a switch has not been activated then the patient station will poll the bedside equipment via serial port 3534 (shown in FIG. 12) for status or message information and interpolate field parameters onto the received message (step 3724 and 3726). The message frame is then stored in patient station memory 3516 (shown in FIG. 12) and remains therein until the patient station 2416 is polled by the zone controller 2420 corresponding to the patient station (steps 3728, 3730 and 3732).

Once polled, the patient station transfers the message frame to the S-RAM 2512 (shown in FIG. 2) of the zone controller until the Last byte of the frame has been transferred (i.e., the F bit is set to logic 1) (steps 3734 and 3736). The zone controller then determines if the message frame, received is an S-frame or an I-frame, and if the message frame is an S-frame the zone controller acknowledges the message frame and the patient station returns to monitor the switch inputs (steps 3738 and 3740). If the received message frame is an I-frame the frame is transferred to the CPU which determines whether a response to the transmitting station is required (steps 3742, 3744 and 3746). If no response is required the CPU stores the received data and the patient station returns to monitor the switch inputs, as shown. If, however, a response is required a response message frame is sent to the zone controller and stored in the S-RAM (step 3748). The zone controller polls the patient station and if a received ready (RR) command is received in return, the response message frame is transferred to and stored in the patient station (steps 3750 and 3752).

Once the response message frame is received the patient station performs the task associated with the information in the frame (step 3754). In addition to sending a response message to the patient station, the CPU may also be required to send a message frame to the nurse control station to alert staff members of potential faults either through tone and visual indications similar to those illustrated in FIG. 18 or by adding the information to the problem report described above (step 3756).

Referring again to FIG. 9, in the preferred embodiment, patient station 2416 is connected to patient control unit 3210 via data link 3246. Patient control unit 3210 includes control buttons 3248 which facilitate patient control of the environmental facilities within the patient's room, via patient station 2416 and CPU 2412. Such environmental facilities include, for example, the television, radio, draperies and the room lighting.

Nurse call button 3250 is provided to enable the patient to call the nurse control station or stations within the group. As noted above, the communication between stations is facilitated by CPU 2412 utilizing the master/slave communication link described above.

Figure 15:
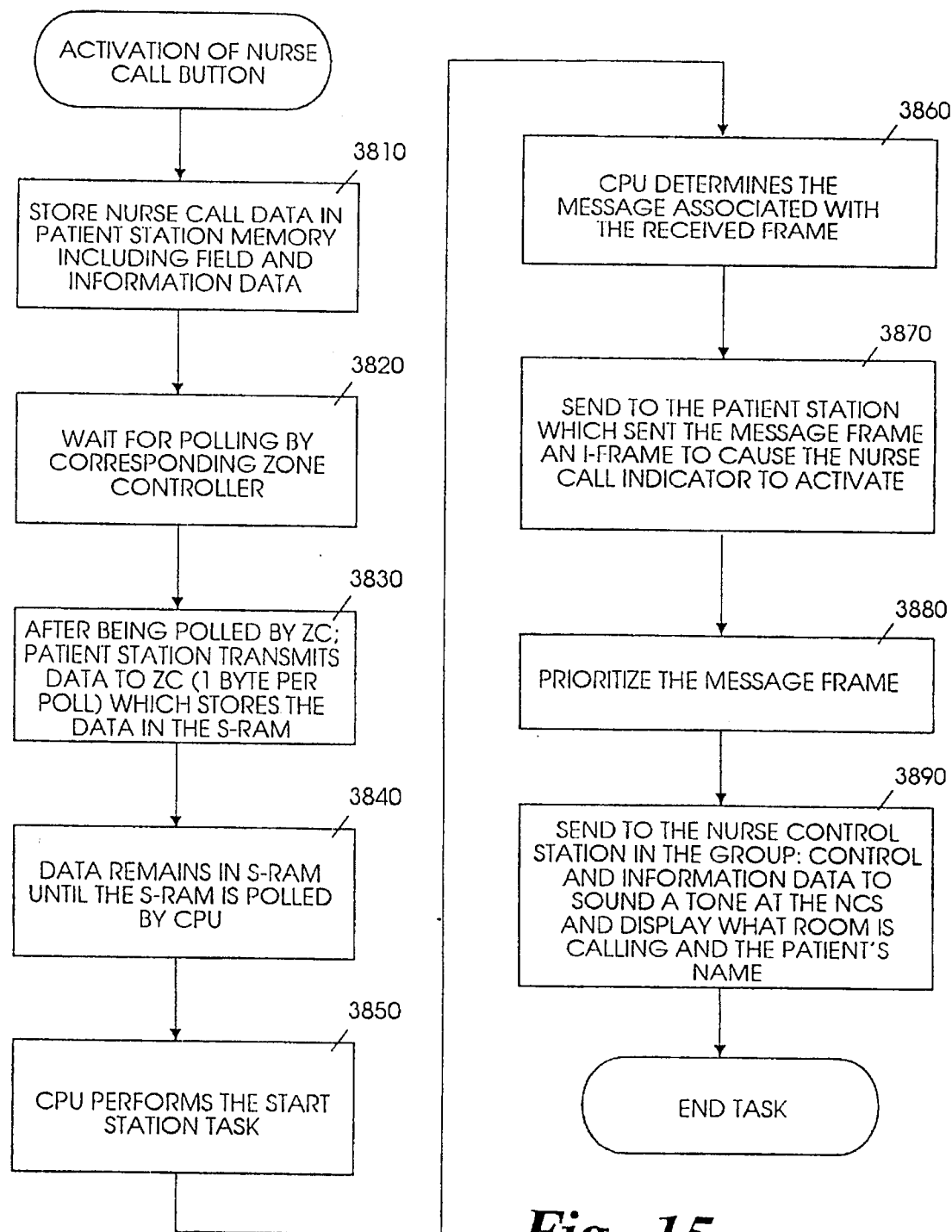
FIG. 15 is a flow-chart diagram associated with the internal circuitry for the patient stations illustrated in FIG. 1.

FIG. 15 illustrates an exemplary operational flow for the patient control unit 3210 in combination with patient station 2416. Upon activation of nurse call button 3250 of patient control unit 3210 (shown in FIG. 9), patient station 2416 receives the switch activation data via data link 3246 and buffers 3530 (shown in FIG. 12). Microprocessor 3512 then interpolates field data onto the received message to form a message frame, as described above, and stores the message frame in RAM 3518 (step 3810).

Once stored in memory, the nurse call data remains therein until the patient station is polled by the zone controller (step 3820). Once polled, the message frame is then transferred to the zone controller and stored in the S-RAM (step 3830). The data remains in the S-RAM until the S-RAM is polled by CPU 2412, upon which, the message frame is then transferred to the CPU (step 3840).

Reception of the message frame in the CPU causes the CPU to begin the station task identified in the INFORMATION field of the I-frame (step 3850), to determine the message received from the patient station and provide an appropriate response thereto (steps 3860 and 3870). For this example, CPU 2412 is responding to the activation of nurse call button 3250 of patient control unit 3210. The initial response to the activation of the nurse control button is to return a message frame to the patient station to activate nurse call indicator 3222 of indicator assembly 3220 (shown in FIG. 9). In addition, the CPU prioritizes the message frame utilizing the transition priority data of the PATH field and then sends to the nurse control station or stations connected in the group associated with the patient station, a message frame including tone and display data identifying the patient and the associated room number (steps 3880 and 3890). At this point, the station task is completed and the CPU returns to the listen task. Manual reset of the patient station by a responding staff member deactivates indicator 3222 and clears the message from the nurse control station display.

Referring once again to FIG. 9 patient station 2416 may also be connected to staff presence switch 3254, indicator assembly 3220, code blue switch 3234 and/or emergency code switch 3232. In the configuration shown, staff presence switch 3254 is connected to patient station 2416 via data link 3256 and when properly activated provides patient station 2416 with a signal indicative of the type of staff member present in the patient's room. Once activated, a message frame (e.g., an I-frame) is transferred to the CPU and an appropriate response is returned to that particular patient station, in a manner described above.

The responding frame from the CPU 2412 includes information to cause the activation of an indicator in indicator assembly 3220 which corresponds with the type of staff member in the patient's room. To illustrate, if the staff member entering the patient room is a registered nurse (RN), that person would activate switch 3258 which in turn would activate indicator 3224 of indicator assembly 3220 via patient station 2416 and CPU 2412. If the staff member entering the room is a licensed practical nurse (LPN), that person would activate switch 3260 of staff presence switch 3254, which in turn would activate indicator 3226 of indicator assembly 3220 via patient station 2416 and CPU 2412. If, on the other hand, the staff member entering the room is an aide, then that person would activate switch 3262 of staff presence switch 3254., which in turn would activate indicator 3228 of indicator assembly 3220. When the staff member leaves the patient's room, the particular staff member switch is deactivated so as to deactivate indicator assembly 3220.

In the preferred embodiment, indicator assembly 3220 is a four lamp light fixture (e.g., a dome lamp) having colored lenses associated with each lamp. The fixture is secured or otherwise positioned on the wall outside the patient's room, preferably above the doorway, to allow staff members in the hallway to simply look at each indicator assembly and determine the type of staff member in a particular patient's room, if any. Alternatively, the indicator assembly may be any known type sufficient to provide staff members with an indication as to the type of staff member in a patient's room, for example, the indicator may be a LCD display which identifies the type and the name of the staff member in the patient's room in response to information provided to the system by the above described staff locator system, described in more detail in commonly assigned U.S. application Ser. No. 07/924,101, filed Aug. 3, 1992, which is a continuation-in-part of copending U.S. patent application Ser. No. 07/559,196, filed on Jul. 27, 1990, the disclosure of which is incorporated herein by reference.

Figure 9:
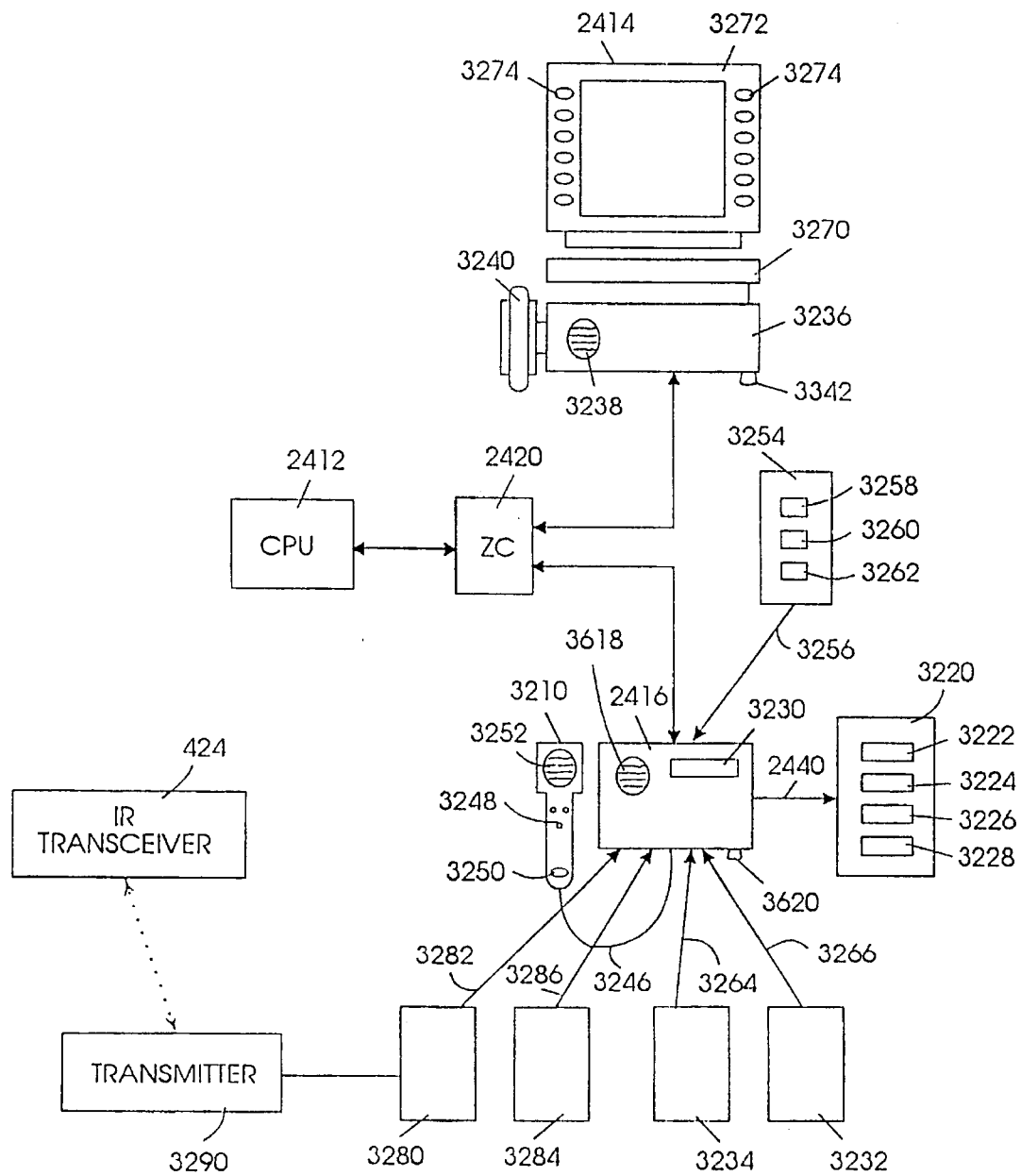
FIG. 9 is a functional block diagram of a system configuration similar to FIG. 1, illustrating a patient station having peripheral equipment connected thereto.

Code blue switch 3234 and emergency code switch 3232 are connected to patient station 2416 via data links 264 and 3266, respectively, as shown in FIG. 9, and are provided to allow staff members to initiate code blue or emergency responses directly from the patient's room. As noted above, code blue and/or emergency code procedures may also be initiated from nurse control station 2414. Initiation of the code blue response procedure at a patient station 2416 will result in the following occurrences. Initially the code blue data signal received from the code blue switch is stored in the patient station memory as a message frame, in a manner described above. The microprocessor 3512 (shown in FIG. 12) in the patient station 2416 then waits to be polled from the zone controller 2420 before transferring the data to the zone controller. Once polled by zone controller 2420 the message frame is transmitted to the zone controller and stored in the S-RAM 2512 until the S-RAM is polled by CPU 2412. Once the message frame is received within the CPU the message frame is prioritized and the station task associated with the data within the INFORMATION field of the message frame is initiated.

An example of a station task performed by the CPU in response to the activation of a code blue switch will be described below. Initially CPU 2412 determines the message type received from zone controller 2420. Next the CPU performs whatever function is associated with the message, in this example the message relates to the code blue function. In response to the code blue function, the CPU 2412 sends to the particular patient station an I-frame which includes data to cause activation of particular peripheral equipment as well as devices within the patient station 2416, e.g., a tone code and an indicator assembly activation code.

Next CPU 2412 determines which staff station or stations 2418 and which nurse control station or stations 2414 are grouped with the subject patient station 2416. Thereafter, CPU 2412 sends to each associated staff station an I-frame including message data to display "code blue" on staff station display 2422 of staff station 2418. Next CPU 2412 sends a message to the ZIA 3022, shown in FIG. 7, to activate the proper indicator associated with the patient station group in a manner similar to that described above with reference to fail safe bus 3020.

The CPU 2412 then sends an I-frame to each nurse control station grouped with the patient station to display the room number and identity of the patient subject to the code blue function, on the display of the nurse control station. The CPU 2412 then sends to the nurse control station an I-frame including appropriate control signals associated with the patient station message. Once the above steps are accomplished the station task is completed and the CPU 2412 returns to the listen task.

The system of the present invention may also be configured to monitor medical equipment being used to treat the patient (i.e., bedside equipment). Such bedside equipment may be connected to communication port 3534 (shown in FIG. 12) of patient station 2416. In instances where the serial data from the bedside equipment is not configured for RS-485 protocol, serial data converter 2520 (shown in FIG. 2) may be interconnected between serial port 3854 of patient station 2416 and the serial port of the bedside equipment. Typically, the serial port of the bedside equipment is configured to operate with RS-232 protocol, thus, serial data converter 2520 would be an RS-485 to RS-232 converter which is known in the art.

Examples of the above described bedside equipment are shown in FIGS. 9. As shown, a heart rate monitor 3280 is connected to patient station 2416 via data link 3282, which as noted above is operatively connected to nurse control station 2414 via zone controller 2420 and CPU 2412. The patient station (acting as a master station) polls heart rate monitor 3280 (operating as a slave station) to verify that the patients heart rate falls within the proper range as determined by the monitor. The zone controller periodically polls patient station 2416, as described above for an S-frame or an I-frame message frame. Typically with respect to this example, if no fault is detected the patient station will respond to the polling of the zone controller with an S-frame indicating proper operation of heart rate monitor 3280. However, a fault detected in monitor 3280 will be stored in RAM 3518 of patient station circuitry 3510 (shown in FIG. 12) along with the appropriate field data in the form of an I-frame, and the I-frame is transferred to zone controller 2420 and CPU 2412 in a manner described above. The CPU then analyzes the I-frame and an appropriate alarm sequence is initiated to notify staff members at nurse control station 2414 of the detected fault.

As another example, an intravenous (IV) pump 3284 is connected to patient station 2416 via data link 3286, which as noted above is operatively connected to nurse control station 2414, via zone controller 2420 and CPU 2412. In this example, the IV pump is periodically monitored by patient station 2416 to ensure that the flow rate of the pump is appropriate. If a failure is detected, a message frame including the error message is transferred to CPU 2412 in a manner set forth above. The CPU the initiates an appropriate alarm sequence, such as displaying a message on the monitor of nurse control station 2414, that the IV container is empty and needs to be changed. It should be noted, that numerous other types of bedside equipment may be monitored by the system of the present invention, including respirators and heart monitors.

Transmitter 3290 is hardwired to the bedside equipment, e.g., heart rate monitor 3280, and is provided to enable a central computer system to determine what room or other area of the health care facility the bedside equipment is located and to transmit operation data generated by the bedside equipment, such as status data or other data associated with the operation of the equipment. In this configuration, transmitter 3290 transmits an identification signal and the operation data to an IR transceiver which is in communication with the central computer through a network server as described in application Ser. No. 07/924,101. The central computer determines which transceiver received the identification signal of the bedside equipment and transfers the location data of the equipment and the operation data to CPU 2412 via data link 2728 (shown in FIG. 4). Transmitter 3290 may be a radio frequency transmitter operating at a frequency of approximately 300 MHz, which are available from Dallas Semiconductor, Inc.

STAFF STATION

Referring again to FIG. 1, staff station 2418 is similar in design to patient station 2416. In the preferred embodiment, staff station 2418 may be configured, in the initial system configuration setup, to operate in a "duty" mode or a "staff" mode. In the "duty" mode staff station 2418 provides patient call indications on staff station display 2422, as well as facilitating communication with nurse control station 2414. In the "staff" mode staff station 2418 facilitates communication with nurse control station 2414.

Figure 16:
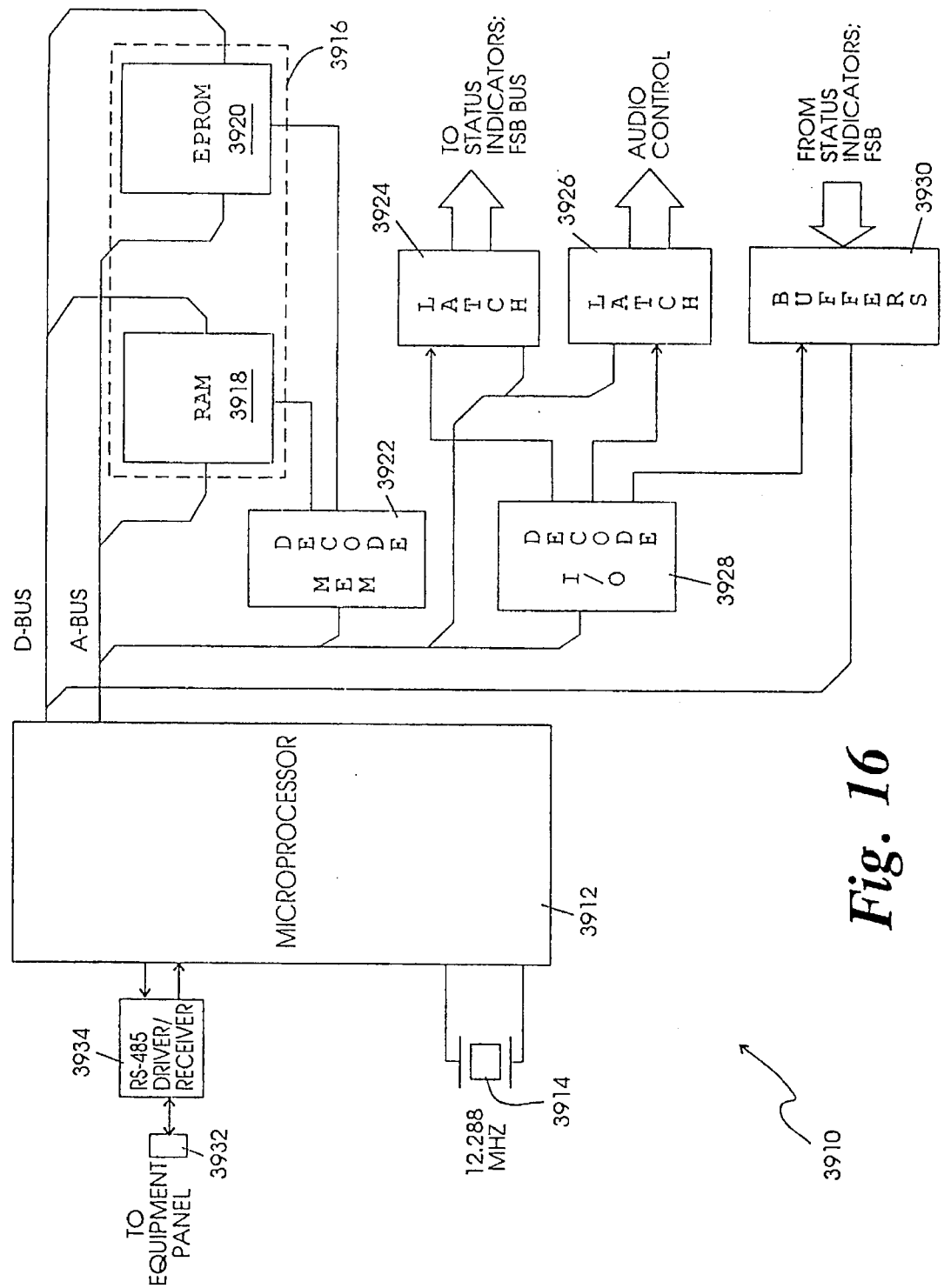
FIGS. 16 and 17 are circuit block diagrams for the internal circuitry for the staff stations illustrated in FIG. 1.

FIG. 16 illustrates hardware configurations for the staff station circuitry 3910 installed within staff station 2418. The staff station circuitry 3910 includes microprocessor 3912, such as model 64180 manufactured by Motorola operating at a frequency of 12,888 MHz. via crystal 3914, 96 Kbytes of memory 3916 (e.g., 64 Kbytes of flash ROM and 32 Kbytes of RAM) having stored programs, e.g., system and application programs. In this exemplary configuration, the data and address buses of the microprocessor are connected to the memory, e.g., RAM 3918 and an EPROM 3920. Memory decoder 3922 is utilized to select between RAM 3918 and EPROM 3920 in response to a particular address on the address bus. The address bus is also connected to a pair of latches 3924 and 3926 which interface the microprocessor to status indicators, the fail safe bus (FSB), the audio control circuitry, and to switches and other peripheral equipment connected to the staff station, as shown. In addition, I/O decoder 3928 is utilized to select between either latch in response to a particular address on the address bus. Incoming signals from the above noted peripheral equipment are received by buffer 3930 and then transferred to the data-bus upon being enabled by I/O decoder 3928.

Utilizing the preferred microprocessor (i.e., the Motorola 64180), serial communication between the zone controller and the microprocessor may be accomplished through asynchronous serial communication port 3932 which is, preferably, configured to RS-485 protocol utilizing RS-485 driver/receiver (RS-485 D/R) 3934 as shown.

Figure 17:
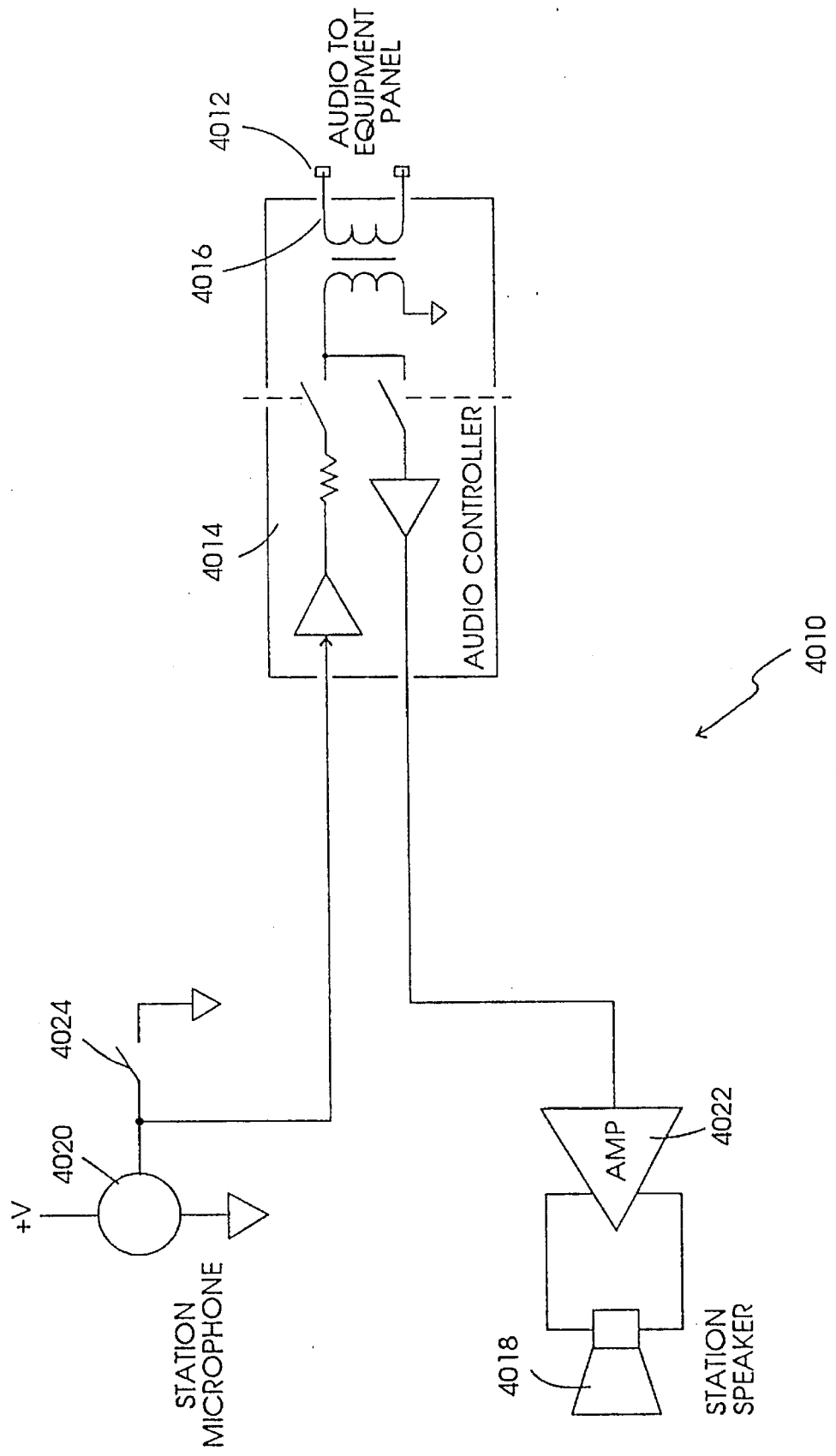

FIG. 17 illustrates hardware configurations for the audio portion 4010 of staff station 2418. As shown, audio pair 4012 from an equipment panel (e.g., audio matrix 2510 shown in FIG. 2) is connected to the front end of audio controller 4014. Preferably, the front end of audio controller 4014 includes a coupled 600 ohm balanced transformer 4016 which isolates the internal audio circuitry of staff station 2418 from the external audio circuits. Depending upon whether the audio signal is being received or transmitted, the back end of audio controller 4014 directs the audio signal to staff station speaker 4018 or directs the audio signal from microphone 4020 to audio matrix 2510 via audio controller 4014.

Preferably, audio controller 4014 is a 34118 audio controller manufactured by Motorola. Audio input signals from audio matrix 2510 which pass through the audio controller are directed to staff station speaker 4018 via amplifier 4022. Audio generated by the staff station via microphone 4020 is selectively transferred through audio controller 4014 onto the audio pair as shown. Mute switch 4024 may be provided to allow a staff member to manually short out the microphone so as to prevent audio signals from being generated at the patient station.

SYSTEM FUNCTIONS

The patient care and communication system of the present invention may be programmed to perform numerous operations associated with patient care and communications within a hospital or other health care facility. The following functions are exemplary of the numerous types of features and the functional flow (or data exchange) between the different stations, the CPU and the zone controller utilize the above described preferred master/slave communication link.

a. Call Priority

Message frames usually in the form of an I-frame originated by a nurse control station, a patient station and/or a staff station are interpreted by CPU 2412 and assigned a priority level based upon the type of message frame received (i.e., the DTYPE field of the INFORMATION field contains the message type which corresponds to the priority level that will be assigned to the frame). In addition, the message associated with the TEXT field of the message frame is displayed on nurse control station display 3272 of a nurse control station 2414 in order of priority level. The priority levels are preprogrammed during the initial set-up of the system configuration, but may be altered by staff members at nurse control station 2414 via keyboard 3236 or direct select keys 3274 (shown in FIG. 9). The highest priority call will be displayed first and other calls will follow in descending order according to the priority level.

Preferably, each call originated has specific audible and visual signaling based on the call priority level which are distributed to the necessary nurse control stations, zone indicator assembly, patient stations and/or staff stations via CPU 2412 and their respective zone controller. FIGS. 18–20 represent tables illustrating exemplary embodiments of call priority levels, their associated visual and tone indications which are generated at either the nurse control station, the patient station and/or the staff station. FIG. 18 illustrates the preferred visual display which appear on nurse control station display 3272 and the tones generated at speaker 3238 (shown in FIG. 9) in response to the various priority levels. For example, in response to the activation of code blue switch 3234 (shown in FIG. 9) CPU 2412 will transmit to nurse control station 2414 a message frame instructing the nurse control station to display on the nurse control station display 3272 a flashing arrow directed at a direct select key 3274 to indicate which key will enable the staff member to connect the audio of the nurse control station to the audio of the patient station and respond to the call. The arrow will flash at a rate of approximately 120 pulses per minute (PPM). In addition, the room number and bed number associated with the patient station to which the code blue switch is connected and the "CODE BLUE" message will be displayed on nurse control station display 3272. An audible tone at the rate of 120 PPM will also be generated at speaker 3238 of nurse control station 2414.

The preferred response at patient station 2416, shown in FIG. 19, to the activation of the code blue switch will be to pulse a station call and bed call placement LED indicators (not shown), which may be positioned on the front panel of patient station 2416, at a rate of 120 PPM, and to pulse a code blue indicator of the corresponding group indicator assembly 3024 via ZIA 3022 (shown in FIG. 7) at a rate of 120 PPM.

The preferred response at staff station 2418, shown in FIG. 20, to the activation of the code blue switch will be to pulse an incoming call LED indicator which may be positioned on the front panel of staff station 2418, at a rate of 120 PPM, to display on staff station display 2422 (shown in FIG. 1) the room and bed number associated with the patient station to which code blue switch 3234 is connected and to display the "CODE BLUE" message; to pulse a blue indicator of the corresponding group indicator assembly 3024 via ZIA 3022, at a rate of 120 PPM; and to generate an audible tone at the rate of 120 PPM at speaker 4018 of staff station 2418 (shown in FIG. 1).

b. Nurse Follow

The nurse follow feature allows a staff member to selectively direct incoming calls to a particular nurse control station to selected patient stations and/or staff stations. To illustrate, this feature may allow the staff member to program the nurse control station to distribute incoming calls to a single patient station, to patient stations where particular staff members have activated respective staff presence switches (e.g., switch 3254, shown in FIG. 9) and/or to all patient or staff stations assigned to the group associated with the particular nurse control station. Thus, when a staff member is required to leave the area of a nurse control station, incoming calls to the nurse control station can be routed to locations where appropriate staff members can respond to the call.

In operation, a staff member attending nurse control station 2414 may utilize direct select keys 3274 (show in FIG. 9) in response to menu driven prompts to configure the system to operate in the nurse follow mode. In the nurse follow mode, calls which are directed to the nurse control station 2414 via CPU 2412 and corresponding zone controllers 2420 will automatically be routed to the station or stations selected by the staff members or to stations in locations where that staff member or other staff members are determined to be present by staff locator system 2428 (shown in FIG. 4 and described in U.S. application Ser. No. 07/924,101).

For example, if the staff member selects the nurse follow feature which routes incoming calls to patient stations where the RN switch 3258 of staff presence switch 3254 (shown in FIG. 9) has been activated, CPU 2412 will direct the incoming call to the nurse control station to any room in the group where switch 3258 of staff presence switch 3254 has been activated.

As another example, CPU 2412 of the patient care and communication system interacts with the central computer system of staff locator system 2428, shown in FIG. 4. In this configuration, the identification badges are in communication with the central computer system in a manner described in application Ser. No. 07/924,101, which is incorporated herein by reference. In particular, FIGS. 4 and 17c of that application, show the identification badge 1111, which is worn by the staff member, continually transmits the identification signal (of the staff member) and the central computer system continually monitors the identification signal to update the location of the badge (and the staff member). The location information of the staff member is transferred to CPU 2412 via data link 2726 (shown in FIG. 4) which may be any known type of communication link utilized to facilitate communication between computer systems. Therefore, when a call is directed to a nurse control station 2414 programmed to operate in the nurse follow mode, CPU 2412 will route the incoming call to a station (either 2416 or 2418) positioned nearest the detected location of the staff member. In an alternative embodiment, a staff member attending the nurse control station may want to route incoming calls to locations of other staff members. In this embodiment, the nurse control station can be programmed in the nurse follow mode to route the incoming calls intended for nurse control station 2414, to stations where the other staff members have been detected by the staff locator system.

c. Voice Paging

Figure 21:
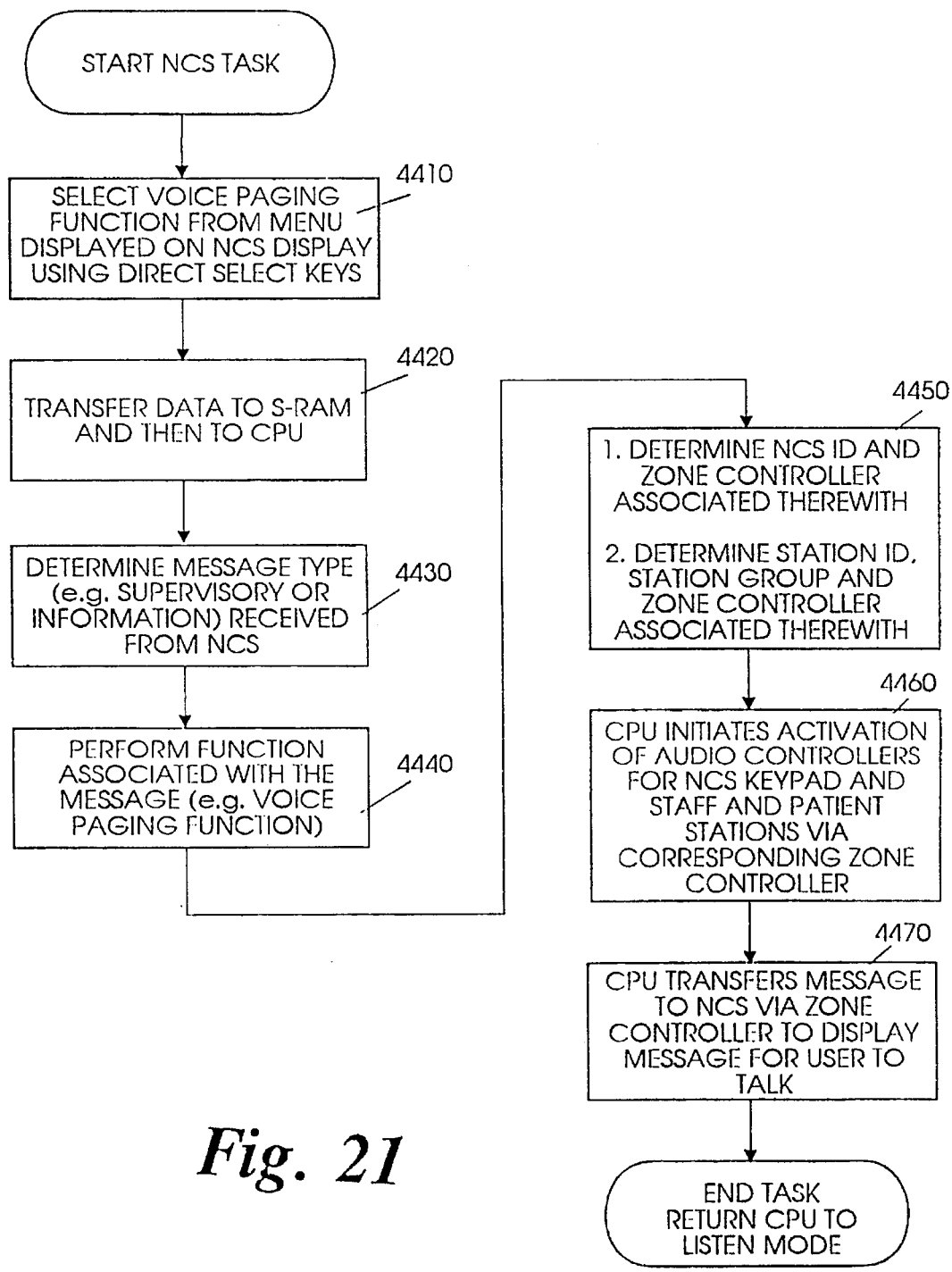
FIG. 21 is flow-chart diagram for the central processing unit illustrated in FIG. 12.

The voice page feature allows staff members to communicate to selected patient and/or staff stations from the nurse control station. To illustrate, this feature allows a staff member to communicate to all staff members who have activated staff presence switches associated with the nurse control station (i.e., within the same group) and all staff members in areas where staff stations are located. FIG. 21 illustrates an exemplary operational flow for the voice paging feature of the present invention. Initially, the staff member desiring to page all staff members within the assigned group, programs nurse control station 2414 via direct select keys 3274 (shown in FIG. 9) which activate menu driven functions (step 4410). The menu driven instructions from the nurse control station are then transferred to the CPU via zone controller 2420 in a manner described above (step 4420). The CPU analyzes the instructions, e.g., determines the identification of the patient and/or staff stations and their associated zone controllers and the CPU performs the function associated with the received message frame (step 4430, 4440 and 4450). Thereafter, the CPU causes the audio connection between each station and the nurse control station and notifies the paging staff member to begin talking (steps 4460 and 4470).

Alternatively, the voice paging feature may utilize staff locator system 2428, shown in FIG. 4 to determine the location of a staff member or members so that the staff member attending nurse control station 2414 may communicate with the patient and/or staff stations nearest to each staff member or members being paged.

d. Room Monitoring

The room monitoring feature allows staff members attending a nurse control station 2414 to activate the audio system of either a selected number of patient stations 2416 or to manually step or automatically scan through each patient station 2416 in each room associated with the station grouping, described above, in a predetermined order for a predetermined period of time so as to activate microphone 3520 of patient station 2416, enabling staff members to listen for sounds of distress or other uncharacteristic noises so as to check on the well being of a patient or patients. Preferably, the predetermined order for monitoring rooms is from the lowest room number to the highest and the predetermined period of time is approximately ten seconds. In operation, the staff member attending nurse control station 2414 configures the system for automatic room monitoring by depressing direct select keys 3274 of nurse control station display 3272 in response to menu driven prompts. Once configured for automatic monitoring, CPU 2412 sends a message frame to each patient station in the above noted order to activate microphone 3620 (shown in FIG. 13) of audio circuitry 3610, via audio controller 3614, for a period of ten seconds to allow the attending staff member to listen for distress noises and other uncharacteristic noises.

DIAGNOSTICS

The system of the present invention also provides diagnostic features which continuously monitor system components. As noted above, system faults are communicated to the nurse control station and/or to the staff station and added to the problem report. Hard and/or soft copies of the problem report may be obtained from printer 2724 and/or external computer 2722 (shown in FIG. 4) or the problem report may be displayed on nurse control station display 3272 when the "problem reports" feature is selected by direct select keys 3274 shown in FIG. 9.

In addition, the operation of selected periphery devices in the patient's room are continuously monitored and any failures are brought to the attention of the staff member at a nurse control station within the group. For example, the wiring to code blue switch 3234, the smoke alarm and/or the nurse call button 3250 on patient control unit 3210 may be monitored for damaged to the wires between such periphery devices and patient station 2416.

Figure 22:
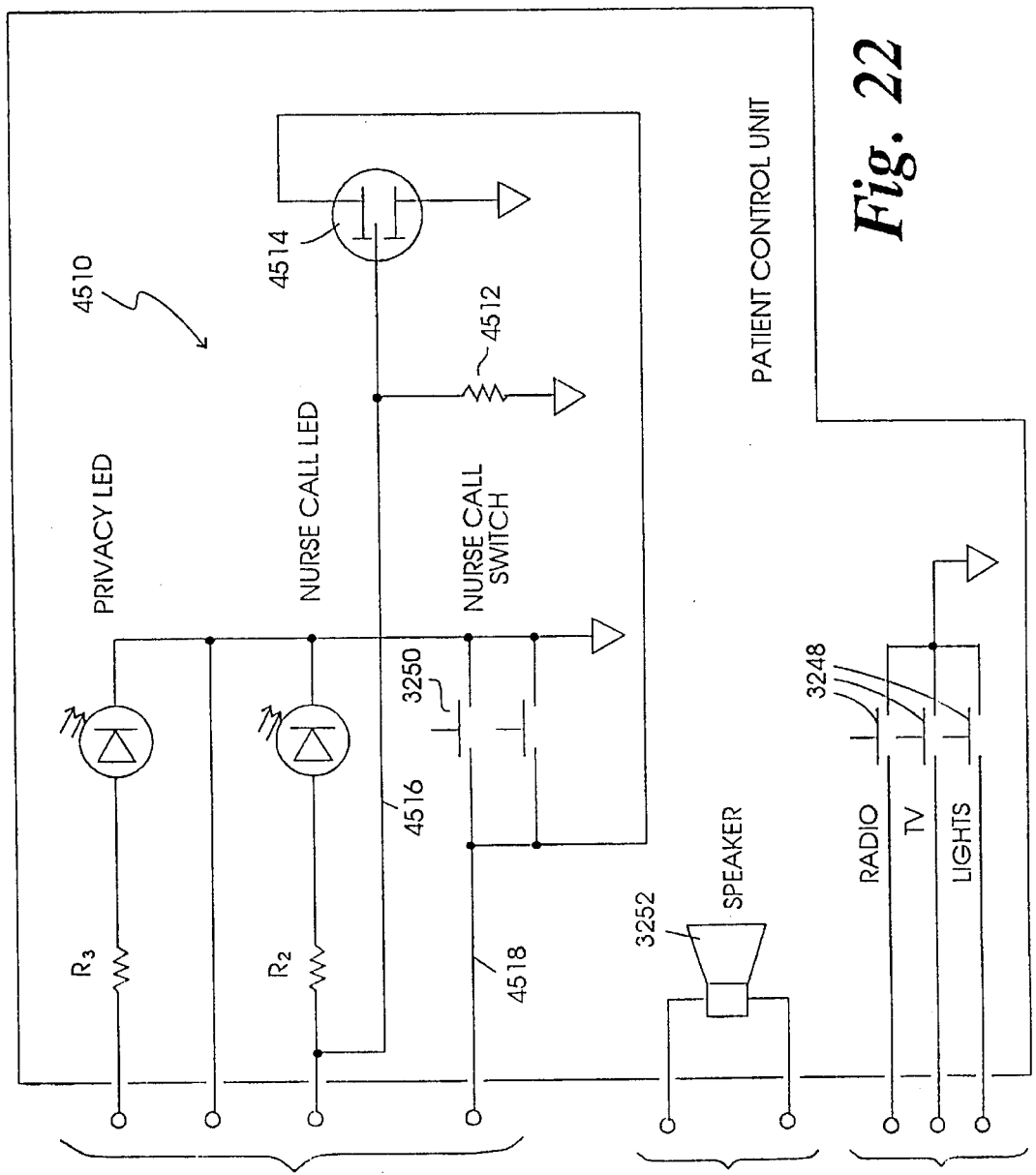
FIG. 22 is a circuit diagram for the patient control unit illustrated in FIG. 10 and showing self-test circuitry for performing automatic continuity tests of interconnecting wires.

FIG. 22 shows the hardware components for patient control unit 3210 which is connected to patient station 2416. Preferably, the wiring is tested by microprocessor 3512 (shown in FIG. 12) activated signals in combination with the wire test circuitry 4510. Wire test circuit 4510 includes resistor 4512 and field effect transistor (FET) 4514 which are connected between call wire 4516 and nurse call wire 4518, as shown. In this configuration, microprocessor circuitry 3510 of patient station 2416, shown in FIG. 12, periodically turns on FET 4514 via call wire 4516 therefore completing the ground path connecting call wire 4516 and nurse call wire 4518. Microprocessor 3512 then interrogates nurse call wire 4518 via buffer 3530 (shown in FIG. 12) in response to microprocessor driven instructions, so as to perform a continuity check of the nurse call feature of patient control unit 3210. Preferably, the period between each wire test is two seconds. Wire test circuit 4510 may be utilized to perform wire tests between any periphery equipment and the processor associated with the station to which the peripheral equipment is connected. In the event the continuity check fails, a failure alarm sequence is initiated to notify staff members of the wire failure and which wire in which periphery device has failed.

The patient care and communication system of the present invention also includes external diagnostic device 2570 connected to serial data converter 2520, as shown in FIG. 2. Preferably, external diagnostic device 2570 is a modem provided to facilitate external diagnostics of the patient care and communication system of the present invention, via converter 2520 and zone controller 2560. External diagnostic device 2570 allows a technician or other service personnel to remotely verify and update the configuration of the system in a manner similar to that performed by staff members attending a nurse control station. In addition, the external diagnostic device 2570 allows the technician or other service personnel to view the system problem report which, as noted above, includes information as to which stations or equipment are not operational.

STATIONS WITH PBX TELEPHONE INTERFACE

Figure 23:
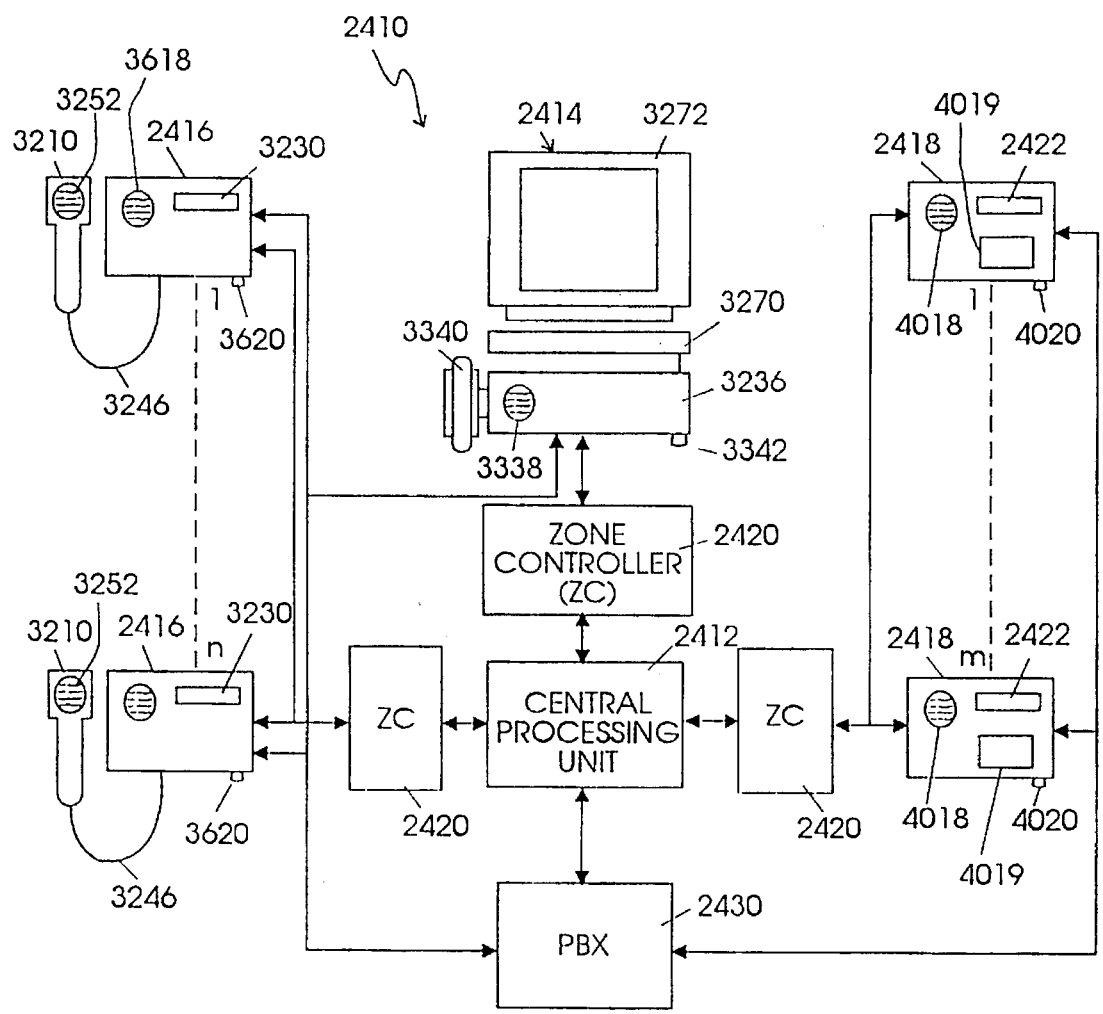
FIG. 23 is an illustration of the components of an alternative embodiment of the patient care and communication system of the present invention.
Figure 24:
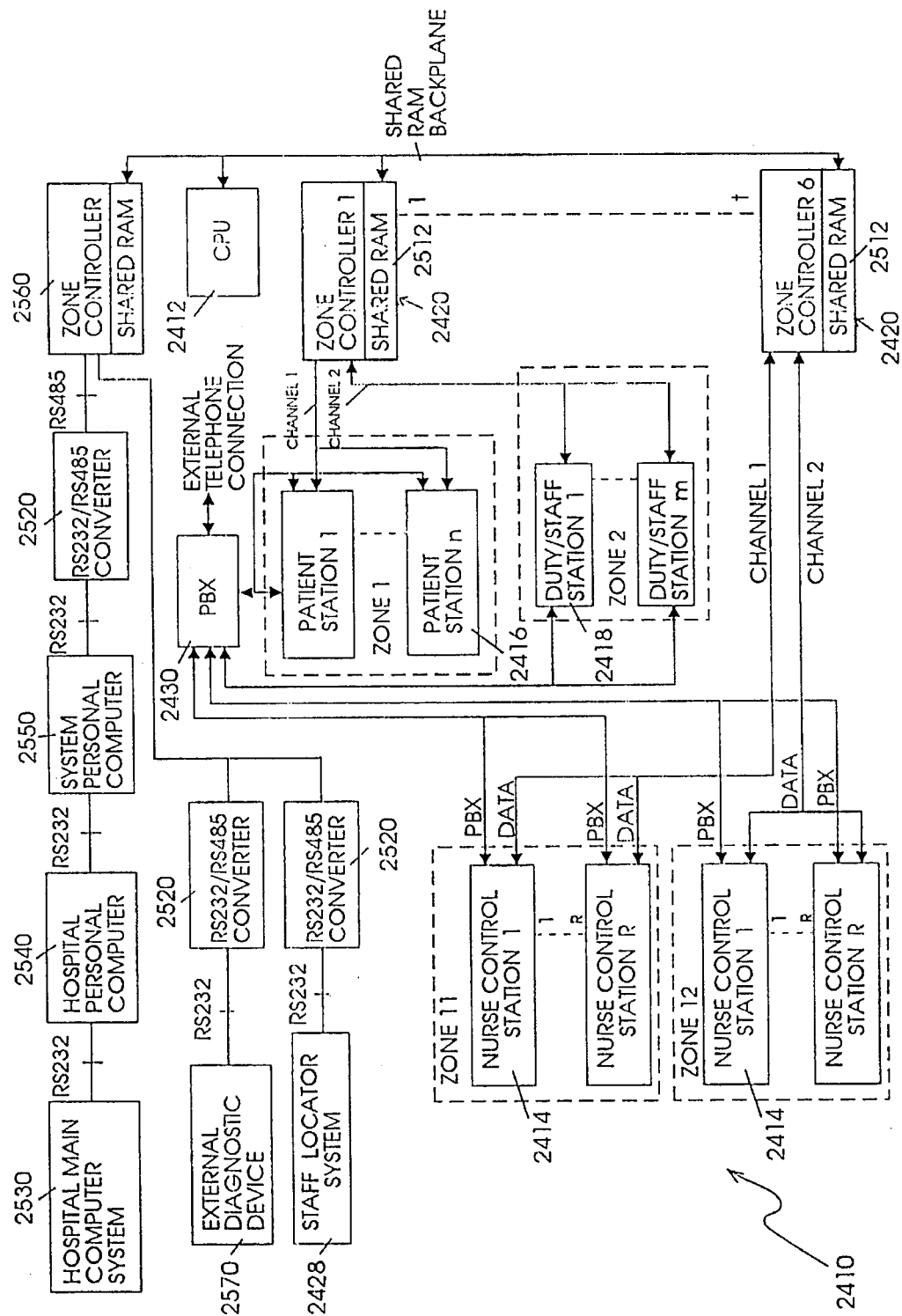
FIG. 24 is a functional block diagram of the alternative embodiment of the patient care and communication system configuration of FIG. 23, illustrating a private-branch exchange connected to the stations for telephone communications.

An alternative embodiment for the system configuration is shown in FIGS. 23 and 24. In this embodiment a private-branch exchange (PBX) 2430 is connected to nurse control stations 2414, patient stations 2416 and staff stations 2418 for providing staff-to-staff, staff-to-patient and/or external telephone communications for the hospital environment. The PBX 2430 also connects to a plurality of telephones throughout the facility and to or from external telephone lines of the telephone local exchange or central office. The components of a PBX for processing data and controlling the telephone operations are well known. The PBX according to the present invention includes a processor, associated memory and stored programs. The preferred PBX according to the present invention is the IDS-228, manufactured by EXECUTONE Information Systems, Inc. Each station is provided with a PBX interface which facilitates PBX telephone or voice communications therebetween. System data communications are accomplished in a manner described above utilizing zone controllers 2420 and the above described protocol.

Figure 25:
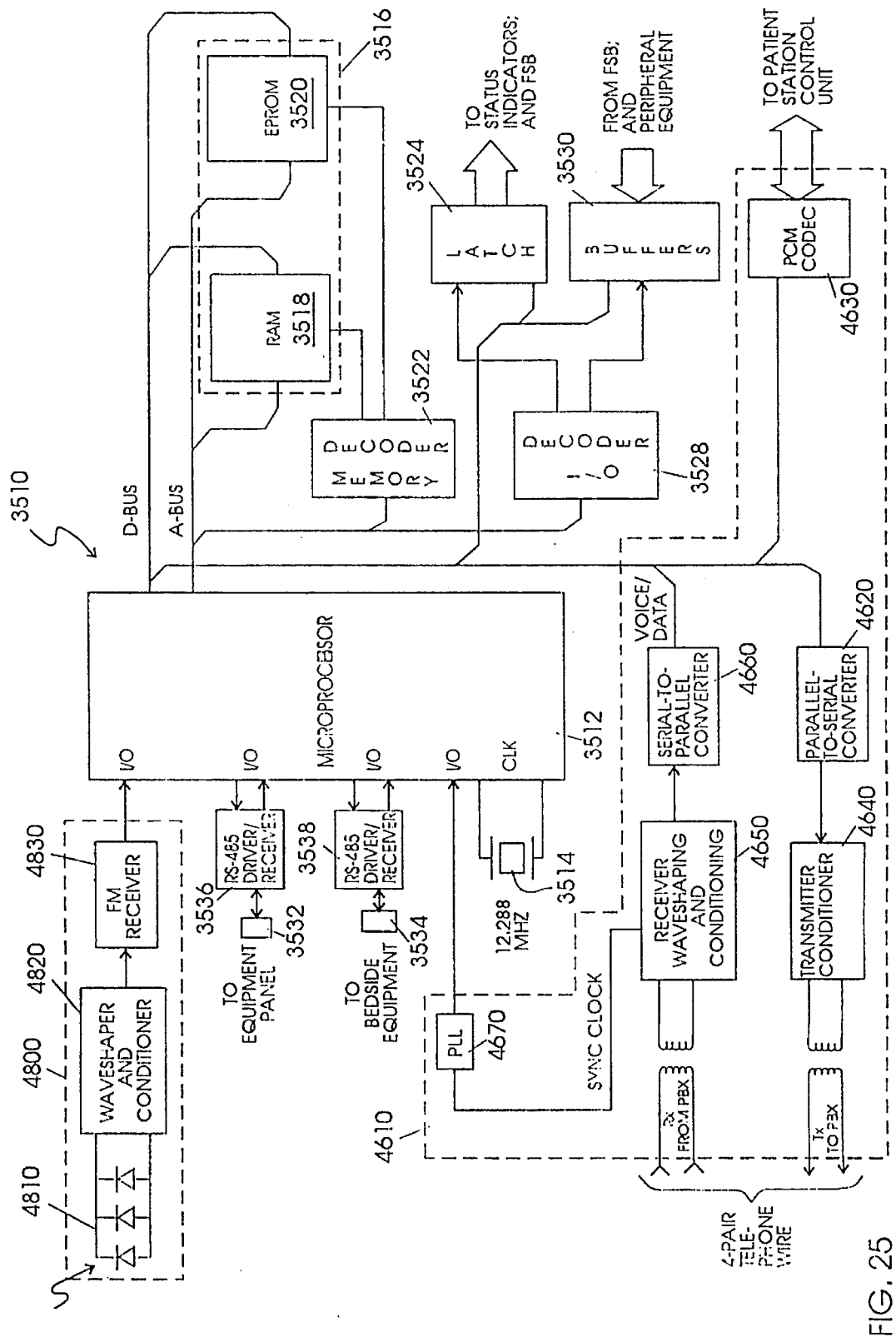
FIG. 25 is a circuit block diagrams for an alternative embodiment of the internal circuitry for the patient stations illustrated in FIG. 23.

FIG. 25 is a circuit block diagram of the patient station 2416 according to the alternative embodiment, which includes a telephone circuit 4610, which in turn connects to the PBX 2430. The patient station further includes a receiver unit 4800 for sensing or receiving signals transmitted from the portable badges. As shown, the patient station 2416 is a microprocessor controlled interface having similar system data communications as the patient station described above with reference to FIGS. 4, 9 and 12-14b. Further, the telephone circuit 4610 facilitates telephone communication between a patient via patient station control unit 3210, shown in FIG. 23, and the internal and external telephone systems via PBX 2430, shown in FIG. 24.

According to the alternative embodiment, the receiver unit 4800 receives wireless electromagnetic transmissions, preferably infrared and frequency modulated (FM), from a portable transmitter. The transmissions from the portable-transmitter include transmitter ID signals. The receiver in turn forwards an information packet including the received transmitter ID signals to the central processing unit 2412 which determines the identity and location of the transmitter. The information packet from the receiver 4800 is preferably forwarded to the central processing unit 2412 through zone controller 2420. Alternatively, the information packet is forwarded to the PBX 2430 through telephone circuit 4610. According to the alternative embodiment of the present invention, the PBX 2430 is capable of processing the information packet from the receiver 4800 to determine the identity and location of the transmitter, both independently from or as a shared resource of the central processing unit 2412. Of course, the information packet from the receiver 4800 may be forwarded to the central processing unit 2412 via the PBX 2430 or vice versa.

Typically, telephone voice and data communication between each station and the PBX 2430 is in the form of message frames which are divided into fields, e.g., a data field and a control field. As an example, the data field associated with voice data to the station is approximately 64 kilobits in length and the control field is approximately 2 kilobits in length. The control field includes a sync bit for synchronizing communications between the telephone and the PBX. The preferred transmission rate for data is 19.2 kilobits per second.

According to the alternative embodiment, a robbed bit signaling technique is utilized for transferring data from the patient, staff or nurse control station to the PBX. For example, utilizing this technique, one bit within every fourth transmission of the voice/data stream is utilized for the transmission of the system data. Thus the effective data transmission rate of the control data is approximately 2 kilobits per second.

Figure 26:
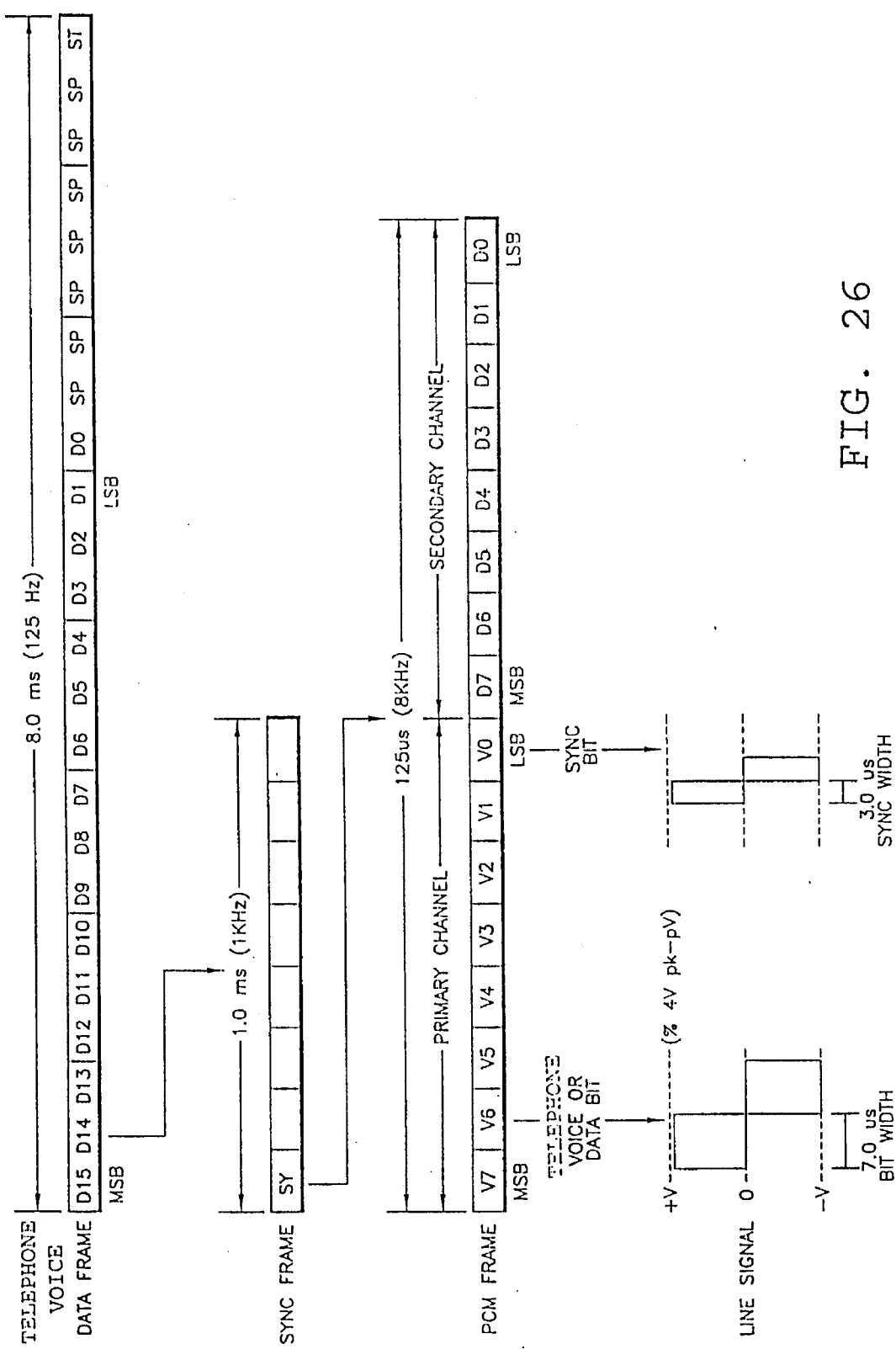
FIG. 26 illustrates the data frames for communication between the stations and the private-branch exchange.
Figure 27:
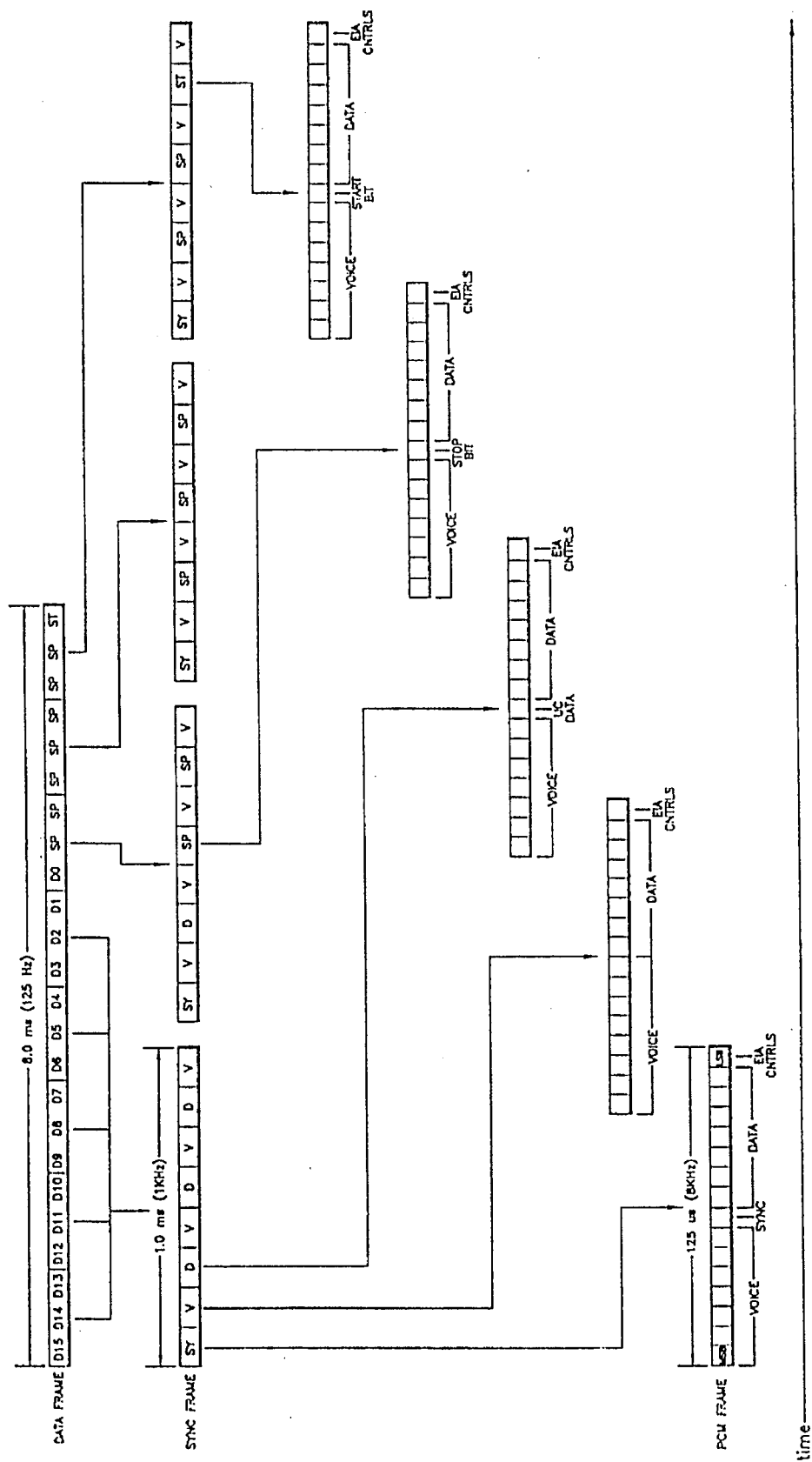
FIG. 27 illustrates the data frames for communication from the stations to the private-branch exchange in an expanded form.
Figure 28:
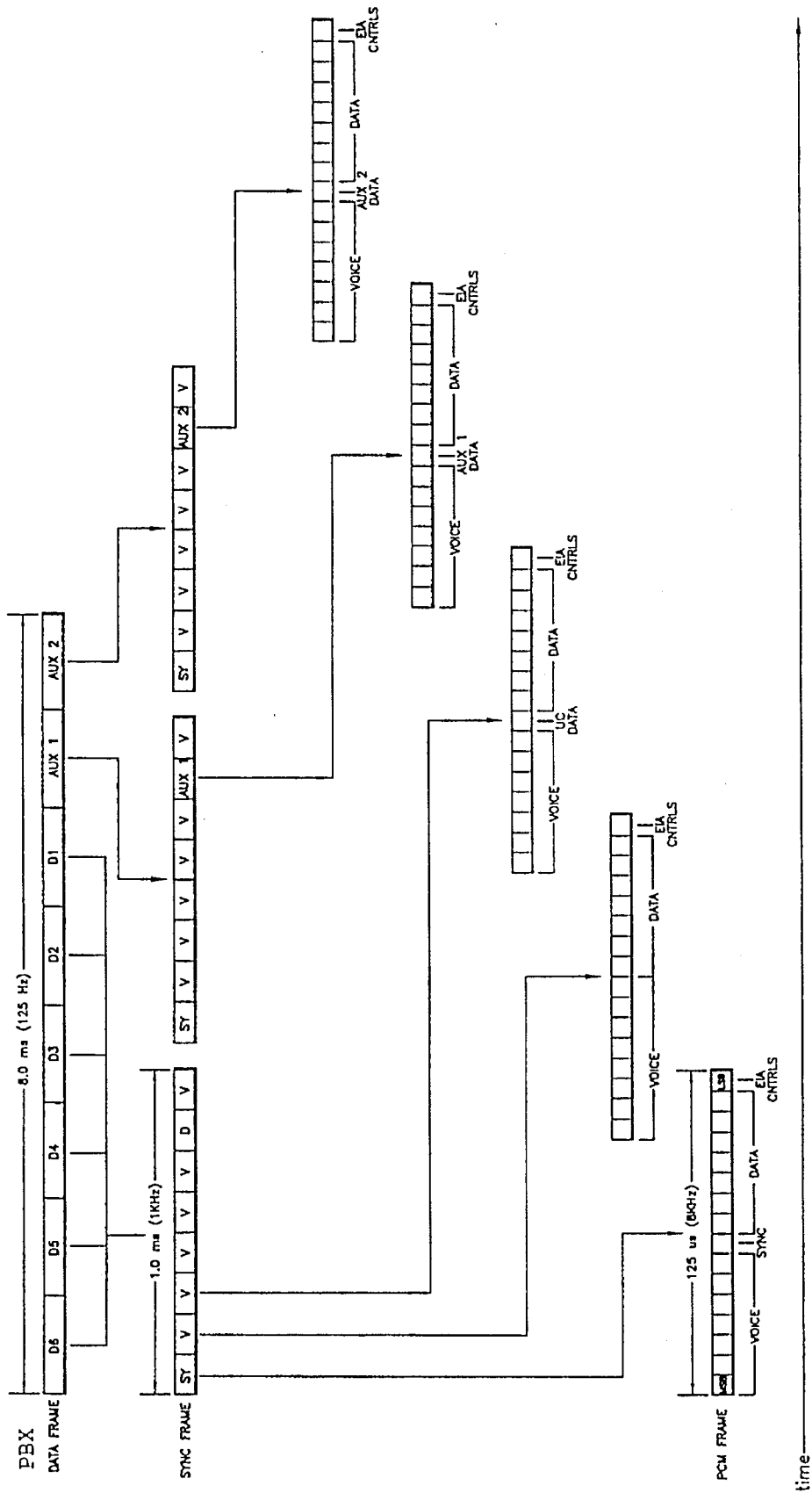
FIG. 28 illustrates the data frames for communication from the private-branch exchange to the stations in an expanded form.

FIGS. 26–28 illustrate typical system timing and format diagrams for the communication of data frames between the stations of the present invention and the PBX 2430. As shown in FIG. 26, the data transmitted from the microprocessor or microcontroller (hereinafter identified as "microprocessor") within each station is configured in a 16 bit parallel data word on the microprocessor data bus, which is preferably framed by one (1) start bit and seven (7) stop bits. Communications with the PBX system, on the other hand, are in a serial mode, therefore, the 16 bit parallel data word is converted to a serial data stream in the telephone circuit within each station, via parallel-to-serial converter 4620, shown in FIG. 25. In addition, a synchronization bit (sync bit) is added into each microprocessor data frame to maintain clock alignment between the PBX and the station.

Preferably, telephone voice transmissions between the PBX and the telephone are in the PCM format which may utilize the primary, secondary or both channels. As shown in FIG. 25, PCM CODEC 4630 compresses the voice information into PCM format. Transmitter conditioner 4640 amplifies and modulates each frame for transmission to the PBX 2430. The primary channel is preferably a 64 kilobits channel used to transfer control information to and from peripheral devices (e.g., the PBX), a synchronization bit for the hardware, and the voice signal. The secondary channel is also a 64 kilobit channel which is utilized to transfer EIA data and controls for serial communications, such as for RS-232 applications.

FIGS. 27 and 28 illustrate exemplary message frame formats and timing in an expanded form for telephone voice and data information between each station and the PBX. As shown in FIG. 27, data from the microprocessor is in a 16 bit parallel format and is framed by one start bit and seven stop bits to form the microprocessor (uP) data frame, where each uP data frame is approximately 8 ms in length. Telephone voice, data and information packet including transmitter ID from microprocessor 3510, shown in FIG. 25, is then converted to a serial data bit stream via parallel-to-serial converter 4620 which then transfers the serial signal to transmitter conditioner 4640. Transmitter conditioner 4640 amplifies and modulates the PCM signal for transmission to the PBX 2430 via the 4-pair telephone wire.

An exemplary embodiment of the format and timing of data transmitted from the PBX to a telephone, patient station, staff station or nurse control station is shown in FIG. 28. Return telephone voice and data information, e.g., data to notify a called party who called, is generated in the PBX and is formatted into an 8 bit PBX data frame of approximately 8 ms. in length (i.e., 1 ms/bit). Two of the eight bits are designated as auxiliary. A sync frame is then added into each bit portion of the PBX data frame and the resultant signal is conditioned for PCM transmission to a station, e.g., either nurse control station 2414, patient station 2415 and/or staff station 2418.

Referring again to FIG. 25, the PCM signal received at a station from PBX 2430 is processed through a waveshaper and conditioner 4650. The waveshaper and conditioner 4650 converts the received signals from the PCM format to a serial digital format, recovers the synchronization clock to sync the timing via phase-locked loop 4670, and recaptures the telephone voice and data information. Data retrieved by the receiver waveshaping and conditioning 4650 is transferred to serial-to-parallel converter 4660 which converts the data from a serial format to a parallel format for interaction with microprocessor 3512 and PCM CODEC 4630. PCM CODEC 4630 decodes the digital voice information for subsequent transmission of analog voice information to control unit 3210 for broadcast through speaker 4720, shown in FIG. 29.

According to the alternative embodiment, infrared sensitive photodiodes 4810 of receiver 4800 senses infrared transmissions from an infrared transmitter and converts the infrared signals to electrical signals. Waveshaper and conditioner 4820 conditions and amplifies the electrical signals and FM receiver 4830 demodulates the data for the carrier signal and serially transfers the received data to an I/O port of microprocessor 3512. According to the alternative embodiment of the invention, the receiver 4800 is capable of receiving infrared transmissions from portable transmitters at a distance of around 30 feet or greater from the station. Microprocessor 3512 receives the serial data from the FM receiver 4830 and extracts the transmitter ID information. The extracted information is reformatted and forwarded in an information packet to the PBX 2430 or the central processing unit 2412 for further processing and location determination.

FIGS. 33–38 show the components of an exemplary wireless electromagnetic transmitter, such as an infrared transmitter, which may be incorporated into a badge unit 5110, as well as various other known portable mediums, and a personnel or patient card 5200. The badge units are preferably adapted to be worn by staff members and/or patients within a health care facility using clip 5120, or adapted to be releasably attached to stationary or mobile devices or equipment using a suitable adhesive, identified as 5130, or like mediums such as VELCRO®. In instances where the transmitters are attached to devices or equipment, the transmitter permits tracking of such devices so as to permit staff members to easily determine the location of the device for retrieval and allow the badges to transmit information regarding the status of the equipment, such as on/off status. The badge unit includes a microcontroller 4900 for controlling the operations of the badge and a transmitter 4910 for transmitting signals to a plurality of receivers. The microcontroller 4900 is preferably a single integrated circuit chip which includes a processor and RAM and ROM memory.

Figure 33:
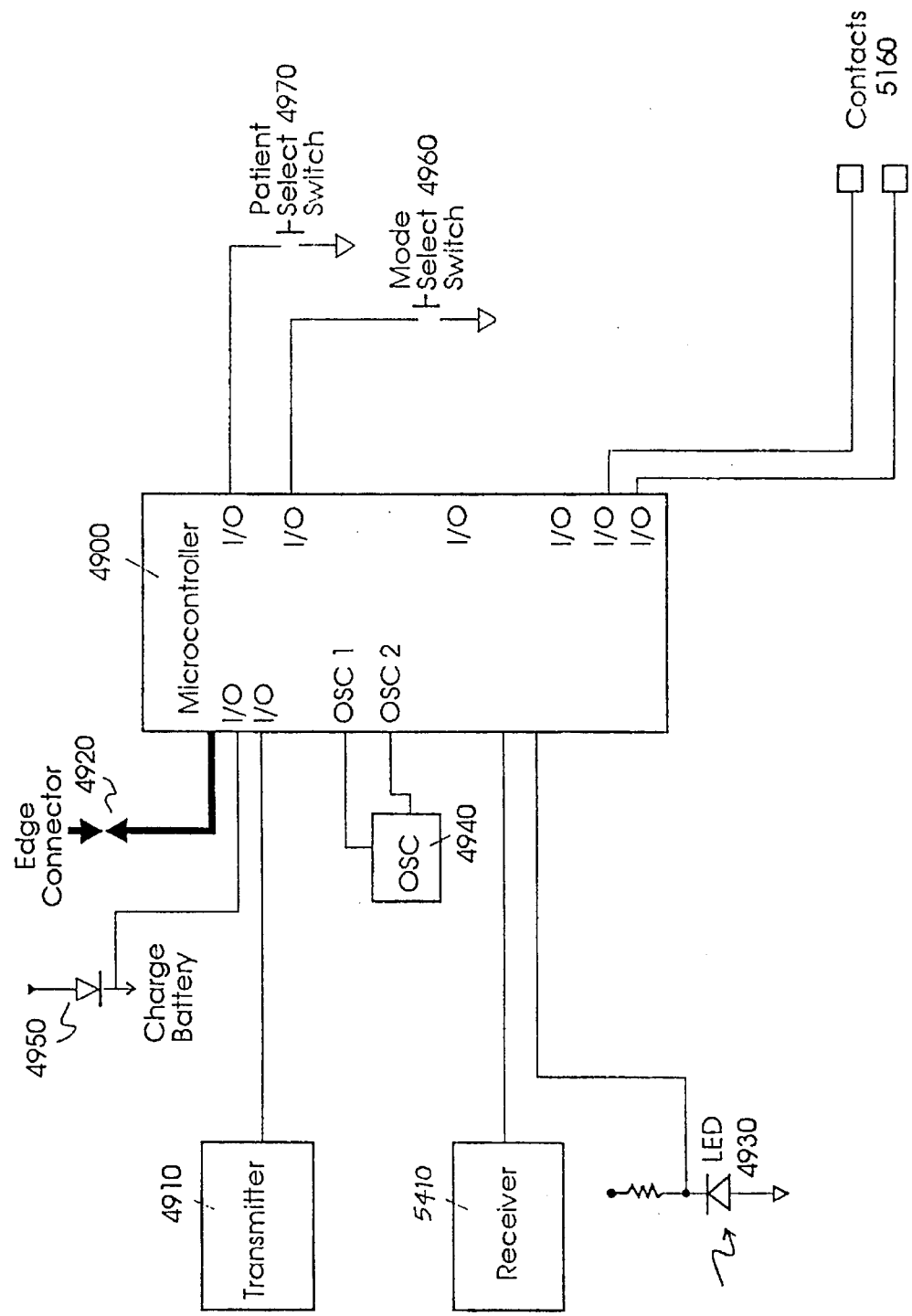
FIG. 33 is a block diagram of the components of an exemplary portable transmitter according to the present invention.
Figure 34:
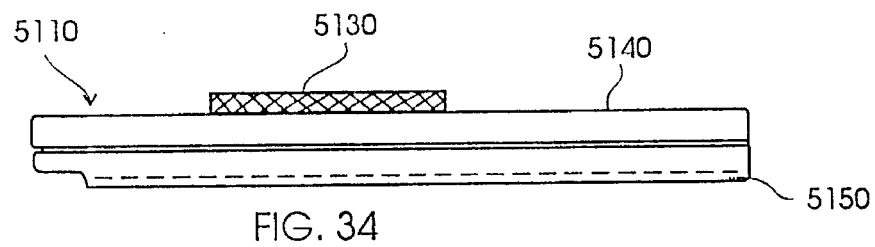
FIGS. 34–36 illustrate a side elevational view, top plan view and a bottom plan view, respectively, of a housing for the transmitter components of FIG. 33.
Figure 35:
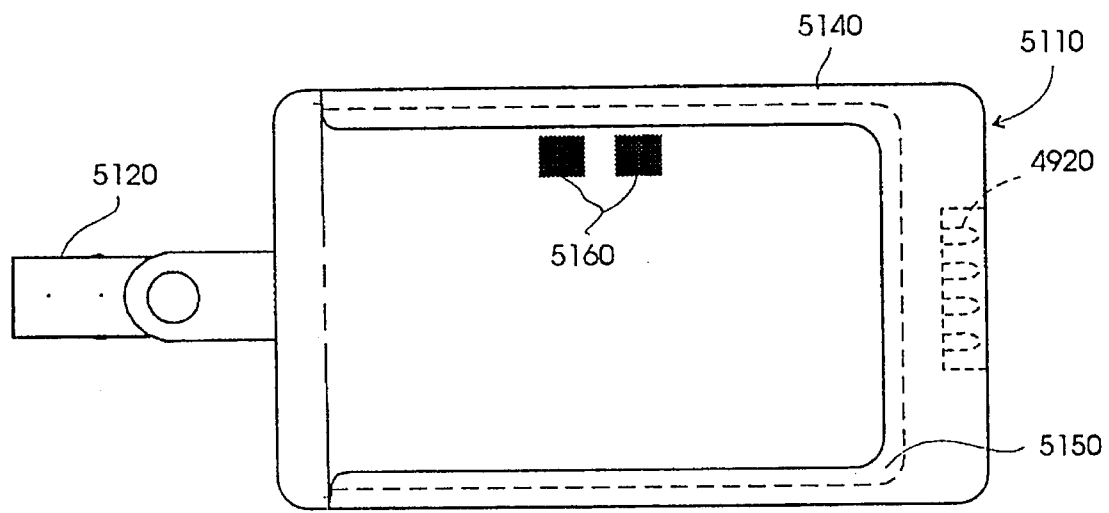
Figure 36:
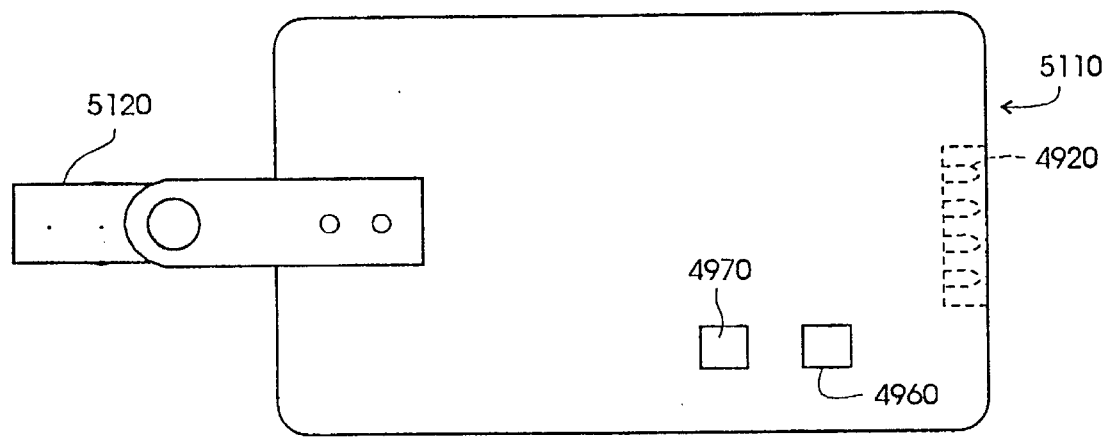

Preferably, the transmitter is enclosed in a housing which is shaped and sized like an ordinary credit card or smaller. FIGS. 34–36 illustrate the side, top and bottom views, respectively, of the badge housing. The housing 5140, as shown, is approximately 3.8 inches in length, 2.27 inches in width and 0.39 inches in thickness. The housing 5140 includes a slot 5150 which is configured to receive personnel card 5200 shown in FIGS. 37 and 38. Badge unit 5110 also includes electrical contacts 5160 which are connected to microcontroller 4900 of badge unit 5110 as shown in FIG. 33. Contacts 5160 are provided to engage corresponding contacts 5220 on the personnel card 5200 for data communications therebetween, as will be described in more detail below. A more detailed description of the badge unit is described in commonly assigned U.S. patent application Ser. No. 08/087,394, filed Jul. 2, 1993 which is incorporated herein by reference.

The ROM memory may be of the programmable type and stores software programs for operating the badge. These programs include: programs for controlling the transmitter 4910; for monitoring operational parameters; and for interfacing with external devices. The RAM memory includes a database for storing information including an identification code of the badge and operational parameters which are retrieved and monitored by the processor for operating the badge unit. The database may further include information regarding the person associated with the badge, e.g., medicine which the person is allergic to. The database may also include information relating to an associated object, e.g., medical equipment and its operating parameters or data.

Functions associated with the processor include: logical and arithmetic operations and coordination of data transfer to and from the microcontroller 4900. In the preferred embodiment, the processor also performs a fail safe function which periodically transmits a message to the central processing unit 2412 via patient station 2416 and PBX 2430. The periodic message, e.g., a fail safe code, is provided to inform the central processing unit 2412 that the badge is operational. Thus, if the message is not received from the badge unit, the central processing unit 2412 determines that either the badge unit has malfunctioned or that the badge unit is not within the operational confines of the system of the present invention, e.g., a staff member has left the hospital environment. The identification code of the badge may be utilized as the fail safe code which is periodically transmitted.

A microcontroller such as the PIC®16C5X manufactured by Microchip Technology, Inc. is used in the preferred embodiment of the present invention. It is apparent to one skilled in the art that any microcontroller having equivalent performance characteristics and similar in size may also be used.

An edge connector 4920, shown in FIG. 36, facilitates interfacing to the components of the badge from an external device, such as diagnostic medical equipment (not shown). The edge connector 4920 preferably has four connections which include a "Bidirect I/O" connection to an input/output port of the microcontroller 4900 for bidirectional communication with the microcontroller 4900. Data can be written into or read out of the microcontroller memory by the external device ("the Base") through this connection. The Base preferably includes processing, storage and interfacing capabilities for communicating with and transferring information between the Base and the badge. A standard serial interface protocol such as RS232 may be used for such communications. In instances where the badge unit is connected to a medical device, such as a heart monitor, connector 4920 is connected to the serial port of the heart monitor and status data, e.g., the heart rate of the patient being monitored, of the heart monitor is transferred to microcontroller 4900 and then transmitted via transmitter 4910 to the patient station receiver described above, or to an independent wireless receiver which will be described hereinbelow.

Another connection associated with edge connector 4920 is an "In-Base" connection which is monitored by the microcontroller 4900. An active signal at the "In-Base" input indicates that the microcontroller is to relinquish control to the external device. The badge according to the present invention is powered by a battery, which preferably is made of lithium. Other battery designs such as NICAD (nickel cadmium) rechargeable type or solar cell may also be used. The charge battery LED indicator 4950 provides a visual indication of the charge status of the battery. The charge battery circuitry may also be connected to microcontroller 4900, as shown in FIG. 33, so that the microcontroller can transfer the battery charge status information to the patient station via transmitter 4910. Alternatively, microcontroller 4900 may include a software counter which counts the number of transmissions from transmitter 4910 to determine the battery charge status of the badge. After a predetermined number of transmissions, microcontroller 4900 transmits to the patient station the battery charge status information, e.g., the battery power is low. Preferably, the predetermined number of transmissions is based on the average power used per transmission and the statistical life of the battery.

Another input of the edge connector 4920 may be used to recharge the battery. The fourth connection of the edge connector 4920 is a spare input/output. The badge includes a light sensitive LED 4930 for providing wireless means for inputting data to the microcontroller 4900 by serially strobing data with a light source into the microcontroller 4900.

An oscillator 4940 is connected to the microcontroller 4900 for providing an oscillation signal, which in turn generates a clock signal for clocking or timing purposes. In the preferred embodiment, the oscillator 4940 includes a resistor/capacitor combination for providing a clock which operates at a frequency of around 455 kilohertz. Due to variations in the tolerances of the resistor/capacitor combination, the clock rate for each badge unit will vary from one badge to another substantially around 455 kilohertz. The microcontroller 4900 includes a prescaler for providing time and clock signals.

A mode select switch 4960, preferably a normally open pushbutton switch, facilitates manual communication to the microcontroller 4900 for functions such as mode select or transmission of a preselected message. Typically, the function selected is dependant upon the number and sequence of button pushes. Examples for the modes of operation include: "erase memory" for erasing the contents of the RAM memory; "turn-off transmitter" for disabling any transmission from the badge; "card reinsertion" for turning off the badge when the personnel card is removed until a card is reinserted; "ID code change" for changing the ID code to a special preselected code to signal an abnormal condition; and "disable counters" mode, which overrides parameter operations for turning off or disabling the badge and maintains badge operations.

Figure 39:
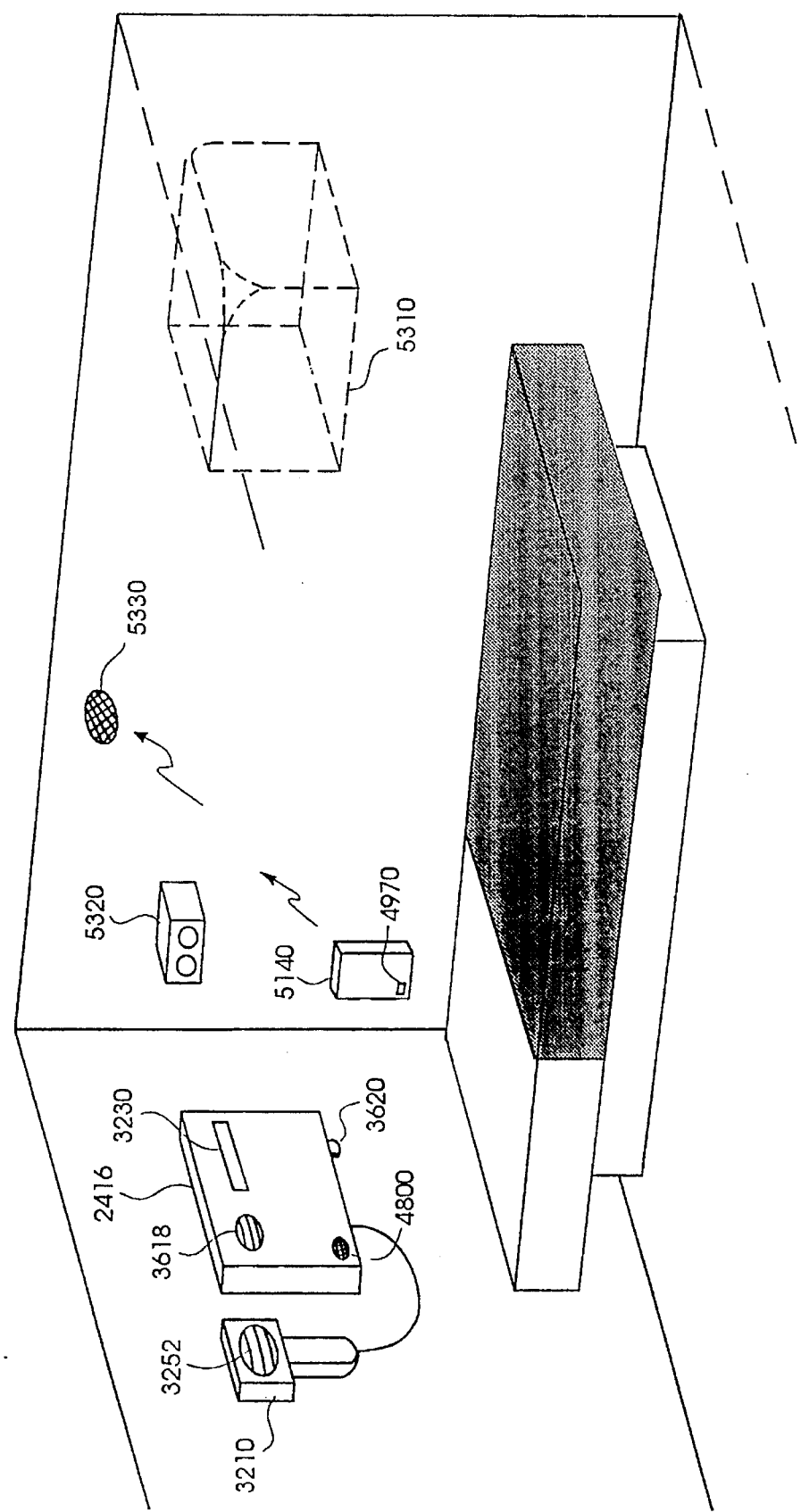
FIG. 39 is an exemplary configuration for a patient room within a health care facility.

Badge units which are worn by patients or releasably affixed to a structure which is proximal to the patient as shown in FIG. 39, may include a patient select switch or member 4970 shown in FIG. 36 which facilitates patient control of the environmental facilities within the patient's room and the nurse call function. Preferably, the patient select switch is a normally open pushbutton switch which controls such environmental facilities or the nurse call function via transmitter 4910 of the patient station 2416 and CPU 2412 utilizing the communication techniques described above. Such environmental facilities include, for example, the television 5310, radio, draperies, thermostat 5320 or the room lighting. Selection and control of a particular environmental facility or the nurse control function is dependant upon the number and sequence of button pushes. Data transmissions between the badge unit and the patient station is similar to the infrared data transmissions described above.

Figure 40:
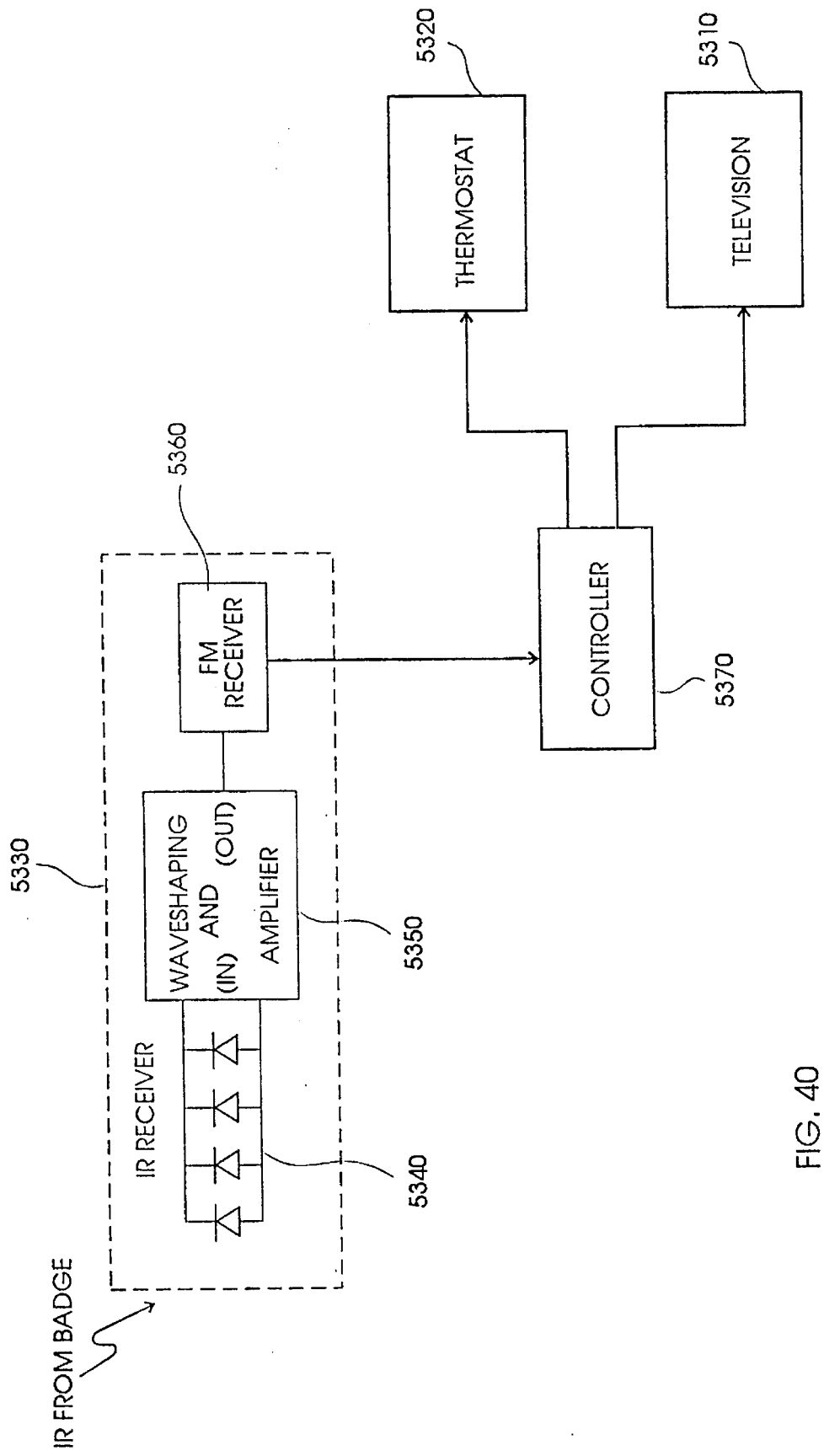
FIG. 40 is a circuit block diagram of an infrared receiver and environmental facilities within the patient room of FIG. 39, which are connected to a controller.

In an alternative embodiment shown in FIGS. 39 and 40, the badge unit may interface with an independent wireless electromagnetic receiver, preferably infrared receiver 5330. In one embodiment, each wireless receiver is located within the patient room and connected to a controller 5370 which responds to control data received from receiver 5330 to control the environmental facilities. In another embodiment, each wireless receiver is connected to either the central processing unit 2412 through zone controller 2420 or to the PBX 2430. In this embodiment, central processing unit 2412 or PBX 2430 will respond to the control data in a similar manner as controller 5370 and communications between the independent receiver and the central processing unit 2412 or the PBX 2430 is similar to the above described communications relating to receiver 4800, shown in FIGS. 23 and 25. As shown in FIG. 40, infrared light sensitive diode array 5340 receives infrared signals, preferably frequency modulated infrared signals, transmitted from badge units 5140 within approximately 30 feet of the receiver. Waveshaping and amplifier network 5350 conditions and amplifies the signals generated by the diode array 5340. FM receiver 5360 demodulates the control data from the carrier signal and serially transfers the received control data to controller 5370.

Referring to FIG. 40, each independent infrared receiver 5330 is connected to a controller 5370 having a processor, memory and stored programs. Controller 5370 receives the serial data from FM receiver 5360 and extracts the badge control data, e.g., the number and sequence of button pushes of the patient select switch 4970. The extracted control data is processed by controller 5370 to determine which environmental facility is being selected and which control function is to be performed. Preferably, each environmental facility is assigned an identification code which is stored in the memory of the controller. In this configuration, when control data is received by the controller, the controller determines which identification code has been received to select the desired environmental facility. For example, if the controller determines that the television has been selected, the controller may then be instructed to turn the television on or off, to change the channel or to increase or decrease the volume. A more detailed description of the FM infrared receiver and its operation is described in U.S. Pat. No. 4,977,519 to J. Crimmins, which is incorporated by reference.

Figure 41:
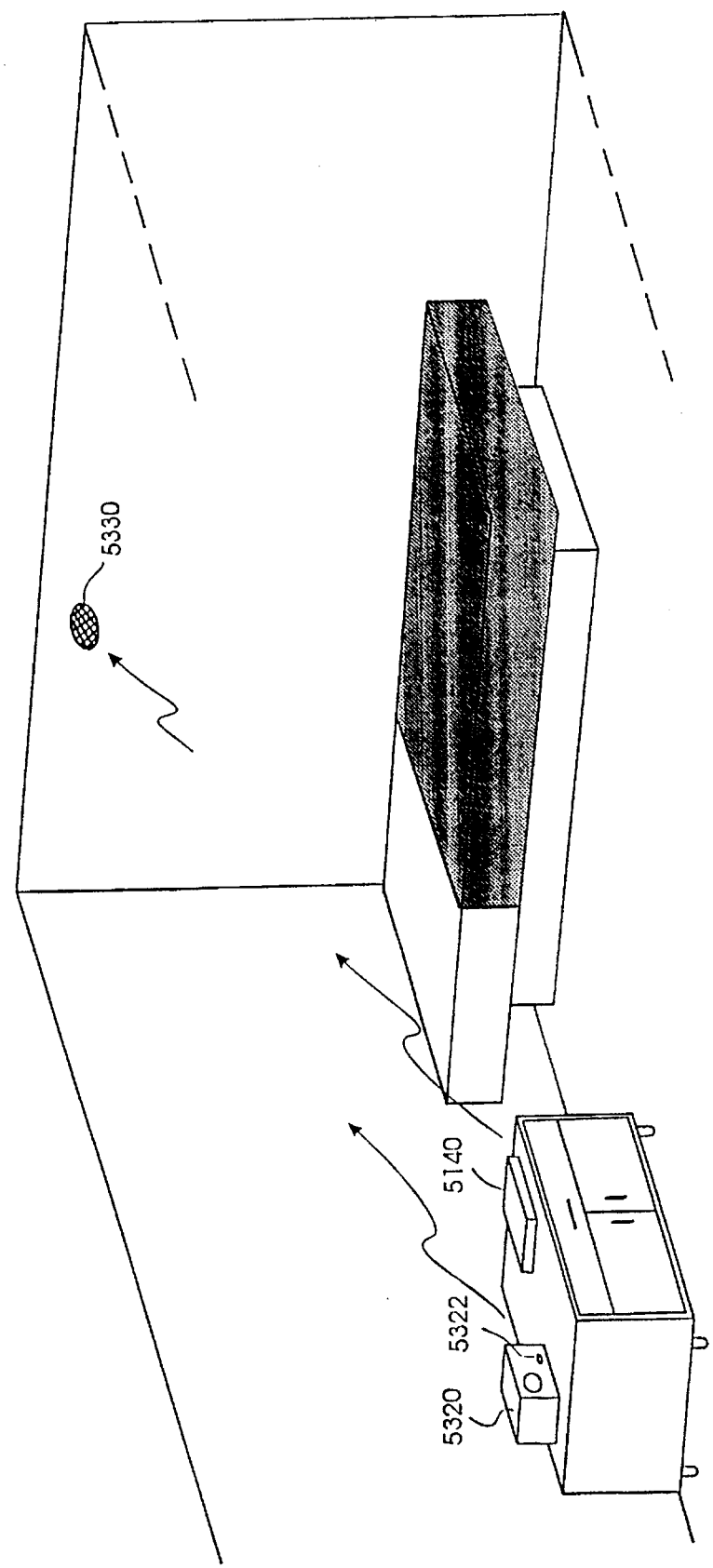
FIG. 41 is an alternative configuration for a patient room within a health care facility, illustrating the utilization of a wireless system for controlling environmental facilities in the room.

Referring to FIG. 41, an alternative embodiment of the patient room configuration of FIG. 39 is shown. In this embodiment, all devices which were connected by wires, e.g., the patient station 2416 and thermostat 5320 shown in FIG. 39, except the ceiling wireless receiver 5330, have been made wireless and portable. All functions performed by the devices within the room as shown in FIG. 39 are performed by the wireless units. The wiring installation of the system as shown in FIG. 41, simply requires the wiring installation of wireless receiver 5330 within each patient room, connecting the wireless receiver to a central computer, controller or to the PBX. Generally, previously wired devices for controlling the environment are replaced with a unit with an integral transmitter. For example, thermostat 5320 includes a wireless transmitter 5322. Thermostat 5320 measures the ambient temperature within the room and transmits the temperature data to receiver 5330 via transmitter 5322. In addition, the patient may control other environmental facilities within the room, e.g., a television, via badge 5140 as described above. As shown in FIG. 41, the thermostat 5320 and the badge 5140 are placed on a night stand within the room and proximal to the patient.

Figure 42:
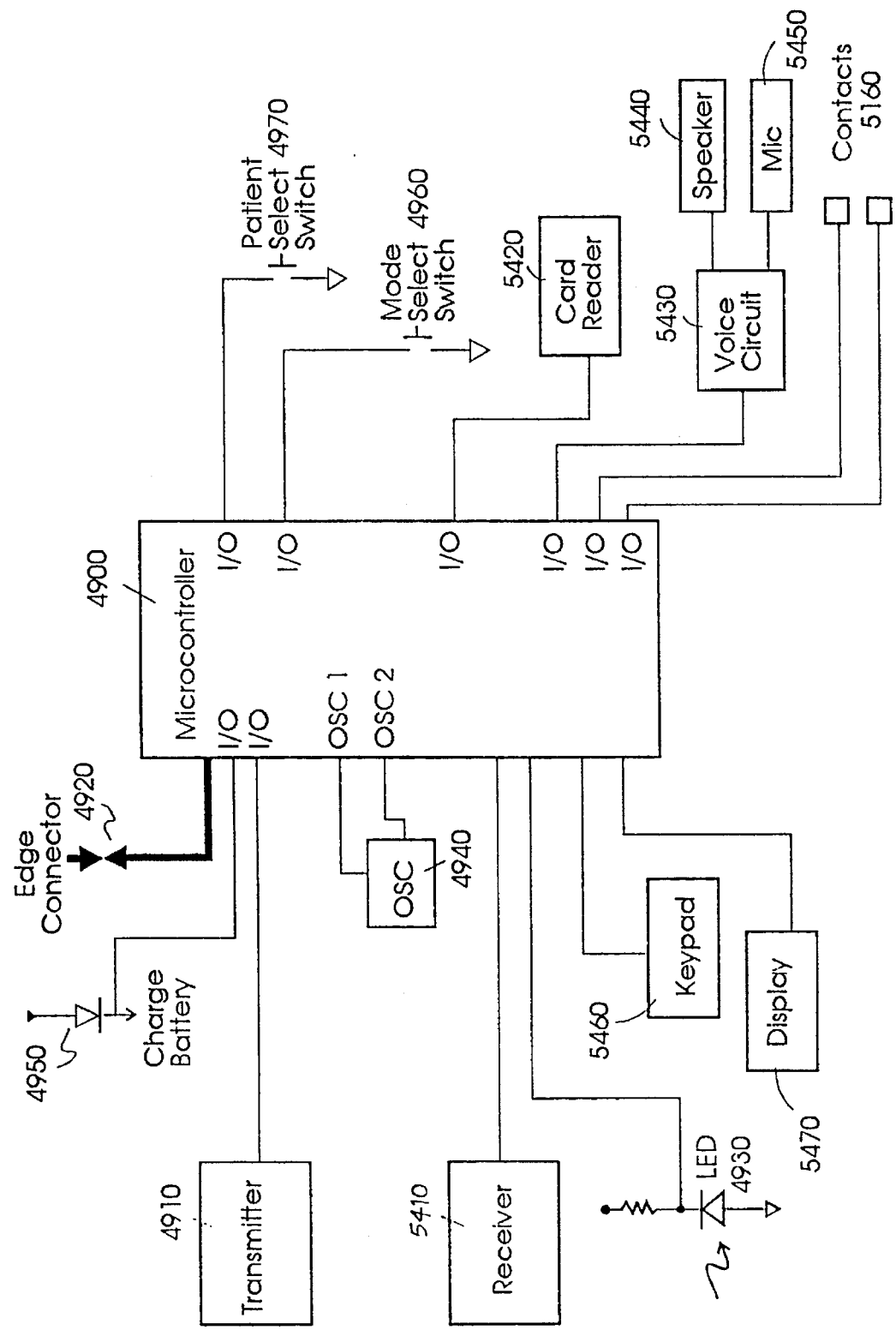
FIG. 42 is a block diagram of an alternative portable transmitter embodiment according to the present invention.

The functions of the patient station 2416 and pillow speaker 3210 may be performed by an enhanced badge unit having components as shown in FIG. 42. The enhanced badge unit includes voice and-display communication controls for communicating information previously performed by the patient station 2416 and pillow speaker 3210. The enhanced badge unit includes all the operations previously described for the badge unit and further includes: a wireless receiver, e.g., an infrared receiver 5410 for receiving information; a card reader 5420 for reading information stored in the personnel card; a voice circuit 5430 for receiving voice signals from speaker 5440 and for translating digital signals to audio signals received from microphone 5450; a keypad 5460 for keypad entry of data; a display 5470 for displaying information such as data entered from the keypad 5460 or data received from the receiver 5410; and a membrane switch (not shown) for special designated functions such as an emergency call or sending a selected message. A more detailed description of the enhanced badge unit is described in U.S. patent application Ser. No. 08/087,394, filed Jul. 2, 1993 which is incorporated herein by reference.

Figure 37:
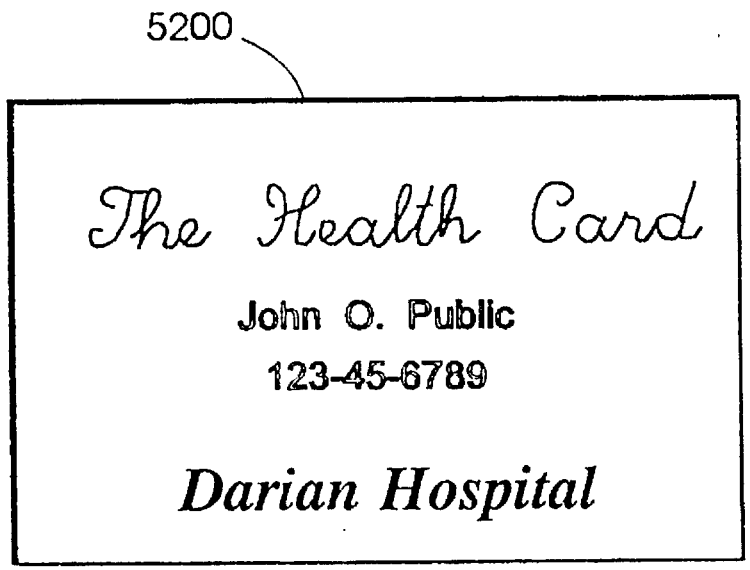
FIGS. 37 and 38 illustrate front and rear views, respectively, of a personnel card used with the transmitter housing and components of FIG. 35.
Figure 38:
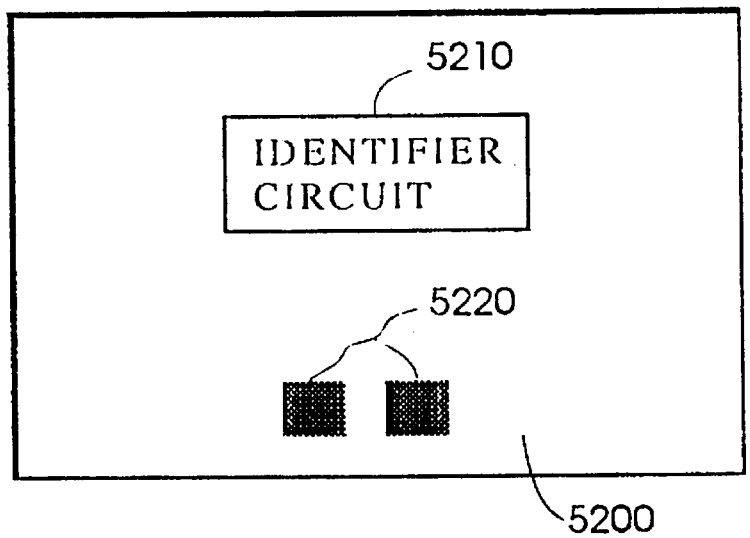

An exemplary personnel or patient card 5200 is shown in FIGS. 37 and 38 and operates in a manner similar to the personnel card shown and described in commonly assigned U.S. patent application Ser. No. 07/924,101, filed Aug. 3, 1992 which is incorporated herein by reference. As shown, the personnel card is configured and dimensioned for insertion within the slot 5150 of the badge unit 5110, shown in FIG. 35. The front surface of the card may include a printed logo and other identification information.

The rear surface of the card includes an identifier circuit 5210 which interfaces with microcontroller 4900 of the badge unit to perform a lockout function. The identifier circuit includes a ROM which has a validation code stored therein and circuitry to read the validation code from the ROM and transfer the data to electrical contacts 5220. Such circuitry is known to those skilled in the art. Preferably, the identifier circuit is in the form of a single integrated circuit which is preferably dimensioned at approximately 0.25 inches square and between about 0.002 of an inch and about 0.004 of an inch thick for mounting on the rear surface of the card. Electrical contacts 5220 of card 5200 are connected to identifier circuit 5210 so that when the card is inserted into the badge unit slot 5150, contacts 5220 are engaged with contacts 5160 of the badge unit. The identifier circuit transfers a validation code to the microcontroller 4900 of the badge unit. Microcontroller 4900 then determines whether the card validation code is valid so as to activate the badge unit circuitry and permit the person in possession of the card to use the badge unit. If the microcontroller 4900 determines that the validation code is improper or that no validation code is received, then microcontroller 4900 will deactivate the badge unit circuitry and prevent the person in possession of the card from using the badge unit.

Figure 29:
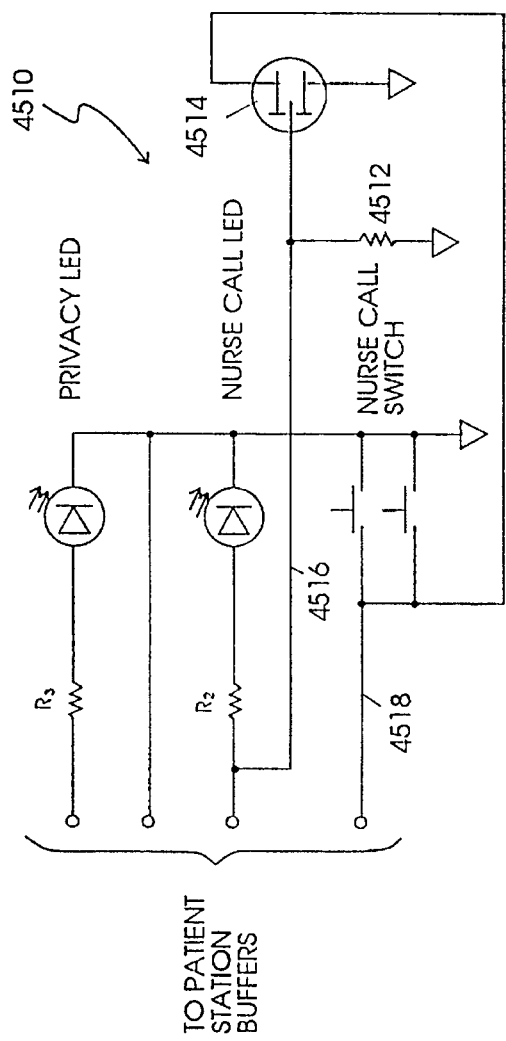
FIG. 29 is a circuit block diagram for an alternative embodiment of the internal circuitry for the patient control units illustrated in FIG. 23.

FIG. 29 is a circuit block diagram of the patient control unit 3210. Patient control unit 3210 includes telephone keypad 4710, speaker 4720 and microphone 4730 which are connected to PCM CODEC 4630 in telephone circuit 4610 and provide telephone voice and data communications between the patient stations and PBX 2430. The PCM CODEX 4630 may include a DTMF decoder for decoding DTMF tones from the telephone keypad 4710.

Figure 30:
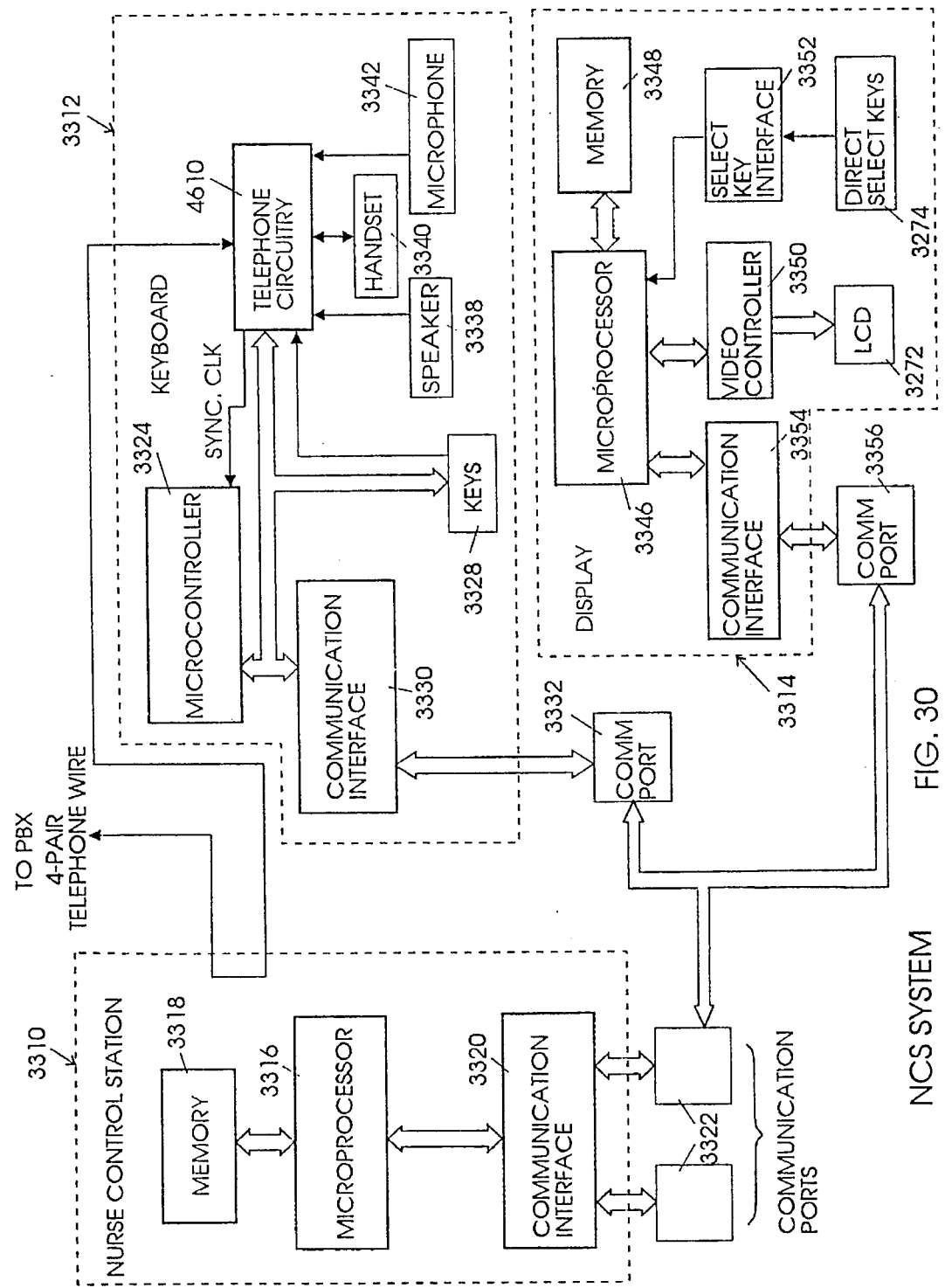
FIG. 30 is a circuit block diagram for an alternative embodiment of the internal circuitry for the nurse control stations illustrated in FIG. 23.

FIG. 30 is a circuit block diagram of the nurse control station 2414 which includes PBX interface or telephone circuitry 4610 connected to microcontroller 3324, keys 3328, speaker 3338, handset 3340 and microphone 3342 to provide telephone communications between the nurse control station and the other stations and/or to provide external telephone communications. Staff stations 2418 include the same components as shown in FIG. 25 for the patient stations 2416, except in the staff stations, the speaker 4018, keypad 4019 and microphone 4020 for providing telephone communications between the staff station and the other stations and/or to provide external telephone communications are integrated within the staff station. Communications between the staff stations 2418 and the PBX 2430 are same as described for the patient stations 2416 and are shown in FIGS. 26 to 28.

STATIONS USING A PBX FOR TELEPHONE AND SYSTEM DATA COMMUNICATIONS

Figure 31:
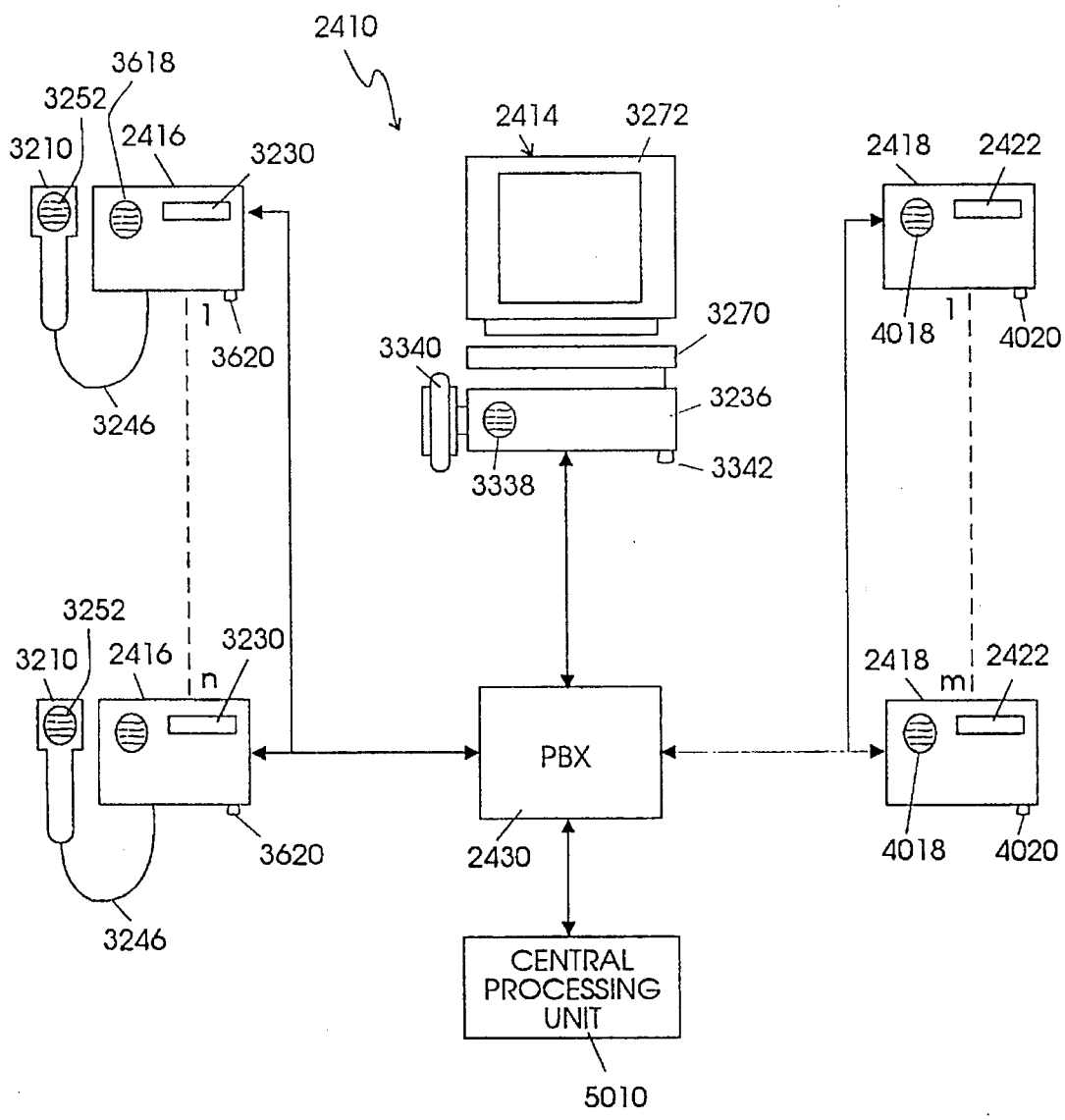
FIG. 31 is an illustration of the components of another alternative embodiment of the patient care and communication system configuration of the present invention.

Another alternative embodiment for the system configuration is shown in FIG. 31. In this embodiment private-branch exchange (PBX) 2430 is connected to central computer 5010, to nurse control stations 2414, patient stations 2416 and staff stations 2418 and is provided to facilitate system data communications as well as staff-to-staff, staff-to-patient and/or external telephone communications for the hospital environment.

Central computer 5010 provides standard control of PBX 2430 such as processing telephone data received by the PBX and providing the PBX with the connection information to interconnect particular stations for voice communications. For example, if a staff member attending a nurse control station calls a patient station where another staff member is attending to a patient, central processing unit 5010 processes the telephone data, e.g., patient station identity of the called party, and provides the PBX with the necessary information to interconnect the two stations. In addition, central processing unit 5010 is utilized to process the system data to perform system functions, e.g., the call priority, nurse follow, voice paging and room monitoring functions as previously described. The system data is preferably formatted in the following protocol by microprocessor 3512:

ST; SYSTEM DATA; SP where the ST field is a one byte start message field. The SYSTEM DATA field is preferably between one and 16 bytes in length and provides the PBX with the system data, e.g, code blue data. The SP field is a one byte stop message field.

According to an alternate embodiment, the PBX 2430 includes capabilities to process the telephone data and automatically connect the calling stations with the called stations for telephone and/or data communications independent of central processing unit 5010.

Figure 32:
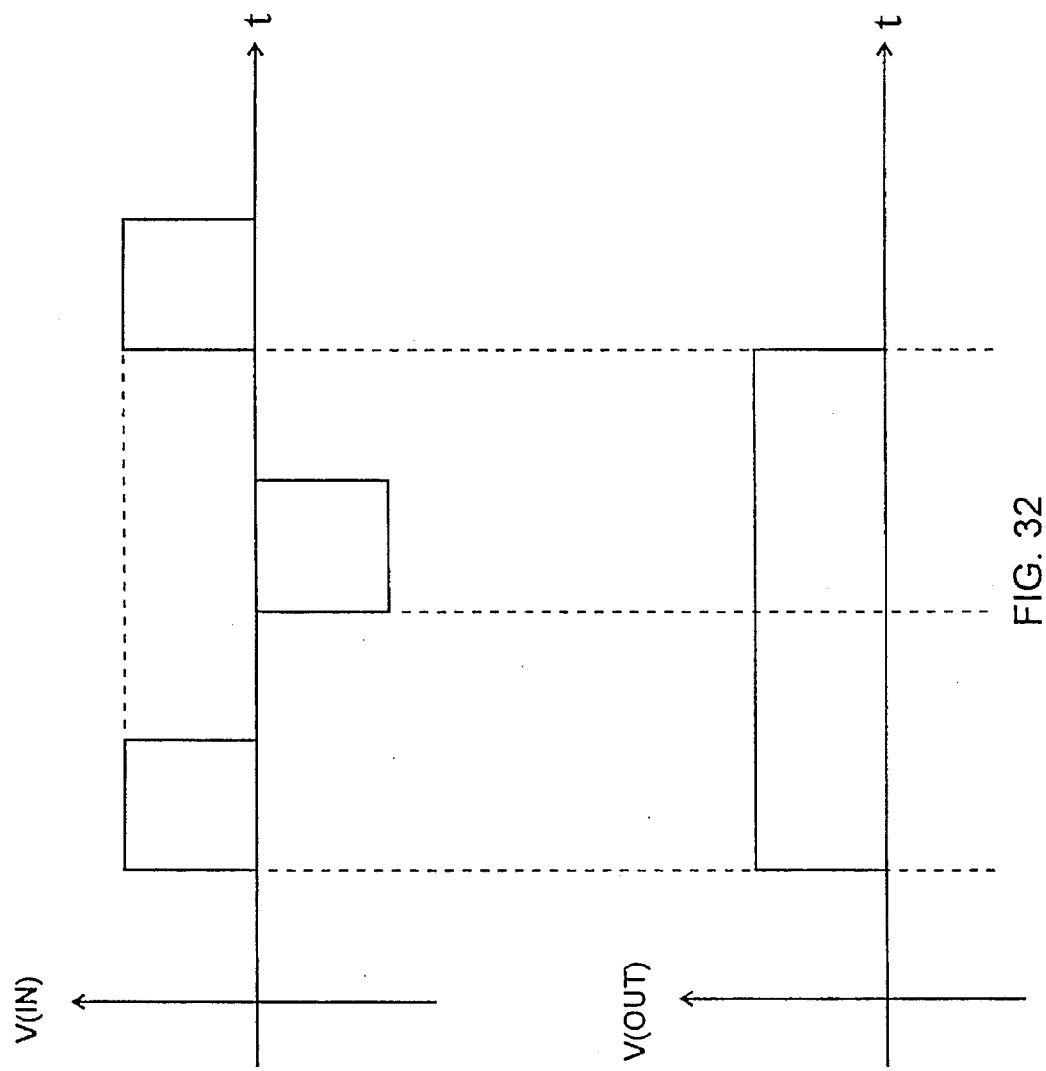
FIG. 32 illustrates exemplary input and output waveforms for the waveshaping and conditioning circuitry of FIG. 25.

The PCM signal received at a station from PBX 2430 is then processed through a waveshaping and conditioning network 4650, shown in FIG. 25. Network 4650 converts the received signal from the PCM format to a serial digital format, recovers the synchronization clock to sync the timing via phase-locked loop 4670, and recaptures the telephone voice and data information and the system data. System Data is retrieved by the receiver waveshaping and conditioning network 4650 using an alternate mark inversion (AMI) conversion technique. The AMI conversion method changes the level of the output signal for each positive crossing of the zero line by the input signal, as shown in FIG. 32.

It will be understood that various modifications can be made to the embodiments of the present invention herein disclosed without departing from the spirit and scope thereof. For example, various system configurations are contemplated, as well as various types of protocols utilized to communicate between the numerous stations utilized within the system of the present invention. In addition, numerous functions aside from those described herein may be programmed and performed in the system of the present invention. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A patient care and communication system which comprises:

a central station having means for facilitating visual and data communications relating to patient care; and a plurality of remote stations linked to said central station and having a processor for facilitating visual and data communications relating to patient care and having a display for displaying said visual communications; and a private branch exchange connected to a telephone exchange and to a plurality of telephones for facilitating telephone communication between said telephones and said telephone exchange;

wherein said central station facilitates said visual and data communications between said plurality of remote stations, and includes means for determining which of said plurality of remote stations are transmitting said visual and data communications and which of said plurality of remote stations are to receive said visual and data communications, and wherein said central station further includes means for establishing a communication link between said transmitting stations and said receiving stations; wherein each of said plurality of remote stations includes telephone circuitry connected to said private-branch exchange for facilitating telephone communication, each of said plurality of remote stations further includes a sensor for sensing energy radiated from portable transmitter units, the radiated energy includes respective identification signals associated with each of said transmitter units wherein at least a portion of said plurality of remote stations are configured and adapted for association in a group network such that predefined visual and data signal communications are transmitted to each remote station in the group by said central station and audio communications are transmitted by said private-branch exchange.

2. The patient care and communication system according to claim 1, wherein said plurality of remote stations includes control stations and patient stations.

3. The patient care and communication system according to claim 2, wherein said plurality of remote stations includes staff stations.

4. The patient care and communication system according to claim 3, wherein said central station includes means for directing said private-branch exchange to establish audio communication between a predetermined number of said control stations and a predetermined number of said patient stations and a predetermined number of said staff stations.

5. The patient care and communication system according to claim 2, wherein said patient stations include patient control means connected thereto, said patient control means including a keypad, a speaker and a microphone for telephone communications.

6. The patient care and communication system according to claim 2, wherein said central station includes means for directing said private-exchange to activate audio communications between said control stations and a predetermined number of said patient stations to facilitate audio monitoring of patient rooms from said control stations.

7. The patient care and communication system according to claim 2, wherein said control stations comprise a microprocessor for controlling the operation of said control stations and said private branch exchange, memory means connected to said microprocessor for storing programs and data, peripheral interface means for interfacing said microprocessor to peripheral equipment so as to facilitate the input and output of said visual and data signal communications.

8. The patient care and communication system according to claim 2 further comprising locating means linked to said central station for determining the location of staff members and transferring said location of staff members data to said central station so as to facilitate visual and data communications between said control stations and said patient stations provided at said location of the staff members, said central station directing said private-branch exchange to activate audio communication between said control stations and said patient station at said location.

9. The patient care and communication system according to claim 1 further comprising zone controller means for interfacing said central station to said transmitting and receiving stations for data communications therebetween.

10. The patient care and communication system according to claim 1, wherein said plurality of remote stations include receivers adapted to receive and convert infrared transmissions to electrical signals.

11. The patient care and communication system according to claim 10 wherein each of said portable transmitter units is adapted to be releasably attached to an object and is adapted for infrared transmission.

12. The patient care and communication system according to claim 11 wherein each of said portable transmitter unit includes a housing and a processor within said housing.

13. The patient care and communication system according to claim 12, wherein said housing of each of said portable transmitter units includes a slot configured to receive a personnel card, each said housing having at least one electrical contact connected to said processor within said housing and said personnel card having at least one electrical contact engagable with said at least one housing contact to permit the transmission of data between said personnel card and said processor within said housing.

14. The patient care and communication system according to claim 13, wherein said personnel card includes an identifier circuit which transfers validation data to said processor within said housing, wherein said processor within said housing determines if the validation code is valid so as to activate the respective portable transmitter unit and permit the person in possession of said card to use the respective portable transmitter unit.

15. The patient care and communication system according to claim 11 wherein each of said portable transmitter unit transmits data substantially periodically to said remote stations so as to provide said central station with information reflecting the status of each of said portable transmitter unit.

16. The patient care and communication system according to claim 15, wherein said status information includes a message that each of the portable transmitter unit is operational.

17. The patient care and communication system according to claim 15, wherein said status information includes battery charge data.

18. A patient care and communication system which comprises:

a central station having means for facilitating visual and data communications relating to patient care; and a plurality of remote stations linked to said central station and having a processor for facilitating visual and data communications relating to patient care and having a display for displaying said visual communications; and a private branch exchange connected to a telephone exchange and to a plurality of telephones for facilitating telephone communication between said telephones and said telephone exchange;

wherein said central station facilitates said visual and data communications between said plurality of remote stations, and includes means for determining which of said plurality of remote stations are transmitting said visual and data communications and which of said plurality of remote stations are to receive said visual and data communications, and wherein said central station further includes means for establishing a communication link between said transmitting stations and said receiving stations; wherein each of said plurality of remote stations includes telephone circuitry connected to said private-branch exchange for facilitating telephone communication, each of said plurality of remote stations further includes a sensor for sensing energy radiated from portable transmitter units, the radiated energy includes respective identification signals associated with each of said transmitter units wherein each of said transmitter units include a housing and a processor within said housing and a patient select member connected to said processor to permit persons within a room to control environmental facilities within the room.

19. The system according to claim 18, wherein said patient select member is activated to cause the respective transmitter unit to transmit a preassigned message to said central station.

20. The system according to claim 19, wherein said preassigned message includes information reflecting the status of the respective transmitter unit.

21. Apparatus for monitoring and controlling environmental facilities within at least one room of a health care facility, which comprises:

at least one nurse control station located at a nurse station and a plurality of remote stations, at least one remote station located in said at least one room, said remote stations connected to a central processor to facilitate visual and data communications therebetween, said plurality of remote stations having processing means for facilitating said visual and data communications and having display means for displaying said visual and data communications, and said central processor having means for determining which of said plurality of remote stations are transmitting said visual and data communications and which of said plurality of remote stations are to receive said visual and data communications, and having means for establishing a communication link between said transmitting stations and said receiving stations;

a wireless receiver positioned within said at least one room having environmental facilities therewithin;

a wireless transmitter located within said at least one room, said wireless transmitter having a housing, a processor within said housing and a patient select member connected to said processor, such that activation of said patient select member causes said wireless transmitter to transmit control data to said wireless receiver associated with the patient select member; and a controller connected to said wireless receiver and said environmental facilities, said controller being configured to receive said control data from said wireless receiver and to control said environmental facilities in response to said control data, wherein said control data is transmitted to said at least one nurse control station for monitoring said environmental facilities at said at least one remote station.

22. The apparatus according to claim 21, wherein said environmental facilities include a thermostat.

23. The apparatus according to claim 22, wherein said thermostat is portable and includes a wireless transmitter to transmit temperature data to said controller to permit the controller to regulate ambient temperature within said room.

24. The apparatus according to claim 21, wherein said wireless receiver comprises an infrared receiver and said wireless transmitter comprises an infrared transmitter.

25. The apparatus according to claim 21, wherein said wireless transmitter includes a connector which facilitates connection of said wireless transmitter to medical equipment, reception of status data from said medical equipment and transmission of said status data to said wireless receiver.

26. A method for monitoring and controlling environmental facilities within at least one room of a health care facility, comprising:

connecting a plurality of remote stations to at least one nurse control station located at a nurse station, at least one of said remote stations located in said at least one room, a central processor to facilitate visual and data communications therebetween, said plurality of remote stations having processing means for facilitating said visual and data communications and having display means for displaying said visual and data communications, and said central processor having means for determining which of said plurality of remote stations are transmitting said visual and data communications and which of said plurality of remote stations are to receive said visual and data communications, and having means for establishing a communication link between said transmitting stations and said receiving stations;

positioning a wireless receiver within said at least one room having environmental facilities therewithin;

positioning a portable wireless transmitter within said at least one room;

connecting said wireless receiver and said environmental facilities to a controller, said controller being configured to receive control data from said wireless receiver and to control said environmental facilities in response to said control data, wherein said control data is transmitted to said at least one nurse control station for monitoring said environmental facilities at said at least one remote station; and activating said wireless transmitter to transmit said control data.

27. The method according to claim 26, further including the step of transmitting temperature data from said portable wireless transmitter to said controller for regulating ambient temperature within said room.

28. The method according to claim 26, further including the step of connecting a medical equipment to said portable wireless transmitter for transferring status data from said medical equipment to said transmitter, wherein said transmitter in turn transmits said status data to said wireless receiver.

* * * * *